United States Patent
Franzese et al.

(10) Patent No.: US 12,214,181 B1
(45) Date of Patent: Feb. 4, 2025

(54) SYSTEMS, METHODS, AND APPARATUS FOR ADMINISTERING DRUGS VIA IMPLANTED ACCESS PORT

(71) Applicant: Matchstick LLC, Boonton, NJ (US)

(72) Inventors: Christopher James Franzese, Randolph, NJ (US); Martin Michael Coyne, III, Towaco, NJ (US); Alejandra Linares Martinez, Saddle Brook, NJ (US); Matthew Conner D'Auria, Bernardsville, NJ (US)

(73) Assignee: Matchstick LLC, Boonton, NJ (US)

( * ) Notice: Subject to any disclaimer, the term of this patent is extended or adjusted under 35 U.S.C. 154(b) by 0 days.

(21) Appl. No.: 18/587,365

(22) Filed: Feb. 26, 2024

Related U.S. Application Data

(60) Provisional application No. 63/448,136, filed on Feb. 24, 2023.

(51) Int. Cl.
*A61M 5/20* (2006.01)
*A61M 5/42* (2006.01)
*A61M 39/02* (2006.01)

(52) U.S. Cl.
CPC .............. *A61M 5/427* (2013.01); *A61M 5/20* (2013.01); *A61M 39/0247* (2013.01); *A61M 2039/0205* (2013.01); *A61M 2039/0261* (2013.01); *A61M 2039/0267* (2013.01); *A61M 2039/027* (2013.01)

(58) Field of Classification Search
CPC .... A61M 5/427; A61M 5/20; A61M 39/0247; A61M 2039/0205; A61M 2039/0261; A61M 2039/0267; A61M 2039/027
See application file for complete search history.

(56) References Cited

U.S. PATENT DOCUMENTS

| | | |
|---|---|---|
| 7,775,966 B2 | 8/2010 | Dlugos et al. |
| 7,780,590 B2 | 8/2010 | Birk et al. |
| 7,899,544 B2 | 3/2011 | Cantlon |

(Continued)

FOREIGN PATENT DOCUMENTS

| | | |
|---|---|---|
| WO | 2008002625 A2 | 1/2008 |
| WO | 2022149086 A1 | 7/2022 |

(Continued)

OTHER PUBLICATIONS

U.S. Appl. No. 18/587,153, filed Feb. 26, 2024, Pending, Christopher James Franzese, Martin Michael Coyne III, Alejandra Linares Martinez, Matthew Conner D'Auria.

(Continued)

*Primary Examiner* — Nathan R Price
*Assistant Examiner* — Haden Matthew Ritchie
(74) *Attorney, Agent, or Firm* — GTC Law Group PC & Affiliates

(57) ABSTRACT

A method for administering at least one drug to a patient includes determining, with a locator assembly of an apparatus, a location of an access port under a skin of the patient. The method further includes adhering a base plate of the apparatus to the skin of the patient at a location corresponding to the location of the access port, detaching the locator assembly from a base coupler of the base plate adhered to the skin, and administering, through an opening in the base plate adhered to the skin, a first drug to the patient.

17 Claims, 34 Drawing Sheets

(56) References Cited

U.S. PATENT DOCUMENTS

| | | | |
|---|---|---|---|
| 7,947,022 | B2 | 5/2011 | Amin et al. |
| 8,151,801 | B2 | 4/2012 | Hoendervoogt et al. |
| 8,192,398 | B2 | 6/2012 | Hoendervoogt et al. |
| 8,608,713 | B2 | 12/2013 | Beasley et al. |
| 8,998,860 | B2 | 4/2015 | Sheetz et al. |
| 10,052,471 | B2 | 8/2018 | Hamatake et al. |
| 2004/0133164 | A1* | 7/2004 | Funderburk ....... A61B 5/14532 |
| | | | 604/134 |
| 2007/0213837 | A1 | 9/2007 | Ferreri et al. |
| 2007/0233048 | A1 | 10/2007 | Petersen et al. |
| 2008/0051722 | A1 | 2/2008 | Ellsmere et al. |
| 2010/0331669 | A1 | 12/2010 | Hoendervoogt et al. |
| 2013/0102945 | A1 | 4/2013 | Long |
| 2014/0163326 | A1 | 6/2014 | Forsell |
| 2014/0200410 | A1 | 7/2014 | Mantell |
| 2019/0022306 | A1 | 1/2019 | Gibson et al. |
| 2019/0298408 | A1 | 10/2019 | Ravikumar et al. |
| 2020/0035348 | A1 | 1/2020 | Sartor et al. |
| 2020/0061288 | A1 | 2/2020 | Jho et al. |
| 2020/0179669 | A1 | 6/2020 | Mitchell et al. |
| 2020/0230390 | A1 | 7/2020 | Powers et al. |
| 2020/0368513 | A1 | 11/2020 | Amin |
| 2021/0001104 | A1 | 1/2021 | Evans et al. |
| 2021/0338928 | A1 | 11/2021 | Hooven et al. |
| 2022/0257862 | A1 | 8/2022 | McCullough et al. |
| 2022/0296160 | A1* | 9/2022 | Hooven ............. A61M 5/1409 |
| 2024/0057889 | A1 | 2/2024 | Ramirez et al. |

FOREIGN PATENT DOCUMENTS

| | | | |
|---|---|---|---|
| WO | 2022176433 | A1 | 8/2022 |
| WO | 2024178416 | A1 | 8/2024 |

OTHER PUBLICATIONS

U.S. Appl. No. 18/587,202, filed Feb. 26, 2024, Pending, Christopher James Franzese, Martin Michael Coyne III, Alejandra Linares Martinez, and Matthew Conner D'Auria.

U.S. Appl. No. 18/587,273, filed Feb. 26, 2024, Pending, Christopher James Franzese, Martin Michael Coyne III, Alejandra Linares Martinez, and Matthew Conner D'Auria.

U.S. Appl. No. 18/587,345, filed Feb. 26, 2024, Pending, Christopher James Franzese, Martin Michael Coyne III, Alejandra Linares Martinez, and Matthew Conner D'Auria.

PCT/US2024/017264, Feb. 26, 2024, Pending, Christopher James Franzese, Martin Michael Coyne III, Alejandra Linares Martinez, and Matthew Conner D'Auria.

PCT/US2024/017264 , "Application Serial No. PCT/US2024/017264, Invitation to Pay Additional Fees and, Where Applicable, Protest Fee mailed May 30, 2024", 3 pages.

PCT/US2024/017264 , "International Application Serial No. PCT/US2024/017264, International Search Report and Written Opinion mailed Jul. 17, 2024", Matchstick LLC, 25 pages.

* cited by examiner

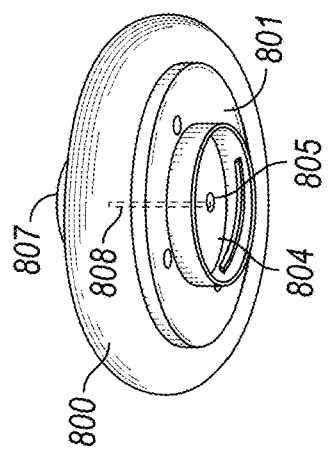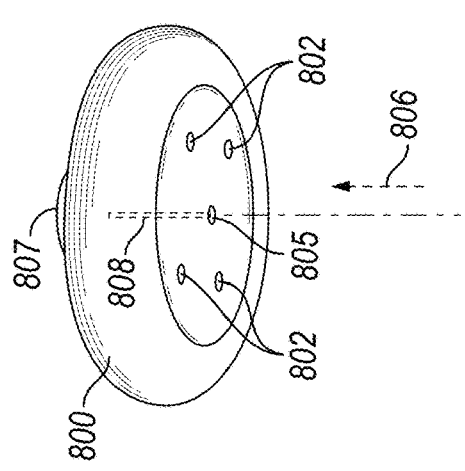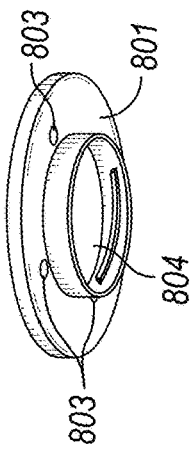

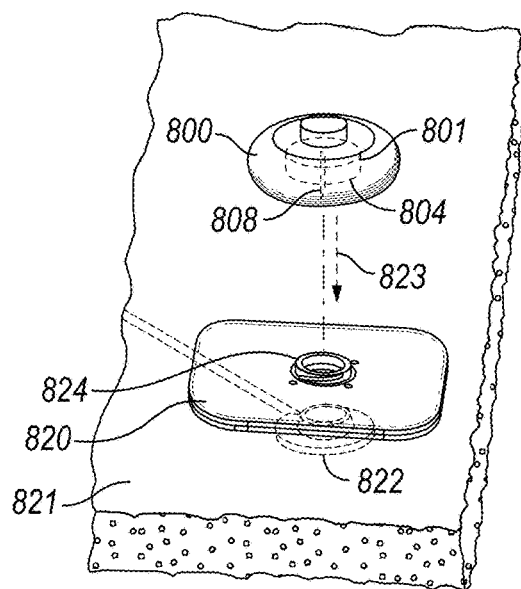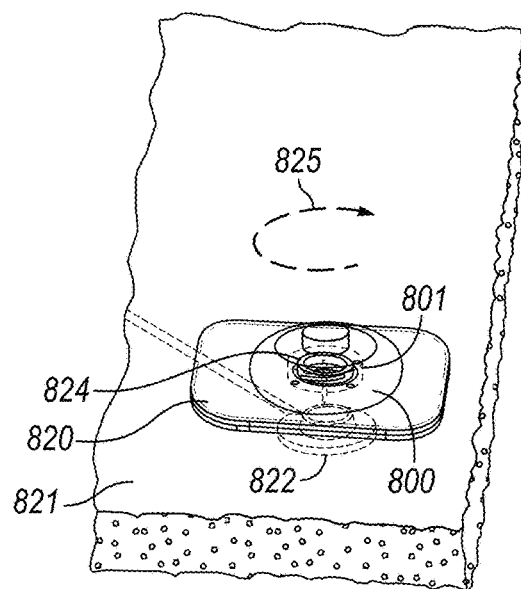
FIG. 8C-1  FIG. 8C-2
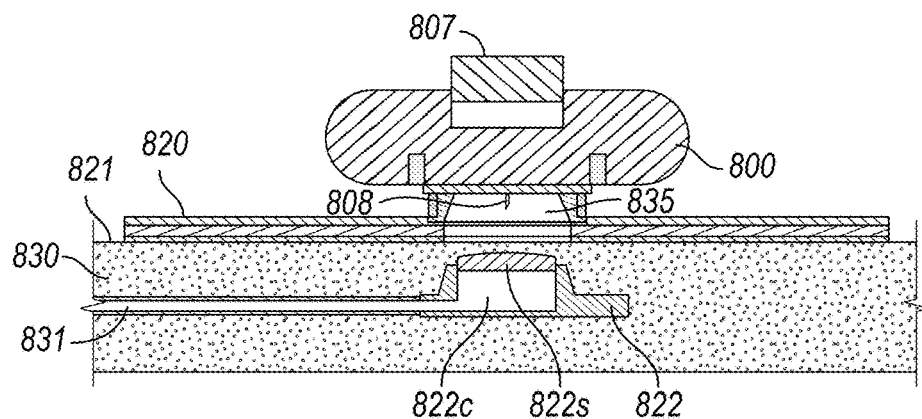
FIG. 8D-1A
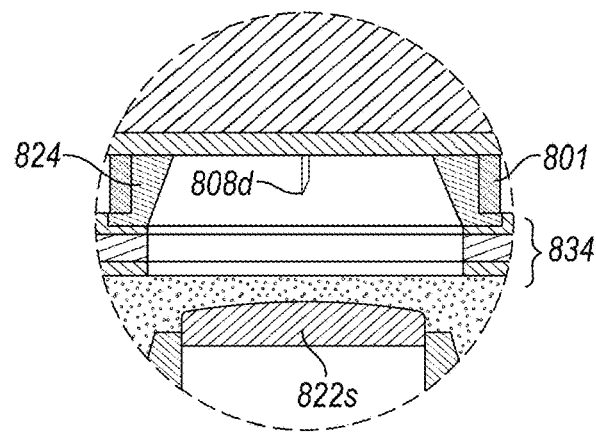
FIG. 8D-1B

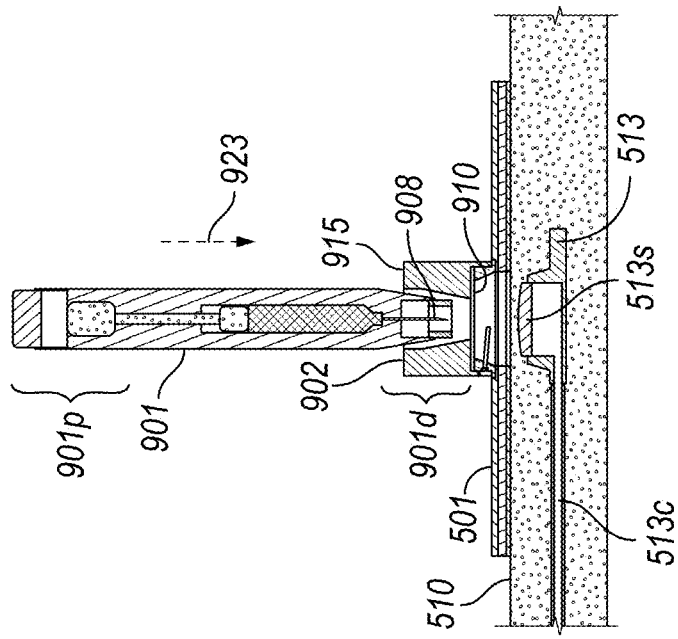
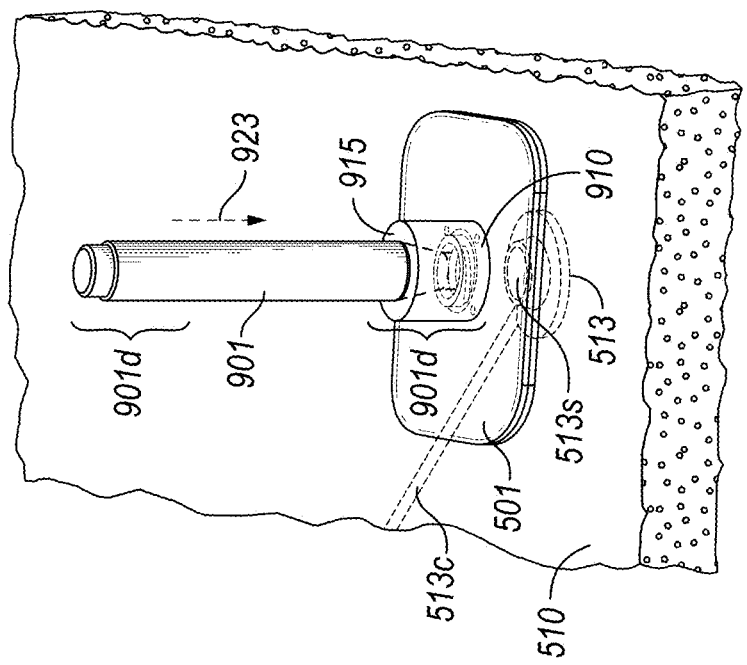
FIG. 9F-2
FIG. 9F-1

SYSTEMS, METHODS, AND APPARATUS FOR ADMINISTERING DRUGS VIA IMPLANTED ACCESS PORT

CROSS-REFERENCE TO RELATED APPLICATIONS

The present application claims the benefit of priority to U.S. Provisional Patent Application 63/448,136, entitled "IMPLANTED PORT LOCALIZING APPARATUS AND METHOD," filed on Feb. 24, 2023.

The foregoing application is incorporated herein by reference in its entirety for all purposes.

TECHNICAL FIELD

Principles and embodiments of the present disclosure may relate to improvements for infusion of medications through an implanted access port. For example, embodiments of the disclosure may relate to an improved apparatus and method for locating aspects of implanted access ports prior to delivery of one or more therapeutic medications. Further, embodiments of the disclosure may relate to improvements that simplify administration of medications via a located access port with a drug delivery device, such as a port access needle, wearable injector, or handheld injector.

BACKGROUND

Infusion and injection are medical procedures used to deliver a wide variety of therapeutic medicines of interest for a variety of diseases. Infusion, injection, and administration may take place by subcutaneous (SC), intramuscular (IM), intravenous (IV), or enteral administration routes. An administration route may be based on a specific medication's pharmacokinetic (PK) profile, formulation components, approved regulatory labeling, individual clinical judgment, or clinical necessity.

Infusion and injection may take place via the intravenous (IV) route, whereby medication may be delivered into various aspects of a patient's venous system. IV administration may require direct access to a patient's vein with a needle, catheter, or implanted venous port. Biologic medicines are frequently administered via the IV route. SC administration is generally considered less invasive and more straightforward for patients. Both IV and SC administration may variously be used for medicines to treat many diseases, especially chronic diseases.

A method for IV and SC administration of medications is using an implanted access port. Access ports may stay placed for weeks to years, making them particularly advantageous to deliver treatment regimens administered over long timeframes, often with administrations separated by weeks. Access ports may reduce the risk of infection, provide discretion to patients as they are hidden under the skin, and allow patients to perform normal activities of daily living. As a result, they are increasingly being used, particularly as chronic disease becomes more prevalent, as treatments become more intensive, and medications must be administered repeatedly over longer periods of time.

Access ports may generally include a port housing defining a cavity, a septum sealing the open end of the cavity, and an outlet in fluid communication with a catheter. The catheter, in turn, may be placed into fluidic communication with a part of the patient's anatomy, such as the venous system, during port implantation. The septum may be generally elastomeric and designed to be repeatedly pierced by a needle and re-seal after a needle is removed. Variations of access ports exist with variations in sizes, shapes, materials, profile, number of septa, and number of catheter lumens. Ports may be used to provide physiologic access via the IV, SC, IM, intrathecal, or other routes of administration.

Manual Port Location

Ports may be generally located by palpating the skin in proximity to (e.g., over) the expected location of the implanted access port. Palpation may be used to attempt to identify which type of port has been placed and to verify expected port orientation (e.g., septum upwards towards the skin surface). Port identification may be important to ensure the type of port that has been implanted is appropriate for the planned infusion and the correct needle assembly can be selected. The size, shape, and other tactile markers on the port (e.g., protrusions on port outer housing or septa, depressions on port septa) may also be used to distinguish the type of port that has been implanted. Patients may be instructed to carry a port identification card or band detailing the type of implanted port they have, when it was placed, and by whom it was placed (e.g., individual clinician or healthcare facility).

For example, U.S. Pat. No. 8,608,713 to Beasley et al. and U.S. Pat. No. 10,052,471 to Hamatake et al. describe protrusions on the septum of an access port for palpation and identifying the access port. However, protrusions may not be intuitive for all users, and/or may lead to erosion of the site and necessitate removal of an access port. Moreover, palpation may be insufficiently precise to identify a specific port position or misconfiguration. For example, it may be limited by the tactile acuity and experience of the performing person. Thus, while palpation is useful for healthcare providers with specific training on implanted port access, variation in ability to differentiate port shapes, profiles, or orientations may still exist.

Further, lay-people, including patients and their caregivers, may lack expertise to locate and access ports, discern between port types, and identify potential complications associated with implanted ports. This may be particularly problematic when medication delivery occurs at home.

To supplement palpation, or when tactile acuity is not sufficient to identify the port, or when complications related to the port are suspected, radiologic imaging may be used to visualize the port and discern the type of port, optionally using additional identifiers provided in the access port to aid such imaging studies. Physical complications associated with the port that are difficult to detect with palpation alone may also be identified through imaging studies.

Physical complications may include port positioning, such as inversion or rotation (e.g., secondary to patient manipulation or "twiddler's syndrome") dislodgment of the catheter from the portal body, or fracture of the portal body or catheter. Inversion may refer to the port being flipped, with the septum surface not facing outwards towards the skin as expected, but inwards towards the body cavity.

Skin & Site Preparation

Once the port has been located, identified, and any complications (e.g., port inversion) have been excluded, the skin in proximity to the access port may be prepared. Optional preparation steps may reduce skin or soft tissue discomfort during later insertion of an access needle. A topical anesthetic (e.g., a cream containing lidocaine and prilocaine) may be applied to the skin, or a local injection (e.g., lidocaine) may be made to the skin or subcutaneous tissues in proximity to the access port. Such steps may be based on patient and/or clinician preference or the protocol in an administration setting.

While local anesthetics are optionally used, the skin in proximity to an access port may be routinely and diligently sterilized prior to port access. Regardless of administration setting, route of administration, or implantable port design used, maintenance of aseptic technique may be important throughout the process. For example, with an IV access port, poor aseptic technique may cause contamination of an IV line with undesired or harmful microorganisms. Such central line-associated blood stream infections (CLABSIs) may be life-threatening and require acute, intensive antibiotic treatment or removal of the access port, interrupting therapy and eliminating a crucial means of IV access, especially for patients with chronic illness. Similarly adverse sequalae may result from contamination of an SC access port. As ports are accessed for extended duration, sterilants may be selected for persistently antimicrobial activity, for example, chlorhexidine gluconate.

Port Access & Medication Administration

To deliver medications to a patient with an implanted access port, a needle and tubing set may be used. One end of the tubing set assembly may be provided with a non-coring needle, such as a Huber needle, which may be designed to prevent damage to the septum during insertion and removal. Huber needles may refer to hollow-bore percutaneous needles with a bent cannula and deflected, sharpened end to enter a port septum without coring. The bent cannula and deflected point design may preserve the self-sealing nature of the septum as a sterile and fluidic barrier when the needle is removed from the septum. Clamps may be provided on the tubing set to start or stop fluid flow. Flexible wings, if provided, may aid grasping the relatively small needle assembly and accurately placing it into the septum. The opposite end of the tubing set assembly may be generally provided with a luer taper or Luer-Lok® fitting for connection to a fluid delivery system, such as pumps common to inpatient and outpatient settings.

One end of the tubing set assembly may be connected to a medication reservoir, such as a syringe or IV extension set. Using aseptic technique, the needle may be placed over the skin covering the port septum, then advanced through the skin, subcutaneous tissue, and port septum in sequence, thereby placing the tubing set in fluidic communication with the access port cavity and thus the patient's venous system. The needle assembly may be secured with an occlusive dressing to prevent inadvertent movement, dislodgement, and contamination. Placed and secured, medication may be administered to a patient. Once administration is complete, the process may be reversed; the needle securement is removed, and the needle is withdrawn from port septum of an access port and the patient skin, allowing both layers to self-seal and re-establishing an effective barrier to contamination. As the exposed needle has been in fluidic communication with a patient's blood, some needle designs may include a protective mechanism to avoid injury from a potentially contaminated needle point during or after removal from the septum or skin.

While accessing an implanted port may be quite straightforward conceptually, the process of locating the port and preparing the port for access may be complex and technique sensitive. Limitations of related art devices currently confine port location, skin inspection, skin preparation, port access, and medication delivery to those with healthcare training. These steps may be overwhelming for patients without this training, as well as their non-clinical caregivers. As a result, many patients who may benefit from therapy with an access port cannot do so.

There is a need for improved systems, methods, and apparatus to allow a less-trained user, such as a patient or a non-clinical patient caregiver, to locate an implanted port simply and intuitively. There is also a need for improved systems, methods, and apparatus to allow a less-trained user, such as a patient or a non-clinical patient caregiver, to reliably sanitize the port, aseptically access the port, and administer one or more medications, as with a needle of a drug delivery apparatus. Such improvements may allow patients to assume more responsibility for their own care without sacrificing safety or medication efficacy. Further, such improvements may allow a broader range of patients to benefit from the use of access ports and may allow treatment of a wider range of diseases more conveniently and in less burdensome settings, such as the home setting.

SUMMARY

In some aspects, the techniques described herein relate to an apparatus for use with an access port implanted in a living body, the apparatus including: a locator assembly including: a sensor configured to sense an aspect of the access port, wherein the aspect includes at least two different material densities of the access port; a controller configured to determine a location of the access port based on differentiating the at least two different material densities of the access port, wherein the at least two different material densities correspond to at least two different elements of the access port including at least one of a port housing or an elastomeric pierceable port septum; and an output device configured to provide feedback to a user, wherein the controller is further configured to instruct the output device to provide the feedback to the user based on the determined location of the access port.

In some aspects, the techniques described herein relate to an apparatus, wherein the access port is a subcutaneous access port.

In some aspects, the techniques described herein relate to an apparatus, wherein the access port is structured to deliver medication either subcutaneously or intravenously.

In some aspects, the techniques described herein relate to an apparatus, wherein the sensor includes a plurality of ultrasonic (UT) sensors.

In some aspects, the techniques described herein relate to an apparatus, wherein: the sensor includes a center sensor and a plurality of peripheral sensors arranged in a concentric pattern around the center sensor; and when the locator assembly is positioned over the access port, the center sensor corresponds to the elastomeric pierceable port septum and the plurality of peripheral sensors correspond to the port housing surrounding the elastomeric pierceable port septum.

In some aspects, the techniques described herein relate to an apparatus, wherein the at least two different elements include the port housing and the elastomeric pierceable port septum, and a material of the port housing material is denser than a material of the elastomeric pierceable port septum.

In some aspects, the techniques described herein relate to an apparatus, wherein the controller is further configured to identify one or more regions of the elastomeric pierceable port septum, and wherein each of the regions corresponds to a pierceable septum connected to a discrete lumen of the access port.

In some aspects, the techniques described herein relate to an apparatus, wherein: based on the sensing from the sensor, the controller is further configured to identify an aspect of the pierceable elastomeric port septum or the port housing; and the aspect includes at least one of a geometry, a contour, or a material.

In some aspects, the techniques described herein relate to an apparatus, wherein: the controller is further configured to identify at least one of a design, a model, or a manufacturer of the access port based on the aspect of the port housing.

In some aspects, the techniques described herein relate to an apparatus, wherein the output device includes a wireless interface for communicating with a remote device, and the controller is configured to provide the determined location to the remote device via the wireless interface.

In some aspects, the techniques described herein relate to an apparatus, wherein the remote device is a smart phone device.

In some aspects, the techniques described herein relate to a system, including: the apparatus; and a non-transitory computer-readable storage medium storing instructions that, when executed by at least one processor of the remote device, include: receiving the determined location from the output device; and instructing a display of the remote device to provide the feedback in a visual form to the user.

In some aspects, the techniques described herein relate to an apparatus, wherein the feedback is at least one of tactile, visual, or audible.

In some aspects, the techniques described herein relate to an apparatus, wherein: the feedback includes directional feedback; and the controller is further structured to instruct the output device to provide the directional feedback to the user such that the directional feedback indicates both a direction of movement of the apparatus to directly overlap with the access port and a relative proximity of the access port.

In some aspects, the techniques described herein relate to an apparatus, wherein the controller is further configured to detect, based on the sensing from the sensor, an orientation of the access port below a skin of the living body.

In some aspects, the techniques described herein relate to an apparatus, wherein the controller is further structured to detect that the orientation of the access port below the skin is inverted based on determining that a bottom of the implanted access port is oriented upwards towards the skin.

In some aspects, the techniques described herein relate to an apparatus, further including: a base plate with an adhesive for adhering to a skin of the living body, wherein the locator assembly and the base plate are configured to attach and detach from each other.

In some aspects, the techniques described herein relate to an apparatus, wherein the base plate is configured to cooperate with a medication administration device.

In some aspects, the techniques described herein relate to an apparatus, wherein the sensor includes a plurality of ultrasonic sensors.

In some aspects, the techniques described herein relate to a method for locating an access port implanted in a living body, including: sensing, with a sensor of a locator assembly, an aspect of the access port, wherein the aspect includes at least two different material densities of the access port, and the at least two different material densities correspond to at least two different elements of the access port including at least one of a port housing or an elastomeric pierceable port septum; determining a location of the access port based on differentiating the at least two different material densities of the access port; and outputting, based on the determined location of the access port, feedback to a user.

In some aspects, the techniques described herein relate to a method, wherein outputting the feedback to the user includes: providing directional feedback to the user including both a direction of movement of the locator assembly to directly overlap with the access port and a relative proximity of the access port.

In some aspects, the techniques described herein relate to a method, wherein the outputting the feedback to the user includes: outputting the feedback to a remote device via a wireless interface.

In some aspects, the techniques described herein relate to a method, wherein the feedback is provided via the locator assembly, and the feedback is at least one of tactile, visual, or audible.

In some aspects, the techniques described herein relate to an apparatus for use with an access port implanted in a living body, the apparatus including: a locator assembly including: at least one port sensor configured to sense an aspect of the access port; at least one skin sensor configured to sense a proximity of the apparatus to a skin of the living body; a controller configured to determine a location of the access port based on the aspect sensed by the at least one port sensor, wherein the controller instructs the at least one port sensor to sense the aspect based on the proximity of the apparatus to the skin as sensed by the at least one skin sensor; and an output device configured to provide feedback to a user, wherein the controller is further configured to instruct the output device to provide the feedback to the user based on the determined location of the access port.

In some aspects, the techniques described herein relate to an apparatus, wherein: the controller instructs the at least one port sensor to sense the aspect at a first time interval when the at least one skin sensor indicates that the apparatus is beyond a predetermined threshold from the skin; the controller instructs the at least one port sensor to sense the aspect at a second time interval when the at least one skin sensor indicates that the apparatus is at or within the predetermined threshold from the skin; and the first time interval is slower than the second time interval.

In some aspects, the techniques described herein relate to an apparatus, wherein the predetermined threshold from the skin corresponds to a height of the access port to account for a prominence of the access port underneath the skin.

In some aspects, the techniques described herein relate to an apparatus, wherein the predetermined threshold is between 0.5 and 1.0 inches, inclusive.

In some aspects, the techniques described herein relate to an apparatus, wherein: the first and second time intervals correspond to sampling rates of the at least one port sensor; the first time interval is at or below a frequency of 500 Hz; and the second time interval is between a frequency of between 750 Hz and 1000 Hz, inclusive.

In some aspects, the techniques described herein relate to an apparatus, wherein the second time interval increases in frequency as the skin sensor indicates that a distance between the apparatus and the skin decreases.

In some aspects, the techniques described herein relate to an apparatus, wherein: the at least one skin sensor includes a capacitive sensor and a pogo pin; the capacitive sensor senses the proximity of the apparatus to the skin; and the pogo pin senses a contact with the skin.

In some aspects, the techniques described herein relate to an apparatus, wherein the at least one port sensor includes an ultrasonic sensor.

In some aspects, the techniques described herein relate to an apparatus, wherein at least one of the capacitive sensor or the pogo pin is electromagnetically shielded with a shielding element to prevent electromagnetic interference (EMI) from the pogo pin from interfering with a sensing of the capacitive sensor.

In some aspects, the techniques described herein relate to an apparatus, wherein the controller controls power to the pogo pin to sense a contact with the skin only when the proximity of the apparatus to the skin is within a predetermined threshold.

In some aspects, the techniques described herein relate to an apparatus, wherein the predetermined threshold corresponds to a height of the access port to account for a prominence of the access port underneath the skin.

In some aspects, the techniques described herein relate to an apparatus, wherein: the at least one skin sensor includes a capacitive sensor; and the apparatus includes a structure to prevent interference with a sensing of the capacitive sensor.

In some aspects, the techniques described herein relate to an apparatus, wherein the output device includes a visual indicator configured to indicate at least one of a direction or a proximity of the access port relative to the apparatus.

In some aspects, the techniques described herein relate to a method for using an access port implanted under a skin of a living body, including: sensing, with at least one skin sensor of an apparatus, a proximity to the skin; based on the proximity to the skin, instructing at least one port sensor to sense an aspect of the access port; sensing, with the at least one port sensor, the aspect of the access port; determining, by a controller, a location of the access port based on the aspect sensed by the at least one port sensor; and providing, via an output device, feedback to a user based on the determined location of the access port.

In some aspects, the techniques described herein relate to a method, wherein the sensing the proximity to the skin further includes: sensing the aspect at a first time interval when the at least one skin sensor indicates that the apparatus is beyond a predetermined threshold from the skin; and sensing the aspect at a second time interval when the at least one skin sensor indicates that the apparatus is at or within the predetermined threshold from the skin, wherein the first time interval is slower than the second time interval.

In some aspects, the techniques described herein relate to a method, wherein the predetermined threshold from the skin corresponds to a height of the access port to account for a prominence of the access port underneath the skin.

In some aspects, the techniques described herein relate to a method, wherein: the first and second time intervals correspond to sampling rates of the at least one port sensor; the first time interval is at or below a frequency of 500 Hz; and the second time interval is between a frequency of between 750 Hz and 1000 Hz, inclusive.

In some aspects, the techniques described herein relate to a method, wherein the at least one skin sensor includes a pogo pin, and the method further includes controlling power to the pogo pin to sense a contact with the skin only when the proximity of the apparatus to the skin is within a predetermined threshold.

In some aspects, the techniques described herein relate to an apparatus for use with an access port implanted subcutaneously in a living body, the apparatus including: a locator assembly including: a port sensor configured to sense an aspect of the access port; a controller configured to determine a location of the access port based on the aspect sensed by the port sensor; and an output device configured to provide feedback to a user, wherein the controller is further configured to instruct the output device to provide the feedback to the user based on the determined location of the access port, the locator assembly further including an outer housing, wherein the controller is in the outer housing, the outer housing including a device side coupler; and a base plate including: an adhesive flange configured to adhere the base plate to a skin of the living body, the adhesive flange including at least one opening; and a base coupler on the adhesive flange and including at least one opening, the base coupler configured to cooperate with the device side coupler such that the base plate is attachable and detachable from the locator assembly by cooperation of the device side coupler with the base coupler, wherein when the base plate is attached to the locator assembly, the at least one opening of the adhesive flange aligns with the at least one opening of the base coupler and the port sensor such that the port sensor senses the aspect of the access port through the at least one opening of the adhesive flange and the at least one opening of the base coupler.

In some aspects, the techniques described herein relate to an apparatus, the locator assembly further including: a skin sensor configured to sense a proximity of the apparatus to the skin through the at least one opening of the adhesive flange and the at least one opening of the base coupler.

In some aspects, the techniques described herein relate to an apparatus, wherein the skin sensor includes at least one pogo pin.

In some aspects, the techniques described herein relate to an apparatus, further including: a skin sensor configured to sense a proximity of the apparatus to the skin, wherein the skin sensor includes at least one pogo pin, and wherein the base plate includes at least one through-hole for the pogo pin to extend therethrough and sense contact with the skin of the living body.

In some aspects, the techniques described herein relate to an apparatus, wherein the base coupler is configured to cooperate with a coupler of at least one medication delivery device.

In some aspects, the techniques described herein relate to an apparatus, wherein the medication delivery device includes at least one of a needle assembly, an autoinjector, or a wearable injector.

In some aspects, the techniques described herein relate to an apparatus, wherein the device side coupler and the base coupler each have a cylindrical shape and are structured to threadedly cooperate with each other.

In some aspects, the techniques described herein relate to an apparatus, further including: a marking device structured to be placed through the opening of the base plate to mark the skin.

In some aspects, the techniques described herein relate to an apparatus, further including: a sterilizing swab structured to be placed through the opening of the base plate to sterilize skin.

In some aspects, the techniques described herein relate to an apparatus, wherein: the base coupler is made of a flexible material and includes a plurality of flexible fingers; and the device side coupler includes a protruding groove, wherein the plurality of flexible fingers and the protruding groove cooperate with each other to attach and detach the base coupler from the device side coupler.

In some aspects, the techniques described herein relate to an apparatus, wherein the plurality of flexible fingers of the base coupler is configured to cooperate with a buttress of a medication delivery device to restrict detachment of the medication delivery device from the base plate.

In some aspects, the techniques described herein relate to an apparatus, wherein the controller is further configured to determine, based on the sensed aspect of the port sensor, that the base plate has an incompatibility with the access port, and wherein the feedback further includes an indication of the incompatibility.

In some aspects, the techniques described herein relate to an apparatus, wherein the controller determines that the base plate has the incompatibility based on a determined manufacturer of the access port.

In some aspects, the techniques described herein relate to an apparatus, wherein the base coupler is configured to cooperate only with access ports manufactured by a predetermined manufacturer.

In some aspects, the techniques described herein relate to an apparatus, wherein a bottom side of the locator assembly includes a port relief area to accommodate a prominence of the access port under the skin.

In some aspects, the techniques described herein relate to an apparatus, wherein: the locator assembly includes a plurality of skin sensors; and the at least one opening of the adhesive flange includes a plurality of openings respectively corresponding to the plurality of skin sensors for the plurality of skin sensors to sense the skin therethrough.

In some aspects, the techniques described herein relate to a locator assembly for use with an access port implanted in a living body, the locator assembly including: a port sensor configured to sense an aspect of the access port; a controller configured to determine a location of the access port based on the aspect sensed by the port sensor; and an output device configured to provide feedback to a user, wherein the controller is further configured to instruct the output device to provide the feedback to the user based on the determined location of the access port, the locator assembly further including an outer housing, wherein the controller is in the outer housing, the outer housing including a device side coupler configured to attach and detach from a base coupler of a base plate.

In some aspects, the techniques described herein relate to a locator assembly, further including: a skin sensor configured to sense a proximity of the locator assembly through at least one opening of the base plate.

In some aspects, the techniques described herein relate to a locator assembly, wherein the skin sensor includes at least one pogo pin.

In some aspects, the techniques described herein relate to a locator assembly, wherein the device side coupler has a cylindrical shape and is structured to threadedly cooperate with the base coupler.

In some aspects, the techniques described herein relate to a locator assembly, wherein the device side coupler includes a protruding groove.

In some aspects, the techniques described herein relate to an apparatus for use with an access port implanted in a living body, the apparatus including: a base plate including: an adhesive flange; and a base coupler on the adhesive flange, the base coupler including an opening and an attachment configuration to attach and detach with a plurality of components including a locator assembly for locating the access port.

In some aspects, the techniques described herein relate to an apparatus, wherein the base coupler includes a threaded connection surrounding the opening.

In some aspects, the techniques described herein relate to an apparatus, wherein the attachment configuration includes a plurality of flexible fingers surrounding the opening.

In some aspects, the techniques described herein relate to an apparatus, further including: a medication administration device including a device coupler, the device coupler having a protruding groove, wherein the plurality of flexible fingers of the attachment configuration interact with the protruding groove to attach and detach the base coupler of the base plate from the device coupler of the medication administration device.

In some aspects, the techniques described herein relate to an apparatus, wherein the device coupler further includes a tapered buttress configured to insert into the opening of the base coupler when the base plate is attached to the device coupler and prevent or resist the plurality of flexible fingers from flexing inward, thereby preventing or resisting detachment of the base coupler from the device coupler.

In some aspects, the techniques described herein relate to an apparatus, wherein the adhesive flange is made of a flexible material.

In some aspects, the techniques described herein relate to an apparatus, wherein the base coupler is made of a rigid material.

In some aspects, the techniques described herein relate to an apparatus, wherein the base coupler and the adhesive flange are co-molded during manufacturing to yield an integral base plate.

In some aspects, the techniques described herein relate to an apparatus, wherein the base coupler is made of a flexible material.

In some aspects, the techniques described herein relate to an apparatus, wherein the adhesive flange includes an adhesive layer and an adhesive backing, the adhesive layer configured to adhere to a skin of the living body when the adhesive backing is removed.

In some aspects, the techniques described herein relate to an apparatus, wherein the adhesive backing is folded over to form a top half in contact with the adhesive layer and a bottom half including a pull tab for removing the adhesive backing from the adhesive layer.

In some aspects, the techniques described herein relate to an apparatus, wherein the adhesive flange including the adhesive layer and the adhesive backing includes at least one through-hole for a pogo pin to extend therethrough and sense contact with a skin of the living body.

In some aspects, the techniques described herein relate to an apparatus, wherein the adhesive flange includes an opening corresponding to the opening of the base coupler.

In some aspects, the techniques described herein relate to an apparatus, wherein the base plate includes a port relief area structured to accommodate a prominence of the access port under a skin of the living body.

In some aspects, the techniques described herein relate to a method of accessing an access port implanted in a living body, the method including: positioning a base plate over a location of the access port, wherein the base plate includes: an adhesive flange; and a base coupler on the adhesive flange, the base coupler including an opening and an attachment configuration to attach and detach with a plurality of components including a locator assembly for determining the location of the access port; and adhering the base plate over the location of the access port such that the opening of the base coupler corresponds to a pierceable elastomeric septum of the access port.

In some aspects, the techniques described herein relate to a method, wherein the adhering the base plate further includes: removing an adhesive backing from an adhesive layer of the base plate, wherein the adhesive backing is folded over to form a top half in contact with the adhesive layer and a bottom half including a pull tab for removing the adhesive backing from the adhesive layer.

In some aspects, the techniques described herein relate to a method, further including: determining, using the locator assembly, the location of the access port.

In some aspects, the techniques described herein relate to a method, further including: after adhering the base plate, detaching the base plate from the locator assembly.

In some aspects, the techniques described herein relate to a method, wherein at least one of the plurality of components is a medication administration device, and the method further includes attaching the medication administration device to the base coupler of the base plate.

In some aspects, the techniques described herein relate to a method for administering at least one drug to a patient, including: determining, with a locator assembly of an apparatus, a location of an access port under a skin of the patient; adhering a base plate of the apparatus to the skin of the patient at a location corresponding to the location of the access port; detaching the locator assembly from a base coupler of the base plate adhered to the skin; and administering, through an opening in the base plate adhered to the skin, a first drug to the patient.

In some aspects, the techniques described herein relate to a method, wherein the administering the first drug to the patient further includes: attaching a medication administration device to the base coupler, wherein the medication administration device includes a buttress structured to protrude within the opening in the base plate and restrict detachment of the medication administration device from the base coupler.

In some aspects, the techniques described herein relate to a method, wherein the administering the first drug to the patient further includes: attaching an autoinjector guide to the base coupler; and using an autoinjector with the autoinjector guide to administer the first drug to the patient through the opening in the base plate.

In some aspects, the techniques described herein relate to a method, further including: prior to the using the autoinjector, replacing a needle of a syringe with an autoinjector needle to form the autoinjector.

In some aspects, the techniques described herein relate to a method, wherein the administering the first drug to the patient further includes: attaching an injection needle assembly to the base coupler; and using the injection needle assembly to puncture, via the opening, the skin of the patient and pierce an elastomeric septum of the access port to thereby place the injection needle assembly in fluidic coupling with the access port and administer the first drug to the patient therethrough.

In some aspects, the techniques described herein relate to a method, wherein the administering the first drug to the patient further includes: attaching a wearable injector to the base coupler; and causing protrusion of a needle of the wearable injector to puncture, via the opening, the skin of the patient and pierce an elastomeric septum of the access port to thereby place the wearable injector in fluidic coupling with the access port and administer the first drug to the patient therethrough.

In some aspects, the techniques described herein relate to a method, further including: adhering a second base plate to the skin of the patient at a location adjacent to the location of the first base plate; and administering, through an opening in the second base plate, a second drug to the patient.

In some aspects, the techniques described herein relate to a method, further including: prior to administering the first drug to the patient, sterilizing the skin of the patient exposed by the opening of the base plate with a sterilizing swab.

In some aspects, the techniques described herein relate to a method for administering drugs to a patient, including: administering a first drug to the patient including attaching a first medication administration device to a base plate adhered to a skin of the patient; removing the first medication administration device from the base plate; administering a second drug to the patient including attaching a second medication administration device to the base plate adhered to the skin of the patient; removing the second medication administration device from the base plate; administering a third drug to the patient including attaching a third medication administration device to the base plate adhered to the skin of the patient; and removing the third medication administration device from the base plate, wherein the base plate includes an adhesive flange and a base coupler on the adhesive flange.

In some aspects, the techniques described herein relate to a method, wherein the first, second, and third medication administration devices are different types of medication administration devices.

In some aspects, the techniques described herein relate to a method, wherein at least one of the first, second, or third medication administration devices is attached to the base coupler of the base plate, and another at least one of the first, second, or third medication administration devices is attached to a second base coupler of the base plate.

In some aspects, the techniques described herein relate to a method, further including: administering a fourth drug to the patient including attaching a fourth medication administration device to a second base plate adhered to the skin of the patient, wherein the second base plate is adjacent to the base plate on the skin of the patient.

In some aspects, the techniques described herein relate to a method, wherein each of the first, second, and third medication administration devices is a same type of medication administration device.

In some aspects, the techniques described herein relate to a method, wherein the same type of medication administration device is at least one of an autoinjector, an injection needle assembly, or a wearable injector.

In some aspects, the techniques described herein relate to a method, wherein the first, second, and third drugs include a regimen for treating a condition of the patient.

In some aspects, the techniques described herein relate to a method, further including: determining a location of an access port under the skin of the patient; and adhering the base plate to the skin of the patient at a location corresponding to the location of the access port.

In some aspects, the techniques described herein relate to a method, wherein the base plate includes an opening extending through the adhesive flange and the base coupler, and at least one of the first, second, or third drugs is administered to the patient via the opening.

In some aspects, the techniques described herein relate to a method, wherein at least one of the first, second, or third drugs is administered to the patient subcutaneously.

In some aspects, the techniques described herein relate to an apparatus for use with an implanted access port in a living body, the apparatus including: a locator assembly including: a port sensor structured to sense an aspect of the implanted access port; a controller structured to detect a location of the implanted access port based on the aspect sensed by the port sensor; and an output device structured to provide feedback to a user, wherein the controller is further structured to instruct the output device to provide the feedback to the user based on the detected location of the implanted access port.

In some aspects, the techniques described herein relate to an apparatus, wherein the implanted access port is a subcutaneous access port.

In some aspects, the techniques described herein relate to an apparatus, wherein the implanted access port is structured to deliver medication either subcutaneously or intravenously.

In some aspects, the techniques described herein relate to an apparatus, further including: a skin sensor structured to sense a proximity of the apparatus to skin, wherein the controller instructs the port sensor to sense the aspect based on the proximity of the apparatus to the skin.

In some aspects, the techniques described herein relate to an apparatus, wherein the aspect includes different material densities of the implanted access port.

In some aspects, the techniques described herein relate to an apparatus, wherein the different material densities include a density of a material of a port housing of the implanted access port and a density of a material of a septum of the implanted access port, wherein the port housing material is denser than the septum material.

In some aspects, the techniques described herein relate to an apparatus, wherein the feedback is at least one of tactile, visual, or audible.

In some aspects, the techniques described herein relate to an apparatus, wherein the skin sensor includes an array of skin sensors, and the port sensor includes an array of port sensors.

In some aspects, the techniques described herein relate to an apparatus, wherein the controller is further structured to calibrate at least one of the port sensor or the skin sensor.

In some aspects, the techniques described herein relate to an apparatus, wherein the controller is further structured to remove outlier data provided by at least one of the port sensor or the skin sensor.

In some aspects, the techniques described herein relate to an apparatus, wherein: the controller is further structured to selectively engage at least one of the port sensor or the skin sensor at a regularly spaced time interval; and the regularly spaced time interval is at least one of: constant, configured based on a specific use of the apparatus, or shortened or lengthened in response to proximity to the implanted access port or detection of a material including the implanted access port.

In some aspects, the techniques described herein relate to an apparatus, wherein: based on the sensing of at least one of the port sensor or the skin sensor, the controller is structured to detect or differentiate one or more materials including different elements of the implanted access port; and the elements include at least one of a port housing or an elastomeric pierceable port septum.

In some aspects, the techniques described herein relate to an apparatus, wherein the controller is further structured to identify one or more regions of the elastomeric pierceable port septum, and wherein each of the regions corresponds to a pierceable septum connected to a discrete lumen of the implanted access port.

In some aspects, the techniques described herein relate to an apparatus, wherein: the controller and the port sensor are further structured to identify an aspect of the pierceable elastomeric port septum or the port housing; and the aspect includes at least one of a geometry, a contour, or a material.

In some aspects, the techniques described herein relate to an apparatus, wherein: the controller is further structured to identify at least one of a design, a model, or a manufacturer of the implanted access port based on the aspect of the port housing.

In some aspects, the techniques described herein relate to an apparatus, wherein the controller is further structured to detect, based on sensing from at least one of the port sensor or the skin sensor, an orientation of the implanted access port below the skin.

In some aspects, the techniques described herein relate to an apparatus, wherein the controller is further structured to detect that the orientation of the implanted access port below the skin is inverted based on determining that a bottom of the implanted access port is oriented upwards towards the skin.

In some aspects, the techniques described herein relate to an apparatus, wherein the controller is further structured to provide an alert using a feedback element when the controller detects at least one of a desired, undesired, or unsafe situation related to at least one of the apparatus, skin, or the implanted access port.

In some aspects, the techniques described herein relate to an apparatus, wherein the controller is further structured to provide the feedback to a separate input/output device such that the separate input/output device provides the feedback to the user in a more detailed format than the output device.

In some aspects, the techniques described herein relate to an apparatus, wherein: the feedback is directional feedback; and the controller is further structured to instruct the output device to provide the directional feedback to the user such that the directional feedback indicates a direction of movement of the apparatus to locate the implanted access port.

In some aspects, the techniques described herein relate to an apparatus, wherein the directional feedback includes two-dimensional information regarding the direction of movement.

In some aspects, the techniques described herein relate to an apparatus, wherein the directional feedback is a representation of a vector corresponding to the direction of movement.

In some aspects, the techniques described herein relate to an apparatus, further including: an outer housing, wherein the controller, the port sensor, and the skin sensor are in the outer housing, and wherein the controller, the port sensor, and the skin sensor are structured to detect the implanted access port by differentiating a comparatively dense port housing of the implanted access port from a comparatively less dense port septum of the implanted access port.

In some aspects, the techniques described herein relate to an apparatus, wherein the controller and the array of port sensors are structured to compute a relative position of the apparatus to one or more features of the implanted access port.

In some aspects, the techniques described herein relate to an apparatus, wherein the controller and the array of port sensors are structured to determine a relative position of the array of port sensors relative to the implanted access port as the user moves the apparatus over skin.

In some aspects, the techniques described herein relate to an apparatus, wherein the output device provides a change in the feedback when the controller detects a change in a relative position of the apparatus to the implanted access port.

In some aspects, the techniques described herein relate to an apparatus, wherein the controller and the array of port sensors are structured to infer that the apparatus is in proximity to the implanted access port but is not located directly over an elastomeric septum of the implanted access port.

In some aspects, the techniques described herein relate to an apparatus, wherein the controller and the array of port sensors are structured to infer that the apparatus is located directly over an elastomeric septum of the implanted access port.

In some aspects, the techniques described herein relate to an apparatus, further including: the locator assembly further including an outer housing, wherein the controller and the port sensor are in the outer housing, the outer housing including a device side coupler; a base plate including an adhesive flange; and a base coupler attached to the base plate, wherein the device side coupler and the base coupler are structured to cooperate with each other; and wherein the locator assembly and the base plate are removably connected by cooperation of the device side coupler with the base coupler.

In some aspects, the techniques described herein relate to an apparatus, wherein the base coupler is structured to cooperate with a coupler of one or more medical administration components.

In some aspects, the techniques described herein relate to an apparatus, wherein the device side coupler and the base coupler each have a cylindrical shape and are structured to threadedly cooperate with each other.

In some aspects, the techniques described herein relate to an apparatus, wherein the base coupler is structured to correspond to a pierceable elastomeric portion of the implanted access port when the apparatus is directly over the implanted access port.

In some aspects, the techniques described herein relate to an apparatus, wherein the one or more medical administration components includes a medication delivery device.

In some aspects, the techniques described herein relate to an apparatus, wherein the medication delivery device includes at least one of a needle assembly, an autoinjector, or a wearable injector.

In some aspects, the techniques described herein relate to an apparatus, further including: the base plate including an opening structured to correspond to a pierceable elastomeric portion of the implanted access port.

In some aspects, the techniques described herein relate to an apparatus, wherein the opening is structured to provide access to the pierceable elastomeric portion of the implanted access port with a medication delivery device.

In some aspects, the techniques described herein relate to an apparatus, wherein the base coupler is structured to attach to the medication delivery device.

In some aspects, the techniques described herein relate to an apparatus, wherein the medication delivery device accesses the pierceable elastomeric portion of the implanted access port without attaching to the base coupler.

In some aspects, the techniques described herein relate to an apparatus, wherein the base coupler is selected based on a medication delivery device.

In some aspects, the techniques described herein relate to an apparatus, wherein the opening is structured to allow insertion of a component having a shape corresponding to a shape of the opening.

In some aspects, the techniques described herein relate to an apparatus, wherein the component at least one of prepares skin, sterilizes the skin, or marks the skin.

In some aspects, the techniques described herein relate to an apparatus, further including: the one or more medical administration components.

In some aspects, the techniques described herein relate to an apparatus, further including: a marking device structured to be placed through the opening of the base plate to mark skin.

In some aspects, the techniques described herein relate to an apparatus, further including: a sterilizing swab structured to be placed through the opening of the base plate to sterilize skin.

In some aspects, the techniques described herein relate to a method for administering medication to a patient, including: locating a implanted access port under a skin of the patient using an apparatus including a base plate and a locator assembly having a sensor, a controller, and an output device; adhering the base plate to the skin of the patient over the implanted access port; removing the locator assembly from the base plate by disconnecting a device side coupler included in the locator assembly from a base side coupler included in the base plate; attaching a medication delivery device to the base side coupler such that the medication delivery device is over an opening of the base plate to access the implanted access port under the skin of the patient; and administering a medication to the patient through the implanted access port by using the medication delivery device.

In some aspects, the techniques described herein relate to a method, wherein the medication delivery device includes an injection needle assembly, the implanted access port includes an elastomeric septum, and administering the medication to the patient further includes: puncturing the skin of the patient and the elastomeric septum with a needle included in the injection needle assembly to thereby place the injection needle assembly in fluidic communication with the implanted access port.

In some aspects, the techniques described herein relate to a method, wherein attaching the medication delivery device to the base side coupler unlocks the injection needle to allow the injection needle to be advanced into the skin of the patient.

In some aspects, the techniques described herein relate to a method, wherein the medication delivery device is a wearable injector, and the method further includes: removing an adhesive from the wearable injector; providing a coupler on the wearable injector; and attaching the wearable injector to the base plate using the coupler on the wearable injector and the base side coupler.

In some aspects, the techniques described herein relate to a method, wherein the medication delivery device is a handheld autoinjector structured to be used with an autoinjector guide.

In some aspects, the techniques described herein relate to a method, wherein attaching the medication delivery device to the base side coupler further includes: attaching the autoinjector guide to the base side coupler.

In some aspects, the techniques described herein relate to a method, wherein administering the medication to the patient further includes: inserting the handheld autoinjector into the autoinjector guide to dispose a needle over the skin exposed by the opening of the opening of the base plate; and puncturing the skin of the patient with the needle of the handheld autoinjector to thereby place the handheld autoinjector in fluidic communication with the implanted access port.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE DRAWINGS

The disclosure and the following detailed description of certain embodiments thereof may be understood by reference to the following figures:

FIGS. 1A-1 and 1A-2 are cross-sectional views of examples of effectuating intravenous medication delivery using an implanted vascular access port in a patient according to example embodiments.

FIGS. 1C-1 and 1C-2 are perspective views of example implanted vascular access devices with single and double lumen configurations, respectively.

FIG. 2 is a schematic block diagram of a port locating assembly, components, and sensors, according to an example embodiment.

FIGS. 4A-1, 4A-2, and 4A-3 illustrate an exploded perspective, top, and bottom view, respectively, of a locating assembly in accordance with an example embodiment.

FIGS. 4A-4A and 4A-4B illustrate cutaway views taken through 4A-4A and 4A-4B of FIG. 4A-2, showing cross sections of a locating assembly in accordance with example embodiments.

FIGS. 4A-5A and 4A-5B illustrate cutaway views taken through 4A-4A and 4A-4B of FIG. 4A-2, showing cross sections of a locating assembly in accordance with example embodiments.

FIGS. 4B-1 and 4B-2 illustrate perspective views of handheld locating assemblies according to example embodiments.

FIGS. 4C-1A, 4C-1B, 4C-2A, 4C-2B, 4C-2C, 4C-3A, and 4C-3B illustrate top views of locating assemblies with various directional and locational feedback variations in accordance with example embodiments.

FIGS. 4D-1, 4D-2, 4E-1, 4E-2, and 4F illustrate cutaway views of a locating assembly in relationship to the skin and implanted access port in accordance with example embodiments.

FIG. 5A is an exploded assembly view of the components of a port locating assembly contained in an outer housing comprising a port locating apparatus in accordance with an example embodiment.

FIG. 5B is a partial side sectional view of components in a port locating apparatus, the apparatus also assembled and shown in relationship to an implanted port, both in accordance with an example embodiment.

FIGS. 5C-1 to 5C-4 are partial top views of a base plate in accordance with example embodiments.

FIGS. 5D-1 to 5D-3 are perspective views of a port locating apparatus shown in three progressive stages of removal after location of an implanted port, all in accordance with example embodiments.

FIG. 5H-1 is a bottom view of a base plate with adhesive layer and adhesive backing in accordance with example embodiments.

FIG. 5H-2 is a cross-section view of an adhesive layer and an adhesive backing in accordance with example embodiments.

FIGS. 6A-1 and 6A-2 are partial cutaway views of a skin sterilization or preparation step in conjunction with a base plate, all in accordance with example embodiments.

FIGS. 6B-1 and 6B-2 are partial cutaway views of a skin marking step indicating the location of an implanted port in conjunction with a base plate, all in accordance with example embodiments.

FIGS. 7B-1 to 7B-3 illustrate perspective views of a needle assembly shown in relationship to implanted port, all in accordance with example embodiments.

FIGS. 7C-1 to 7C-2 are cutaway views of a needle assembly in relationship to an implanted port, illustrating penetration of a medication delivery needle into an implanted port, all in accordance with example embodiments.

FIGS. 8B-1, 8B-2, and 8B-3 are perspective views of a wearable injector for use with a retained base plate in accordance with example embodiments.

FIGS. 8C-1 and 8C-2 are perspective partial cutaway views of a wearable injector in relationship to a retained base plate over an implanted access port, all in accordance with an example embodiment.

FIGS. 8D-1A and 8D-2 are cutaway views of a wearable injector installed on a retained base plate before and during medication delivery to an implanted access port, and FIG. 8D-1B is a close-up view of a portion of FIG. 8D-1A, all in accordance with an example embodiment.

FIGS. 9E-1 and 9F-1 are perspective partial cutaway views of an autoinjector in relationship to a retained base plate over an implanted access port, all in accordance with an example embodiment.

FIGS. 9E-2 and 9F-2 are cutaway side views showing assembly of an autoinjector into a retained base plate over an implanted access port and device adapter and subsequent medication delivery, all in accordance with an example embodiment.

DETAILED DESCRIPTION

For the purposes of clearly, concisely and exactly describing non-limiting exemplary embodiments of the disclosure, the manner and process of making and using the same, and to enable the practice, making and use of the same, reference will now be made to certain exemplary embodiments, including those illustrated in the figures, and specific language will be used to describe the same. It shall nevertheless be understood that no limitation of the scope of the present disclosure is thereby created, and that the present disclosure includes and protects such alterations, modifications, and further applications of the exemplary embodiments as would occur to one skilled in the art with the benefit of the present disclosure.

Example Access Ports

Figure 1A:
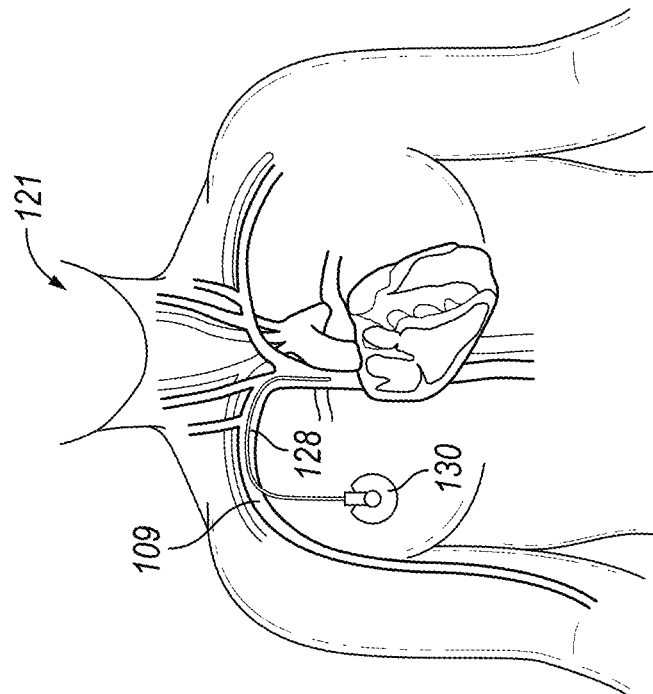
FIG. 1A shows a simplified partial cutaway front view diagram showing an anatomic location of patient interface components to effectuate intravenous medication delivery using an example implanted vascular access port.
Figures 1, 1A:
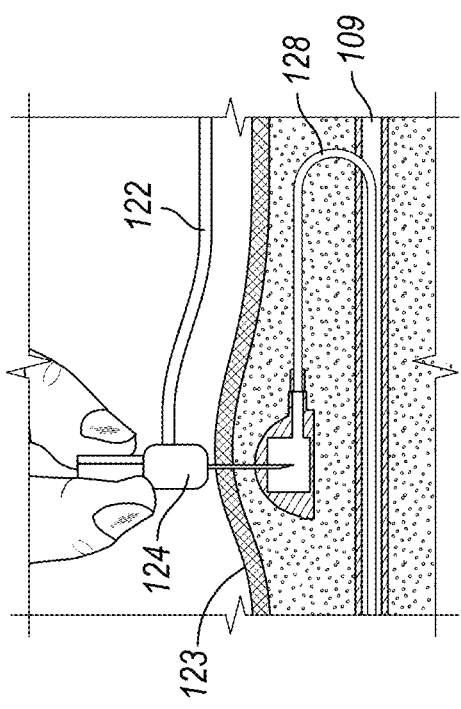
Figures 1, 1A, 2:
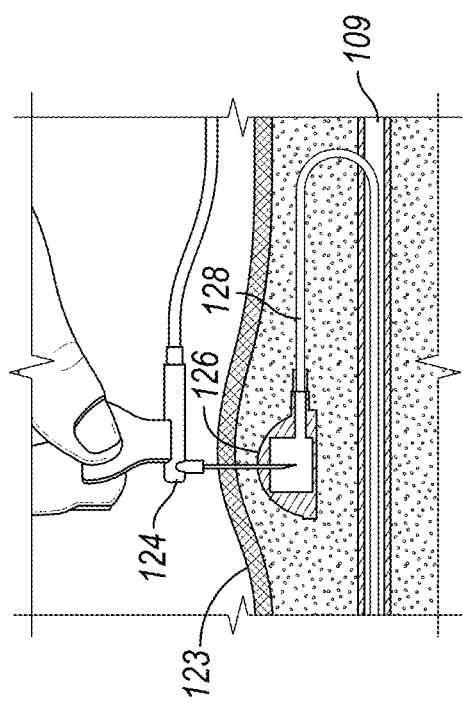
Figure 1B:
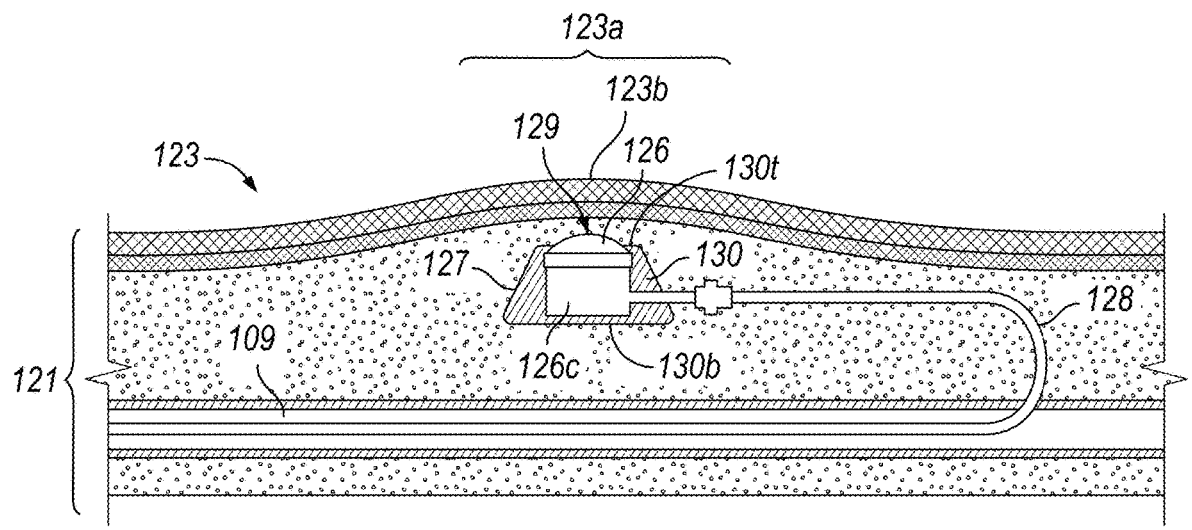
FIG. 1B shows a simplified partial cutaway diagram of an anatomic location of an example implanted vascular access port.
Figures 1, 1C:
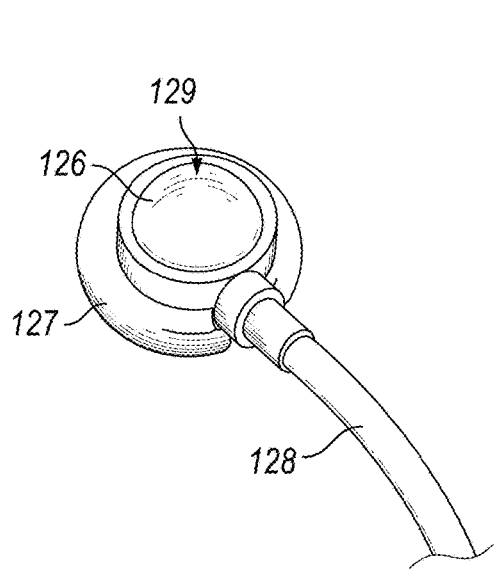
Figures 1, 1C, 2:
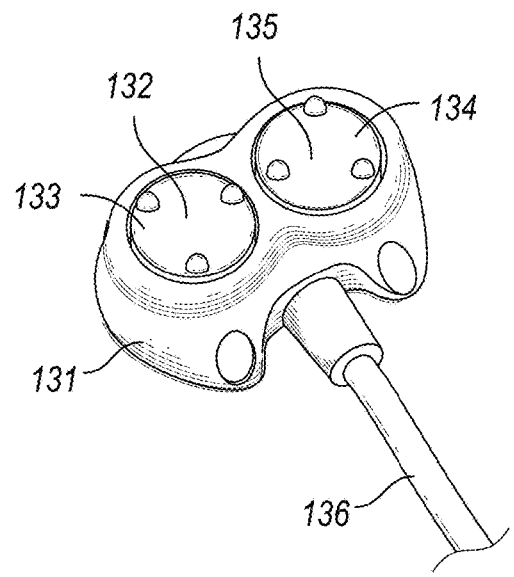
Figure 2:
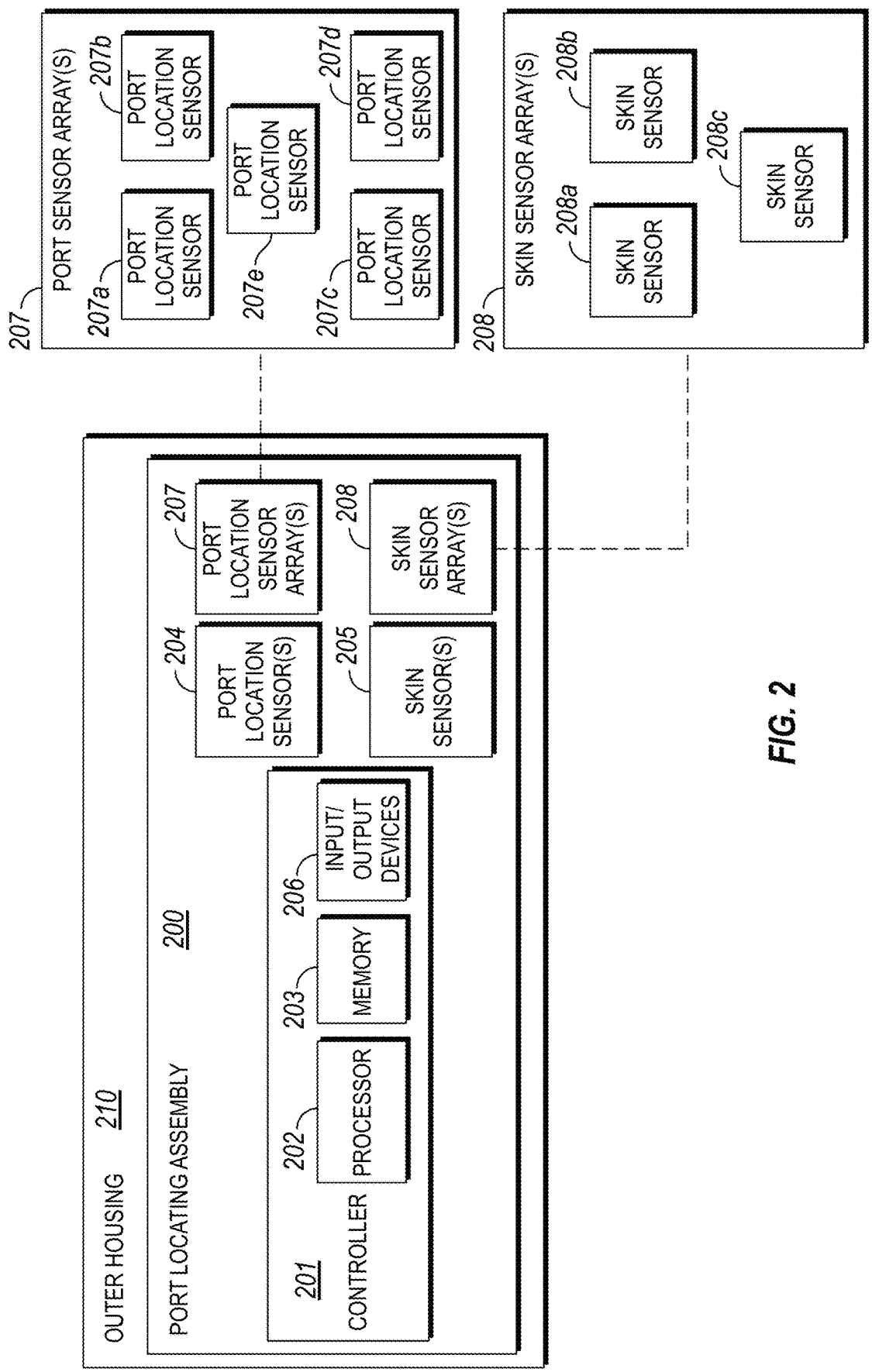

FIGS. 1A to 1C-2 show example implantable intravenous access ports to which example embodiments of the present disclosure may be directed. FIG. 1A shows a simplified partial cutaway front view diagram showing anatomic location of patient interface components to effectuate intravenous medication delivery using an example implanted vascular access device or "access port" 130 and port access needle (e.g., a hollow-bore percutaneous needle with a bent cannula and deflected, sharpened end, such as a Huber needle), and FIGS. 1A-1 and 1A-2 are partial cutaway views (also referred to herein as cross-sectional views) of effectuating intravenous medication delivery using an implanted vascular access device or port and port access needle 124 (possibly in fluidic coupling with a medication delivery tube 122) according to an example embodiment. FIG. 1B shows a simplified partial cutaway diagram of an anatomic location of an example implanted vascular access device or access port. FIGS. 1C-1 and 1C-2 are perspective views of example implanted vascular access devices with single and double lumen configurations.

The present disclosure is not limited to the example port designs and variations described herein. Although an intravenous access port 130 is shown by example in FIGS. 1A-1C-2, in some embodiments, access ports may comprise any implanted port used for medication delivery by any physiologic routes, such as a subcutaneous (SC) route, an intravenous (IV) route, an intrathecal route, or other routes. Example embodiments of the present disclosure may be used with access ports for any physiologic route of administration, having any port housing design, any number of septa, or other any ancillary features or affordances.

A description of the components and aspects of an example access port is presented to more comprehensively explain how example embodiments of the present disclosure may be used advantageously with a variety of access port designs.

In example embodiments, an intravenous access port 130 may be an access port that is implanted under the skin of a patient (e.g., a living body, which may be human or other animal or living organism), where "skin" may include the skin and any tissue under which an access port is implanted, such as subcutaneous tissue. Thus, in example embodiments involving a venous access port, the port may be implanted under the skin and subcutaneous tissue of the patient. Other types of ports may be implanted in different manners.

An implantable access port 130 may comprise a port housing 127 defining a cavity 126c enclosing one or more port septa 126. Cavity 126c may be fluidically connected to one or more catheters 128 (e.g., a single-lumen catheter). Implantable access port 130 may be placed surgically under the patient 121's skin 123 in the subcutaneous space, with patient skin 123 serving as a natural barrier to microbes or other contaminants. As described above, patient 121's skin 123 may include the skin itself as well as any tissue under which the access port 130 is implanted, such as subcutaneous tissue. In the case of an IV access port such as the example access port 130 of FIGS. 1A-1C, catheter 128 may be placed into fluidic communication (which may also be termed fluidic coupling) with an aspect of a patient's venous system (e.g., the superior vena cava 109) during implantation.

Port housing 127 may be made of a metal, such as medical grade stainless steel, titanium, or a polymer with or without a radiopaque additive. Port septum 126 may be made of an elastomeric material such as silicone, selected and designed to be self-sealing during and after penetration by, and after removal of, a specifically designed access needle. As illustrated in the example of FIG. 1C-2, in addition to the single lumen port described previously, one or more of the port 130, port cavity 126c, or septum 126 may be divided into two or more distinct regions, each region being separately attached to a catheter 128 or a double-lumen catheter 136, thereby providing fluidically separate communication to the superior vena cava 109, which may be desirable for specific medications or medication regimens. For example, as illustrated in FIG. 1C-2, the port housing 131 may divide the septum into a first port septum 133 and a second port septum 134, with a first needle entry point 132 in the first port septum 133, and a second needle entry point 135 in the second port septum 134.

One or more of the port housing, septum, or catheter may be designed to withstand a variety of injection pressures, and may also have other features, such as identifying markings or shapes, palpation bumps, retaining rings or collars, or other components.

Example Locator Assembly—Controller

Referring now to FIG. 2, in an example embodiment, a port locating assembly 200 may be provided in an outer housing 210, comprising one or more port location sensors 204, one or more skin sensors 205, and one or more input/output devices, any or all of which may be coupled to a controller 201. Controller 201 may comprise a processor 202 coupled to a memory 203, and input/output devices 206. These components are illustrated in block form by FIG. 2, and the various structural forms that these components may take may be detailed below in one or more example embodiments, and other structural forms will be apparent to those of ordinary skill in the art in view of the teachings herein.

Support circuits may be provided to controller 201 to provide communication between the different components of a system as described in example embodiments herein, including port location sensor 204 and skin sensor 205. Support circuits may also include amplifier or signal conditioning circuits interposed between the port location sensors and controller, or between one or more input/output devices and the controller. Controller 201 also may comprise support circuits to provide power to the different components of the system, and a power switch configured to supply or discontinue power to the controller 201 and/or port locating assembly 200.

The controller 201 as well as the other components of the port locating assembly 200 may be powered by internal or external means, such as a battery, inductive coupling, external cabling, kinetic motion, kinetic energy harvesting, or other power source. In some embodiments, due to the availability and/or environmental impact of battery materials such as lithium or nickel-metal hydride, and such as when the port locating assembly 200 is designed to be disposable, the port locating assembly 200 and its power supply may be designed to use (e.g., through careful power management and/or low power consumption) disposable batteries such as alkaline batteries (e.g., AA or AAA cell batteries), since such batteries may be disposed of as normal trash. Indeed, through various power management techniques as may be described herein, such as with regard to sensor sampling rates, example embodiments may use disposable batteries, and some example embodiments of the apparatus itself may be disposable. However, embodiments are not limited thereto, and in some embodiments, the power supply may be designed to use rechargeable batteries (e.g., lithium or nickel-metal hydride), such as, but not limited to, examples where the apparatus including port locating assembly 200 is designed to be reusable.

Memory 203 may include any volatile or non-volatile media, such as random-access memory (RAM), read-only memory (ROM), non-volatile RAM (NVRAM), electronically erasable programmable ROM (EEPROM), flash memory, and the like. Memory 203 may include separate memory portions for storing instructions, device serialization or unique device identifier (UDI) data, lot code or expiration information, data corresponding to different implantable ports locatable by the apparatus, data corresponding to different materials used to construct implantable ports (e.g., implanted access port 130), patient information, or other data that may benefit from separate memory modules.

In example embodiments, memory 203 may be a non-transitory computer readable storage medium storing instructions for execution by, e.g., the processor 202. In example embodiments, processes to operate the system may be stored in the memory 203. For example, the processes may be stored in the memory 203 as a software routine that, when executed by the processor 202, causes the system to perform methods according to example embodiments as described in the present disclosure. In example embodiments, some or all of the processes to operate the system may be performed in hardware. In example embodiments, the processes to operate the system may be performed by processor 202, which may include one or more processors including one or more microprocessors, digital signal processors (DSP), application specific integrated circuits (ASIC), software on a chip (SOC), or integrated circuit (IC) components. The processor may generally refer to other logic circuitry or equivalent circuitry; alternatively, the processor may be provided by a hardware device and embodied as software, firmware, hardware, or any combination thereof. In example embodiments, the software routine to operate the system may also be stored and/or executed by a second processor that is remotely located from the hardware being controlled by the processor. In some embodiments, the second processor may comprise a cloud computing service, cloud server, or mobile computing device. A mobile computing device may be any of a variety of appropriate computing devices, such as a smartphone, tablet computing device, wearable computing device, smartwatch, fitness tracker, laptop or desktop computer, or other appropriate computing device.

Any or all of port sensors 204, skin sensors 205, and input/output devices 206 may be coupled to controller 201 through a wired connection, wireless connection, or a combination thereof. Wireless connection may comprise, for example, Bluetooth, Bluetooth Low Energy (BLE), WiFi, cellular, ZigBee, near-field communication (NFC), ultrasonic communication, infrared communication, other suitable RF connection technology, or other wireless connection technology. A wired connection may comprise, for example, a universal serial bus (USB), serial connection, I2C connection, ethernet connection, other wiring, or other structured cabling.

One or more input/output devices 206 may comprise a network controller or interface to a remote computer system. The networking interface may be an internet (such as the Internet), intranet, local area network, wide area network, virtual private network, wireless network, cellular data network, or combinations thereof. In example embodiments, the controller 201 and memory 203 may store locally one or more inputs from the sensors or input/output devices when the network interface is unavailable (e.g., in the absence of intranet, internet, cellular, Bluetooth, Zigbee, WiFi, or other signal).

In some embodiments, an input/output device 206 may comprise a visual, tactile (e.g., vibration), or audible signal displayed or presented on a smart watch or smartphone display, the smart watch or smartphone also being coupled to the controller 201 by way of the connections described previously.

Example Locator Assembly—Sensors

In example embodiments, at least one of the port location sensors 204 may be configured to provide data to controller 201 regarding an aspect of access port 130 implanted below the skin 123 of a patient 121. In example embodiments, at least one of the skin sensors 205 may be configured to provide data to controller 201 regarding an aspect of the port locating assembly 200 in relationship to the skin 123 of a patient 121.

Example embodiments herein may describe locating, such as locating an implanted port, which may include one or more of identifying a port component, differentiating one port component for another, identifying a port in proximity to the apparatus, identifying the distance between an aspect of a port and the apparatus, locating the outer housing of an implanted port below a patient's skin, locating a pierceable elastomeric septum of an implanted port below a patient's skin, or computing a two or three dimensional vector between a port and/or port septum and the apparatus, each of the foregoing in accordance with the different example embodiments described herein.

While example embodiments herein may be described with reference to locating an implanted port such as a subcutaneous access port, embodiments are not limited thereto. For example, some embodiments herein may be applied to locating any foreign object underneath the skin of a living body, human or animal. In some examples, such as for a subcutaneous access port, the foreign object may be in fluidic coupling with the body, but embodiments are not limited thereto.

In some embodiments, sensors 204 and 205 may be or include separate sensors or arrangements of sensors, as illustrated by port sensor array 207 and skin sensor array 208. For example, sensor(s) 204 (which may be or include a port sensor array 207) may be used to sense an aspect of a port 130, and sensor(s) 205 (which may be or include a skin sensor array 208) may be used to sense an aspect of the skin 123. In some embodiments, one or more of the sensors 204 or 205 may comprise a capacitive, inductive, ultrasonic, magnetic, optical, radiofrequency, thermal, thermopile, infrared, or other sensor, or combinations thereof. In an example, the skin sensor 205 may include capacitive or galvanic sensing. In examples where the skin sensor 205 includes capacitive sensing, the capacitive sensing may detect an increase in capacitance as the skin sensor 205 nears the skin. In examples where the skin sensor 205 includes galvanic sensing, the galvanic sensing may detect a reduction in resistance (e.g., as compared to air) as the skin sensor 205 nears the skin.

Port sensors 204 and skin sensors 205 may be selected, combined, and configured differently depending on the clinical application, anticipated implanted port(s) to be located using the apparatus, end user using the apparatus, desired sensor sampling rate, or other relevant factors. In some embodiments, amplifier or signal conditioning circuits may be interposed between one or more of the port location sensor(s) 204, skin sensor(s) 205, port sensor array 207, skin sensor array 208, input/output devices 206 and/or the controller 201.

In some embodiments, one or more of the sensors 204 or 205 may comprise electronic spring-loaded normally open or normally closed switches (e.g., where the switches themselves involve a mechanical component) provided in the form of one or more spring-loaded pins, which may also be colloquially known as "pogo pins." Pogo pins may be highly reliable and may have short enough pin strokes that it is unlikely for them to be "halfway" activated—instead, they may be either on or off. Thus, some embodiments may include a port locating assembly 200 with one or more pogo pins used as a skin sensor 205, and each pogo pin may indicate, with an on or off signal, whether or not it is in contact with the skin. In an example embodiment including skin sensor 205 with a pogo pin that is active on, the pogo pin may provide a signal (and therefore draw power) when the pogo pin is in contact with the skin and therefore pressed. In an example embodiment including a skin sensor 205 with a pogo pin that is active off, the pogo pin may provide a signal (and therefore draw power) when the pogo pin is not in contact with the skin or otherwise pressed.

In some embodiments, all or part of the pogo pins may be made of plastic or other non-magnetic material to reduce the generated electromagnetic interference (EMI) that they generate.

In some embodiments, the port locating assembly 200 may include a skin sensor 205 (including, for example, a skin sensor array 208) having one or more capacitive sensors. Parameters for the one or more capacitive sensors may include a number of antennas, a shape of the antennas, and a number of the sensors. For example, some embodiments may include a matrix of capacitive sensors with a rejection algorithm on a false positive. For example, in a matrix of four capacitive sensors, a rejection algorithm (e.g., on controller 201) may determine that sensing three of the four capacitive sensors are in contact and/or in proximity with skin may provide an accurate indication that the port locating assembly 200 is indeed in contact and/or in proximity with the skin.

In some embodiments, the port locating assembly 200 may include a port sensor 204 (including, for example, port sensor array 207) having one or more capacitive sensors, which may have parameters and operation like the matrix described above for skin sensor 205, but for sensing an aspect of an access port rather than the skin.

In some embodiments, the capacitive sensor may be used as a skin proximity sensor in addition to and/or in place of being used as a skin contact sensor. For example, in some embodiments, a capacitive sensor may be used first to detect proximity to skin, and a pogo pin may be used thereafter to detect definitive contact with the skin. With regard to detecting proximity, such proximity may be, for example, along a Z-axis relative to the skin (e.g., orthogonal to the skin), and the capacitive sensor may indicate increasing proximity as the port locating assembly 200 moves closer to the skin. Furthermore, in some embodiments where the pogo pin(s) of the skin sensor 205 are active off (e.g., normally closed), such pogo pins may normally draw power until they make contact with the skin. Thus, the port locating assembly 200 (e.g., as controlled by the controller 201) may not power the pogo pins (e.g., by controlling power via a latch or switch) to sense contact with the skin until the capacitive sensor(s) indicate that the port locating assembly 200 is in sufficiently close proximity to the skin, providing power-saving advantages thereby. For example, controller 201 may not power the pogo pin(s) until the capacitive sensor(s) indicates that the locating assembly is within an expected height of a prominence of the access port underneath the skin. Such features may provide power management improvements to limit the amount of power consumed by port locating assembly 200 and possibly allow for the locating assembly 200 to be powered by disposable (e.g., alkaline) batteries.

In some embodiments, the sampling rate of either of the port sensor 204 and/or skin sensor 205 may be increased by controller 201 as the skin sensor 205 indicates an increasing proximity to the skin (e.g., in the Z-axis) to improve detection accuracy. Likewise, the sampling rate may be decreased as the skin sensor 205 indicates a decreasing proximity to the skin. Such features may provide power management improvements while maintaining a desirable accuracy.

In some embodiments, controller 201 and memory 203 may be provided with sensor profiles associated with one or more of the sensors 204 or 205 or arrays 207 or 208. Data contained in a sensor profile may be used by controller 201 during operation of the apparatus during one or more aspects of use. For example, a sensor profile may contain data corresponding to type(s) of sensor(s) provided in the apparatus, calibration data for one or more sensors 204 or 205, sensors to be engaged by the controller 201 at various stages of operation, sensors to be engaged or disengaged when a condition is detected by the controller 201, engagement intervals or sampling rates for a sensor 204 or 205, error correction data for a sensor, or data corresponding to one or more sensors used in different conditions.

In some embodiments, outer housing 210, one or more of the sensors 204 or 205, one of the input/output devices 206, or one or more of the supporting circuits coupling sensors 204, 205, arrays 207 or 208, and input/output devices 206 to the controller 201 may be provided with shielding elements to prevent interference (e.g., electromagnetic interference or EMI), signal distortion, or spurious signals from the assembly (e.g., from movement of internal plastic or metal components in the assembly), placement of a hand upon or near locating assembly 200, movement of locating assembly 200 by the hand of a user, contact of locating assembly 200 with the skin, or external interference, such as from radio frequency energy, "noise" from other electronic devices, or other energy sources. In some embodiments, one of input/output devices 206 may comprise a sensor to detect when the locating assembly is in the hand of a user, enabling controller 201 to detect, control, or correct spurious signals from sensors 204 or 205 and/or arrays 207 or 208 caused by a user's hand being on the device. In some embodiments, such as those including capacitive sensors, the apparatus (e.g., the locating assembly 200 or a base plate as described herein) may include a structure such as a side flange or lip around the capacitive sensors to avoid misreads from a user gripping the port locating assembly 200—such as from fingers overhanging along the bottom side of the port locating assembly 200 and/or contacting the capacitive sensor and interfering with a sensing thereof. For example, such a structure may prevent a user's fingers from covering up and/or coming too close to the capacitive sensor.

Shielding elements may include, for example, ferrite beads, ferrite plate or sheet, metal foil or mesh, or other appropriate shield materials. Sensors 204 or 205 may be shielded individually or as a part of a subassembly of the apparatus. For example, in an example embodiment including both capacitive sensors and pogo pins, the pogo pins and/or capacitive sensors may be shielded (e.g., with a shielding element) to prevent electromagnetic interference produced from mechanical movement of the pogo pins therefrom from influencing the capacitive sensors. The size and shape of shielding elements may be selected based on the types of sensors selected, the placement of sensors 204 or 205, the presence and nature of input/output devices 206, the configuration and materials in outer housing 210 (if provided), the nature of expected interference, and desired sensitivity and accuracy of sensors 204 or 205. As an alternative or in addition to shielding sensors 204 or 205 or outer housing 210, supporting circuitry may be provided in the sensors themselves (rather than controller 201 or input/output devices 206) to produce a digital signal directly at the sensor, which may reduce the impact of interference or spurious signals on an analog signal provided to controller 201. Similarly, supporting circuitry in one or more of the sensors 204 or 205, controller 201, or input/output devices 206 may compensate for spurious signals resulting from temperature changes that may affect sensor accuracy.

The locating assembly 200 may also be supplemented with one or more sensors in addition to sensors 204, 205 and/or arrays 207, 208. Such sensors may be configured as input/output devices 206 coupled to the controller 201.

Port Sensor Arrays

In some embodiments, sensors 204 and 205 may be arranged into one or more structured sensor network or sensor arrays. Such structured arrays may simplify manufacture of the apparatus, may allow for a wide variety of port configurations to be located, improve the accuracy or precision of port location, or provide enhanced feedback on port location to a user of the apparatus. In some embodiments, the structure and/or configuration of the sensor may correspond to an aspect of an implanted port to be detected with the apparatus.

In an example embodiment, one or more port location sensors 204 may be combined into a port sensor array 207, which may comprise a plurality of sensors (e.g., 207a, 207b, 207c, 207d, 207e). In some embodiments, one or more port sensor arrays 207, singularly or in combination, may provide data to controller 201 to locate an aspect of access port 130 implanted below the skin 123 of a patient 121. Also in an example embodiment, one or more skin location sensors 205 may be combined into a skin sensor array 208 comprising a plurality of sensors (e.g., 208a, 208b, 208c, 208d, 208e). In some embodiments, one or more skin sensor arrays 208, singularly or in combination, may provide data to controller 201 corresponding to an aspect of the skin 123 of a patient 121 with an implanted access port 130. In some embodiments, the skin sensors (e.g., skin sensors 308a, 308b, 308c, 308d) may be concentric with the peripheral port location sensors (e.g., peripheral port location sensors 307a, 307b, 307c, 307d) and/or the peripheral port location sensors may be located outside the periphery of the skin sensors relative to, e.g., a center such as may be indicated by center sensor 307e. In some embodiments, center sensor 307e may be a port location sensor, although embodiments are not limited thereto, and in some embodiments, center sensor 307e may be a skin sensor. In some embodiments, the peripheral port location sensors 307a, 307b, 307c, 307d may be arranged in a concentric pattern around center sensor 307e.

The foregoing description and variations related to one or more of sensors 204 and 205 may also apply to sensors 204, 205 when they are or include respective arrays 207, 208. Thus, as with port sensors 204 and skin sensors 205, port sensor array 207 and skin sensor array 208 may be selected, combined, and configured differently depending on the clinical application, anticipated implanted port(s) to be located using the apparatus, end user using the apparatus, desired sensor sampling rate, capabilities of controller 201 and supporting circuits, or other relevant factors.

For the purposes of illustration herein, port sensor array 207, which may be configured to detect aspects of an access port 130, and skin sensor array 208, which may be configured to detect aspects of the skin 123, may be distinct arrays. However, embodiments are not limited thereto. In some embodiments, a sensor array may contain any number of sensors 204 and 205 in any desired combination and in any desired arrangement. In some embodiments, either or both of port sensor array 207 or skin sensor array 208 may comprise a structured network of one or more sensors 204 and 205 and combinations and arrangements thereof.

A sensor array as described herein may be used for a single purpose, as to detect only an aspect of the port 130 or an aspect of the skin 123, but embodiments are not limited thereto. For example, in some embodiments, functions performed by port sensor array 207 may be wholly or partially performed by skin sensor array 208. In some embodiments, functions performed by skin sensor array 208 may be wholly or partially performed by port sensor array 207. In some embodiments, either or both of port sensor array 207 and skin sensor array 208, or one or more sensors contained within arrays 207, 208, may be used to sense an aspect of both a port 130 and of the skin 123.

In an example embodiment, a port locating assembly 200 may comprise one or more port sensor arrays 207 and/or one or more skin sensor arrays 208. Such a configuration may allow for different sensors to be selected based on various states of the apparatus or various use steps of the apparatus. For example, the controller 201 may receive data from a first set of skin sensor arrays 208 configured to operate while the assembly is in contact with the skin 123, from a second set of skin sensor arrays 208 while not in contact with the skin 123, or a combination of both first and second sets when the assembly is in proximity (but not yet contacting) the skin 123.

Alternatively, in some embodiments, the controller 201 may receive data from a first set of port sensor arrays 207 configured to operate while the outer housing is in proximity to a located implanted port, from a second set of port sensor arrays 207 while the outer housing is not in proximity to a located implanted port, or from a combination of both first and second port sensor arrays. In the foregoing example, controller 201 may also be optionally configured to receive data from either or both of the port sensors 204 or the skin sensors 205 during use of any of the skin sensor arrays or port sensor arrays.

Use of Sensors

In some embodiments, controller 201 may implement a calibration process for one or more of sensors 204, 205, port sensor arrays 207, or skin sensor arrays 208 to ensure correct data is received by the controller 201, to correct data received by the controller 201 for the use context, or to avoid interference (e.g., by other sensors). In some embodiments, controller 201 may be configured to remove outlier data provided by one or more of sensors 204, 205, port sensor arrays 207, or skin sensor arrays 208. In an example embodiment, the controller 201 may be configured to receive and compare data from one or more sensors 204, 205, 207, 208, and discard or disregard outlier data.

In an example embodiment, sensors 204, 205, port sensor arrays 207, or skin sensor arrays 208 may be selectively engaged (e.g., energized, sampled, polled, or interrogated) by the controller 201 at one or more regularly spaced intervals. A regularly spaced interval may remain constant throughout use of the apparatus (e.g., 500 Hz for a capacitive sensor), a plurality of regularly spaced intervals may be configured based on a specific use step of the apparatus (e.g., 200 Hz for a capacitive sensor while comparatively far from the skin initially, then 500 Hz for the capacitive sensor as proximity to the skin increases), or a regularly spaced interval may be shortened or lengthened in response to proximity to a port, or detection of one or more materials comprising the port (e.g., 500 Hz while comparatively far from the port, then a fixed higher frequency or an increasing range of, e.g., between 750 to 1000 Hz, inclusive, as proximity to the port progressively increases).

For example, in some embodiments, the sensors 204, 205, port sensor arrays 207, or skin sensor arrays 208 may be engaged at a lower frequently (e.g., 500 Hz for a capacitive sensor, which may be described as a slower time interval) when the controller 201 determines that the port locating assembly 200 is further than a predetermined threshold away from the skin, such as an inch away, and may be engaged at a higher frequency (e.g., between 750 to 1000 Hz for a capacitive sensor, which may be described as a faster time interval) when the controller 201 determines that the port locating assembly is at or below a predetermined threshold range away from the skin.

In some examples, the threshold range may correspond to (and account for) a height of a port prominence relative to the rest of the skin—for example, 0.5 to 1.0 inches away from the skin, inclusive. Indeed, in some embodiments, the threshold range may correspond to a height of a prominence of an access port to be sensed, at least insofar as the threshold range may be of a same order of magnitude as an expected height of the prominence. In some examples, the higher frequency (e.g., the sampling rate of a port sensor 204) may increase from, e.g., 750 to 1000 Hz as the controller 201 determines that the distance to the skin decreases (e.g., from 1.0 inches to 0.5 inches). In some examples, when the controller 201 determines that the port locating assembly 200 is between immediately contacting the skin and a predetermined distance away, inclusive (e.g., 0.0 inches to 0.5 inches away), the sensors (e.g., the port sensors) may be engaged at a fixed higher frequency—for example, at the upper end of the variable range, such as 1000 Hz. Such arrangements may be used to improve detection sensitivity and power management of the apparatus. In an example embodiment, a high resolution analog-to-digital conversion (ADC) may be employed (in conjunction with or independently of a varied spaced interval) to detect signal changes from one or more of sensors 204, 205, port sensor arrays 207, or skin sensor arrays 208. Use of lower sampling frequencies for the ADC at further distances may also result in a power savings.

With regard to the sampling frequencies of the sensors 204, 205, port sensor arrays 207, or skin sensor arrays 208, detection of a real signal (e.g., based on capacitance sensing) may be orders of magnitude slower than spurious signals (e.g., as may occur with capacitive sensors), and spurious signals may be identified and ignored by the controller 201 accordingly.

Thus, as described above, in some embodiments, controller 201 may be configured to engage one or more sensors 204, 205 or one or more sensor arrays 207, 208 at one or more different intervals to conserve power during one or more aspects of operating the apparatus. An aspect of operating the apparatus, for example, may comprise the presence, absence, or proximity of a user's hand on the port locating assembly 200, the proximity of the port locating assembly 200 to the skin 123, the orientation of the implanted port 130 relative to the skin surface, the orientation of the port septum 126 relative to the skin 123, the orientation of the bottom port surface 130b (see FIG. 1B) relative to the skin 123, the rate of translation or rotation of port locating assembly 200 relative to the skin 123 or access port 130, or other factors. For example, such a configuration may reflect a "low power" mode with lower fidelity, and "high power" mode with higher fidelity.

In an example embodiment, controller 201 may be configured to shorten or lengthen a regularly spaced engagement interval like as described above based on one or more conditions detected by one or more of controller 201, sensors 204, 204, or arrays 207, 208. For instance, controller 201 may engage (e.g., energize, sample, poll, or interrogate) port sensors 204 or port sensor array 207 at a first comparatively longer interval if data from skin sensor 205 or skin sensor array 208 indicates to the controller 201 that the apparatus is far from the skin. Once skin is detected by sensors 205 or skin sensor array 208 (e.g., within a threshold proximity), controller 201 may engage port sensors 204 or port sensor array 207 at a second interval comparatively shorter than the first interval to detect, and thus locate accurately, an implanted access port 130.

In an example embodiment, one or more of sensors 204 or 205, port sensor array 207, or skin sensor array 208 may singularly, or in combination, provide data to controller 201 to locate an aspect of an access port 130 implanted below the skin 123 of a patient 121.

In some embodiments, data provided to controller 201 by one or more of sensors 204 or 205, port sensor array 207, or skin sensor array 208 may include one or more of position, location, or orientation of the port beneath the skin 123 of a patient 121. Data may be provided, for example, by configuring sensors 204 or 205, port sensor array 207, or skin sensor array 208 to generate a detection signal which enters the skin, soft tissue, or components of the implanted venous port, and then providing the detection signal to the controller 201 for evaluation.

In an example embodiment, data provided to controller 201 by one or more of sensors 204 or 205, port sensor array 207, or skin sensor array 208 may also include information used to infer an aspect about the materials comprising a part of the port. For example, data may comprise information corresponding to the density of different materials used to construct one or more of port 130, outer port housing 127, or port septum 126.

In some embodiments, data provided to controller 201 by one or more of sensors 204 or 205, port sensor array 207, or skin sensor array 208 may also include the presence or absence of skin 123 of a patient 121, or the proximity of the port locating assembly 200 to the skin 123 of a patient 121.

In an example embodiment, data provided to controller 201 by one or more of sensors 204 or 205, port sensor array 207, or skin sensor array 208 may be used by controller 201 to provide feedback via one or more input/output devices 206 to a user of the locating assembly 200.

In an example embodiment, one or more of sensors 204 or 205, port sensor array 207, skin sensor array 208, or controller 201 may be configured to either detect or differentiate one or more materials comprising different aspects of an implanted port 130. In some embodiments, the different aspects may comprise areas of an implanted port 130 that are either accessible or inaccessible with a needle. For example, port sensor array 207 may be configured to identify one or more elements of port 130, such as a port housing 127 or elastomeric pierceable port septum 126.

In some embodiments, one or more of sensors 204 or 205, port sensor array 207, skin sensor array 208, or controller 201 may be configured to identify one or more materials comprising the outer port housing. For example, port sensor array 207 and controller 201 may be configured to detect certain categories of implanted ports 130 based on one or more shared characteristics, such as those with a metal, plastic, ferrous, nonferrous, or radio-opaque outer port housing 127.

In some embodiments, one or more of sensors 204 or 205, port sensor array 207, or skin sensor array 208 and controller 201 may be configured to identify one or more materials comprising a port septum 126. In some embodiments, port sensor array 207 and controller 201 may be configured to identify one or regions of elastomeric pierceable port septum 126, each of the regions corresponding to a pierceable septa connected to a discrete lumen of catheter 128 of port 130.

In some embodiments, one or more of sensors 204 or 205, port sensor array 207, or skin sensor array 208 and controller 201 may be configured to distinguish between one or more materials comprising outer port housing 127 and one or more materials comprising port septum 126. For example, port sensor array 207 and controller 201 may be configured to distinguish a portion of port housing 127 fashioned from a comparatively dense, rigid material (e.g., a polymer or metal) from a portion of septum 126 fashioned from a comparatively less dense, elastomeric (e.g., silicone) material.

In some embodiments, port sensor array 207 and controller 201 may be configured to identify one or more aspects of the geometry, contour, or materials of a pierceable elastomeric port septum 126 or outer port housing 127. In some embodiments, port sensor array 207 and controller 201 may be configured to identify the design, model, or manufacturer of an implanted port 130 based on sensor data related to geometry, contour, or materials of port 130.

In some embodiments, one or more of sensors 204 or 205, port sensor array 207, or skin sensor array 208 may be arranged to correspond to a shape of an aspect of an access port 130, such as a shape of the elastomeric port septum 126 and/or the surrounding port housing 127. For example, such an arrangement may be used when the locating assembly is designed to locate a type or manufacture of access port 130 having a specific and/or distinctive shape.

Detecting Port Orientation & Inversion

In an example embodiment, controller 201 may be configured to detect, by way of one or more of sensors 204 or 205, port sensor array 207, or skin sensor array 208, an orientation of access port 130 implanted below the skin 123 of a patient 121. Advantageously, such orientation detection may be used to distinguish proper and improper port orientation during location of an access port 130 using the apparatus, even if a user lacks clinical training or skill.

In an example embodiment, controller 201 may be configured to detect, by way of one or more of sensors 204 or 205, port sensor array 207, or skin sensor array 208, a properly oriented access port 130—e.g., an access port 130 at a normal, expected orientation whereby the access port 130 remains in the orientation at the time of port implant beneath the skin 123 of a patient 121, with port septum 126 and top of port 130*t* oriented outwardly towards the skin 123 and bottom port surface 130*b* oriented inwardly towards the interior body cavity and away from the skin 123 surface. A properly oriented access port 130 may be located, accessed, and used to deliver one or more medications to a patient. A properly located access port may be a precondition to port access and medication delivery. Similarly, an inverted access port 130 may be detected (and not used) if the bottom of port 130 is oriented upwards towards skin 123 (an inaccessible, undesirable position) and the top of port 130*t* is oriented downwards away from skin 123.

In some embodiments, port sensor 204 may include a port sensor array 207 structured to detect an aspect of an access port 130 including, for example, a comparatively dense material of a port housing and a comparatively less dense material of an elastomeric septum. For example, in some embodiments, the port sensor array 207 may include a matrix or other arrangement of sensors. For example, the port sensor array 207 may include a plurality of concentrically arranged sensors, which may be or include ultrasonic (UT) sensors. In some embodiments, the controller 201 may be configured to determine a location of the access port 130 based on differentiating the different material densities, which may correspond to at least two different elements of the access port 130, such as the port housing and the elastomeric pierceable port septum. For example, when the port sensor 204 including port sensor array 207 is located directly over a subcutaneous access port underneath the skin, an outer ring of the concentrically arranged sensors may sense the comparatively dense material of the port housing (which may, for example, include titanium or plastic), and an inner portion of the concentrically arranged sensors may sense the comparatively less dense material of the elastomeric septum. In some embodiments, the controller 201 may interpret the sensed data from the port sensor 204 including port sensor array 207 as a density map. The controller 201 may determine from this density map that the port sensor 204 is directly over the subcutaneous access port. For example, the density map may include a centered dense circle or other outline of the subcutaneous access port, which corresponds to the position of the port sensor 204 directly underneath the port sensor array 207.

In some embodiments, when the port sensor 204 including port sensor array 207 partially overlaps with the subcutaneous access port, the density map sensed from the port sensor array 207 including the concentrically arranged sensors may include only part of a dense circle or other outline of the subcutaneous access port, with an inner portion of the circle being less dense and corresponding to the elastomeric septum, while a remaining portion of the density map does not indicate anything implanted underneath the skin. The controller 201 may thus determine from the density map (including the shape of the outline) the direction in which to move in order to be directly over the subcutaneous access port.

In some embodiments, when the port sensor 204 including port sensor array 207 does not overlap with the subcutaneous access port, the density map sensed from the port sensor array 207 including the concentrically arranged sensors may not indicate anything implanted underneath the skin.

In some embodiments, instead of or in addition to the plurality of sensors comprising port sensor array 207, the port sensor 204 may rely on motion and use of one or more sensors that continuously senses when, for example, the skin sensor 205 indicates contact with the skin. For example, as the port sensor 204 moves across the skin, the one or more sensors may continuously gather sensing data, which the controller 201 may analyze to detect an edge of the subcutaneous access port and/or to form a density mapping. Like as described above, the density mapping may be used by the controller 201 to determine the location of the port sensor 204 relative to the subcutaneous access port and a direction of movement needed for the port sensor 204 to be located directly over the subcutaneous access port.

In some embodiments, the controller 201 may compare the sensed data (e.g., a density map) from the port sensor 204 to one or more references (e.g., stored in memory 203), such as one or more stored subcutaneous access port profiles, to determine the location of the port sensor 204 relative to the subcutaneous access port as well as identifying the subcutaneous access port itself (e.g., by type, model, etc.).

In some embodiments, the port sensor 204 (which may include the port sensor array 207) may include an optical sensor, which the controller 201 may use to determine a comparatively higher reflectance of a metal or plastic housing of the subcutaneous access port as compared to the lower reflectance elastomeric septum of the subcutaneous access port. Additionally, the same or a different optical sensor (or a different type of sensor, such as ultrasonic) may be used (e.g., angled) to sense reflectance of implanted objects such as an access port that are not directly underneath the port sensor 204 (e.g., off to a side), which the controller 201 may use to determine a direction of movement to place the port sensor 204 directly over the implanted object such as the subcutaneous access port.

In some embodiments, the port sensor 204 (which may include the port sensor array 207) may include an electronic spring-loaded switch (e.g., a pogo pin) and/or a mechanical palpation probe, which the controller 201 may use to detect the density of an object such as a subcutaneous access port or elastomeric septum beneath the skin.

In some embodiments, the port sensor 204 (which may include the port sensor array 207) may include different types of sensors to reduce crosstalk. For example, the port sensor array 207 may include an outer ring of ultrasonic sensors to sense the outer housing of a subcutaneous access port, while an inner sensor or sensors may include a "pogo pin" or mechanical palpation probe to sense the elastomeric septum of a subcutaneous access port.

In some embodiments, the port sensor 204 (which may include the port sensor array 207) may include a magnetic sensor, which may use eddy current detection or hall effect sensing to detect the housing (e.g., a metal housing) of a subcutaneous access port.

In some embodiments, the port sensor 204 (which may include the port sensor array 207) may include a needle (e.g., a thin needle), which the controller 201 may use to probe the skin (e.g., after the skin has been sanitized) to determine the presence or absence of an elastomeric septum underneath the skin. For example, after the port sensor 204 has determined that it is located directly over top of a subcutaneous access port, the port sensor 204 may advance the needle through the skin enough to partially pierce the elastomeric septum, thereby confirming that the elastomeric septum is underneath and ready for medical administration as described herein. Alternatively, the needle may be blunt, and the controller 201 may detect the bounceback of the needle.

In some embodiments, the subcutaneous access port itself may include one or more near-field communication ("NFC") tags for detection by the port sensor 204, which may include a sensor for detecting NFC tags. For example, the elastomeric septum of a subcutaneous access port may include four equally spaced NFC tags about its circumference, which the controller 201 may detect through port sensor 204 to determine when the port sensor 204 is directly over the elastomeric septum.

Input & Output Devices

Input/output devices 206 (which may include input devices, output devices, and devices that may both input and output) may be selected and provided based on how locating assembly 200 will be used in a particular context or situation. One or more input/output devices 206 may also be configured to operate separately or cooperatively in any combination desired, all upon instruction from the controller 201.

In an example embodiment, an input/output device 206 may comprise one or more devices configured to sense movement, rotation, or translation of the apparatus or the outer housing. For instance, input/output device 206 may comprise an inertial measurement unit (IMU), gyroscope, accelerometers, combinations thereof, or other appropriate sensors to measure various aspects of translation and/or rotation of the locating assembly 200 during use.

In an example embodiment, an input/output device 206 may comprise one or more ultraviolet (UV) radiation sources configured to cooperate with controller 201 to irradiate and thus sterilize one or more of surfaces of skin

123, 123a, 123b (see FIG. 1B) prior to accessing port 130. Input/output device 206 may emit UV radiation at one or more appropriate wavelengths of sufficient intensity and for sufficient duration to sterilize the skin surface in proximity to access port 130 after locating the port as described herein. The wavelengths, intensity, and duration of UV radiation emitted by input/output device 206 may be selected based on the skin, degree of expected skin contamination, or other relevant factors. The wavelengths, intensity, and duration of UV radiation emitted by input/output device 206 may also be designed based on one or more materials imposed between the input/output device 206 and the skin 123, 123a, 123b that may reduce the intensity or effectiveness of the UV radiation, such as adhesive layers, barrier layers, buffer layers, sterilant on the skin, or other materials.

In an example embodiment, an input/output device 206 may comprise a camera, and an input/output device 206 may comprise an illuminator, and both the camera and illuminator may be configured to communicate with and be operated by controller 201 to illuminate and subsequently identify an aspect of one or more of skin 123 surface, surface of skin 123a surrounding the implanted port 130, or surface of skin 123b at the needle insertion site.

In an example embodiment, a camera may be configured to identify one or more deleterious aspects of skin 123, skin 123a surrounding the implanted port 130, or needle entry point in the skin 123b rendering port access clinically contraindicated or unadvisable. A deleterious aspect may comprise, for example, redness, erythema, edema, swelling of the ipsilateral chest, bulging veins, irritation, seepage, weeping, drainage, bleeding, oozing, broken skin, skin necrosis, dehiscence, induration, lacerations, purulent exudates, or other skin conditions indicative of erosion or infection of the skin 123, skin 123a surrounding the implanted port 130, skin 123b at the needle insertion site, port or catheter migration, dislodgment or inappropriate placement, port or catheter occlusion or loss of patency, medication infiltration or extravasation, or systemic infection.

In an example embodiment, a camera may be configured to identify an aspect of preparation of one or more of skin 123, skin 123a surrounding the implanted port 130, or needle entry point in the skin 123b. An aspect of the skin preparation may include, for instance, the presence (or absence) of an antimicrobial, antifungal, or antiviral on the skin surface such as povidone-iodine, alcohol, chlorhexidine gluconate, polyhexamethylene biguanide, a dye contained in a skin sterilant, or an adhesive element.

An illuminator may comprise a light emitting diode (LED) of visible or nonvisible light, a multi-color red-green-blue (RGB) LED, an addressable or color changing LED, segmented LEDs, a LED matrix or panel, a LED and fiber optic assembly, a liquid crystal display, an organic electroluminescent display (OLED), an electrophoretic display, an electroluminescent (EL) panel, an EL wire, EL tape, or EL fiber, or other suitable device providing required the wavelengths and intensity of illumination to cooperate with the selected camera.

Feedback States & Indicators

One or more input/output devices 206 may be configured to provide feedback to a user of the apparatus. In some embodiments, the feedback may comprise a visible indicator produced by one or more input/output devices 206 upon instructions from the controller. The visible indicator may comprise a light source producing single or multiple colors of visible light, such as a light emitting diode (LED) of visible or nonvisible light, a multi-color red-green-blue (RGB) LED, an addressable or color changing LED, segmented LEDs, a LED matrix or panel, a LED and fiber optic assembly, a liquid crystal display, an organic electroluminescent display (OLED), an electrophoretic display, an electroluminescent (EL) panel, an EL wire, EL tape, or EL fiber, or other suitable device that will be visible to an expected user of locating assembly 200.

In some embodiments, the feedback may comprise a visible indicator produced by one or more input/output devices 206 upon instructions from the controller 201. For example, the visible indicator may partially or fully protrude from the outer housing 210 or may be visibly situated in a thinned cross section, transparent portion, or translucent diffuser provided in a portion of outer housing 210. Visible indicators may be selectively illuminated, brightened, dimmed, recolored, flashed, or pulsed. A consistent or intermittent light signals of color (e.g., red, amber, green) or intermittent light signals of color, or flashing patterns (e.g., red flashing, red-yellow pulsing, or fast or slow flashing) could be used in place of different colors.

In some embodiments, the feedback may comprise an audible indicator produced by one or more input/output devices 206 upon instructions from the controller 201. The audible indicator may comprise an audible tone, or one or more audible tones of substantially different frequencies, pitch, or repetition rates. Audible indicators may vary in frequency, amplitude, and/or waveform of vibrations to provide indications of different states or different types of information to the user based on data received by the controller 201. The audible indicator may comprise an audible tone of human speech including easily understandable feedback phrases as described further herein.

In some embodiments, the feedback may comprise a tactile indicator produced by one or more input/output devices 206 upon instructions from the controller 201. Tactile indicators may include vibratory feedback, as when input/output device 206 comprises a vibration generator or vibratory motor as in a cellular telephone, or when input/output device 206 comprises a haptic actuator. Tactile indicators may vary in frequency, amplitude, and/or waveform of vibrations to provide indications of different states or different types of information to the user based on data received by the controller 201.

In some embodiments, the selected feedback elements may be provided in combination by controller 201 corresponding to one or more states of locating assembly 200 or use steps therein. In some embodiments, feedback elements may be provided in combination by controller 201 to alert a user to one or more desired, undesired, or unsafe situation(s) related to locating assembly 200, to the skin 123, to the skin 123a surrounding the implanted port 130, to the skin 123b at the needle insertion site, to the access port 130 itself, to the port housing 127, to the port septum 126, or to the lumen of catheter 128 of access port 130.

In addition to feedback provided on the locating assembly 200 or outer housing 210, feedback may also be provided on another input/output device 206, such as a smart watch or smart phone. This may advantageously duplicate feedback so a user may manipulate the apparatus to locate a port while viewing feedback on the phone. The feedback provided on the locating apparatus and smart watch/phone need not be identical. For example, the smart watch or smart phone may provide a more detailed format such as using a high-resolution graphical display, while the input/output device 206 on outer housing 210 may be comparatively simpler. In some embodiments, feedback provided by the input/output device 206 on the outer housing 210 may be provided in a first orientation, while feedback provided on the smart phone or smart watch may be reversed, so the direction shown on the companion device corresponds to the correct movement to locate the port. In some embodiments, the other input/output device 206 such as the smart phone or smart watch may be remote from the locating assembly. In some embodiments, an input/output device 206 or other device of the locating assembly 200 may include a wireless interface for communicating with the other input/output device 206, including providing a determined location (e.g., which may be relative to the locating assembly 200) to the other input/output device 206. In some embodiments, a system according to example embodiments may include a non-transitory computer-readable storage medium that stores instructions that, when executed by at least one processor of the another input/output device 206, may include receiving the determined location from an input/output device 206 that is included in the locating assembly 200, and instructing a display of the other input/output device 206 to provide the feedback in a visual form to a user.

Directional & Locational Feedback

In some embodiments, directional feedback may be provided to a user indicating a proposed direction of movement of locating assembly 200 to locate access port 130. Thus, in some embodiments, the controller 201 may instruct the directional feedback based on a determined location of the access port 130 relative to the locating assembly 200. In some embodiments, directional feedback may provide two-dimensional information (e.g., left, right, up, down, etc.) to a user regarding the position of the locating assembly 200 in relation to access port 130. For example, the directional feedback may be a representation of a vector corresponding to a proposed direction of movement of the locating assembly 200 to position it in closer proximity to access port 130. In some embodiments, directional feedback may be based on data from one or more of sensors 204 or 205, port sensor array 207, or skin sensor array 208.

In some embodiments, directional feedback may be provided to a user indicating a proposed translation or rotation of locating assembly 200 generally towards implanted access port 130, towards closer proximity to the port 130, over the outer port housing 127, or over a pierceable portion (or the center) of the port septum 126. As such, in an example embodiment, as the distance between locating assembly 200 and the port 130 (e.g., relative proximity) decreases, the visual feedback may be flashed in increasing frequency and amplitude. Conversely, as the distance between locating assembly 200 and the port 130 increases, the visual feedback may be flashed in decreasing frequency and amplitude or may remain continuously illuminated.

In an example embodiment, as the distance between the locating assembly 200 and the port 130 decreases, the audible feedback may increase in frequency and amplitude. Conversely, as the distance between the locating assembly and the port increases, the audible feedback may decrease in either or both of frequency and amplitude.

In an example embodiment, as the distance between the locating assembly 200 and the port 130 decreases, the audible feedback may comprise audible tones of human speech such as "you're getting closer to the port" or "you're nearing the port." Conversely, as the distance between the locating assembly and the port increases, the audible feedback may comprise audible tones of human speech such as "you're still on the skin," or "you're moving away from the port." In some embodiments, the audible feedback may comprise audible tones of human speech indicating directional guidance to position the locating assembly 200 relative to the port 130 (e.g., "keep moving to the left," "move a bit to the right," "move down," or "move up and to the left").

In an example embodiment, as the distance between the locating assembly 200 and the port 130 decreases, the vibratory feedback may increase in frequency and amplitude. Conversely, as the distance between the locating assembly 200 and the port 130 increases, the vibratory feedback may decrease in frequency and amplitude.

In some embodiments, directional feedback may provide information to a user regarding the position of the locating assembly 200 in relation to one or more of the patient's skin 123, skin 123a surrounding the port, or needle entry point in skin 123b. In some embodiments, the audible feedback may comprise an easily understood phrase indicating feedback about the relationship of the apparatus to the skin, or a proposed direction of moment of the locator assembly relative to the skin, such as "hold the device against or near the skin," "keep the device a bit further from the skin," or "try to keep the device flat to the skin if you can".

In some embodiments, feedback may be provided to a user of the locating apparatus when the locating assembly 200 is substantially centered over the center of the septum of a port 130. The feedback may include visibly rapidly flashing light or an audible rapidly oscillating frequency or vibrations. Alternatively, if the locating assembly is over the port, the audible feedback may comprise an easily understood phrase such as "you're directly over the port."

Error State Feedback

In some embodiments, the visual feedback may alternate in frequency and/or amplitude if an unsafe or undesirable condition is detected. In some embodiments, the audible feedback may alternate in frequency and/or amplitude if an unsafe or undesirable condition is detected. In some embodiments, the vibratory feedback may alternate or increase in frequency and/or amplitude if an unsafe or undesirable condition is detected. In some embodiments, the unsafe condition may correspond to an inverted port as described herein.

In some embodiments, the locating assembly 200 may perform an initial calibration before locating the port 130 or providing feedback to a user of the apparatus. When a user first places locating assembly 200 against or in proximity of skin 123, the locating assembly 200 may have no knowledge of whether it is over the implanted port 130 or a portion thereof. In some embodiments, if controller 201 detects, as via sensors 204 or 205, port sensor array 207, or skin sensor array 208, that the locating assembly 200 is over the port 130, or possibly over the port 130, the controller 201 may provide feedback to a user to start over, placing the locating assembly 200 in a different initial position.

Implanted Port Detection—Method

Figure 3A:
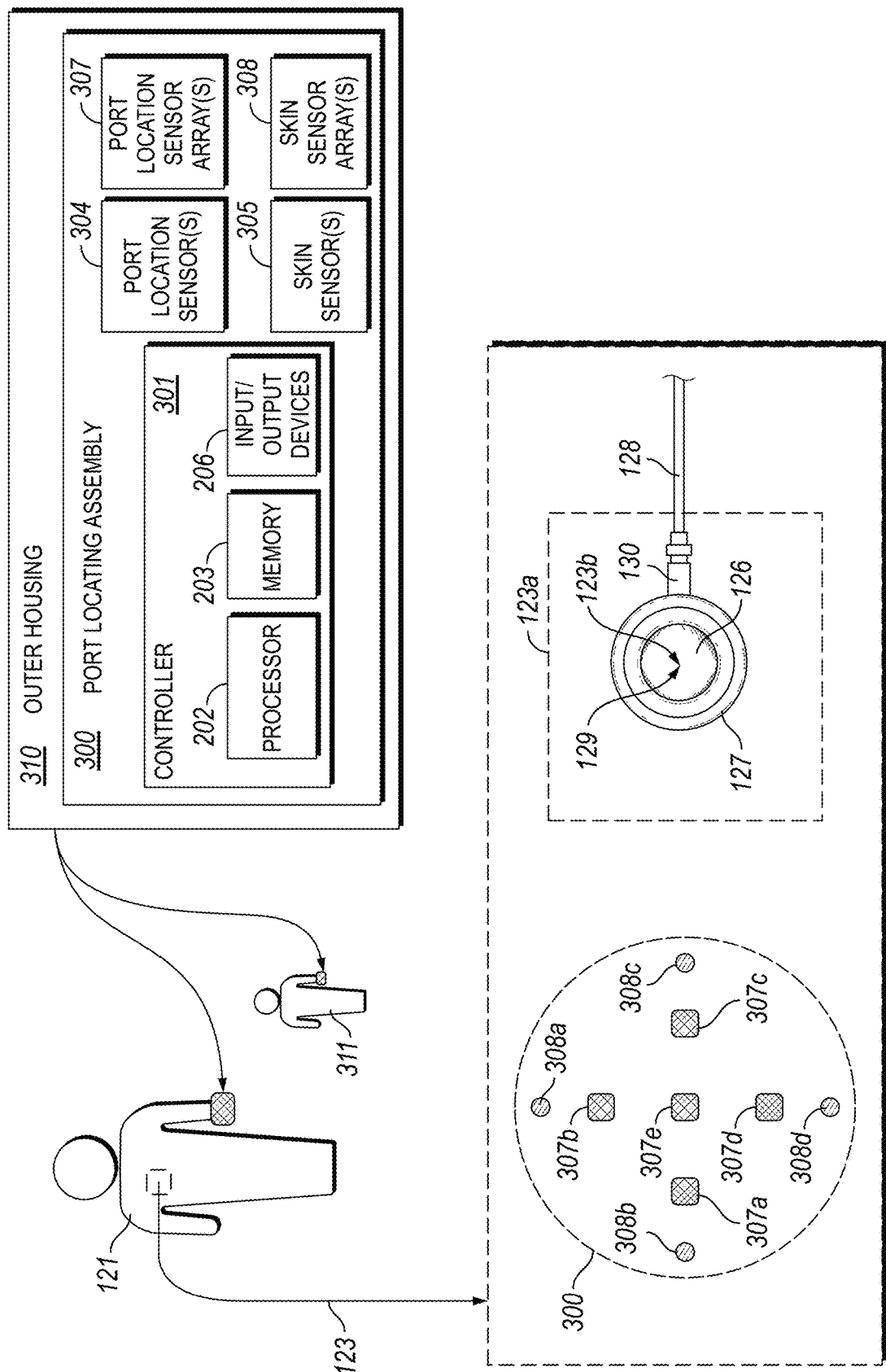
FIG. 3A is a schematic block diagram of a locating assembly to locate an implanted access port in accordance with an example embodiment.

In an example embodiment, the locating assembly may be used to determine the location of a port by moving the apparatus across a patient's skin. FIG. 3A illustrates an example embodiment of a method for locating a port. For example purposes, port 130 is illustrated as a single-lumen design having a rigid port housing 127, an elastomeric pierceable septum 126, and catheter 128 for delivering medication to the patient 121. Implanted access port 130 may have been previously situated by a healthcare provider under the skin 123 of a patient 121. The area of skin proximate to port 130 location may be designated 123a and may depend on the physiologic route of administration, specific access port model implanted, or patient anatomy.

In some embodiments, controller 301, port location sensor array 307, and skin sensor array 308 may be provided in outer housing 310 and configured to detect an access port 130 by differentiating a comparatively dense port housing 127 from a comparatively less dense port septum 126. Skin sensor array 308 may comprise skin sensors 308*a*, 308*b*, 308*c*, 308*d* situated to detect the presence or absence of skin 123. Port location sensor array 307 may comprise peripheral port location sensors 307*a*, 307*b*, 307*c*, 307*d* situated to detect a comparatively denser metal or plastic implanted port housing 127, and a center sensor 307*e* situated to detect a comparatively less dense elastomeric pierceable septum 126 of port 130. Although four skin sensors and four port sensors are shown, embodiments are not limited thereto, and any suitable number of sensors may be used.

In an example embodiment, port location sensor array 307 and controller 301 within the apparatus may be configured to compute the relative position of the locating assembly 300 to one or more features and/or regions of the implanted port 130. In an example embodiment, the relative position of locating assembly 300 to the implanted port may be determined via one or more arrays of port sensors as a user 311 moves locating assembly 300 over a patient's skin 123 or the patient's skin in proximity to an implanted port 130. The patient 121 may also, in some cases, be the user 311, as in the case of self-administration of a medication. In one or more embodiments, a change in relative position of the locating assembly 300 to the implanted port 130 may correspond to a change in a feedback state, which may optionally be communicated to a user of the apparatus.

Several example feedback states will now be explained to illustrate example embodiments of the disclosure and the various states during use. Although three states are shown in the examples illustrated by FIGS. 3B-D, embodiments are not limited thereto, and such examples should not be construed to limit embodiments of the disclosure to only three states. Indeed, in example embodiments, the three illustrated states may be included among pertinent states that may be determined for locating an implanted access port, but embodiments are not limited thereto.

Example Feedback State 1: Locating Assembly Far From Port

In an example embodiment, the controller 301 and port location sensor array 307 may be configured to infer that the locator assembly 300 is far from a port 130 implanted under the skin 123.

Figure 3B:
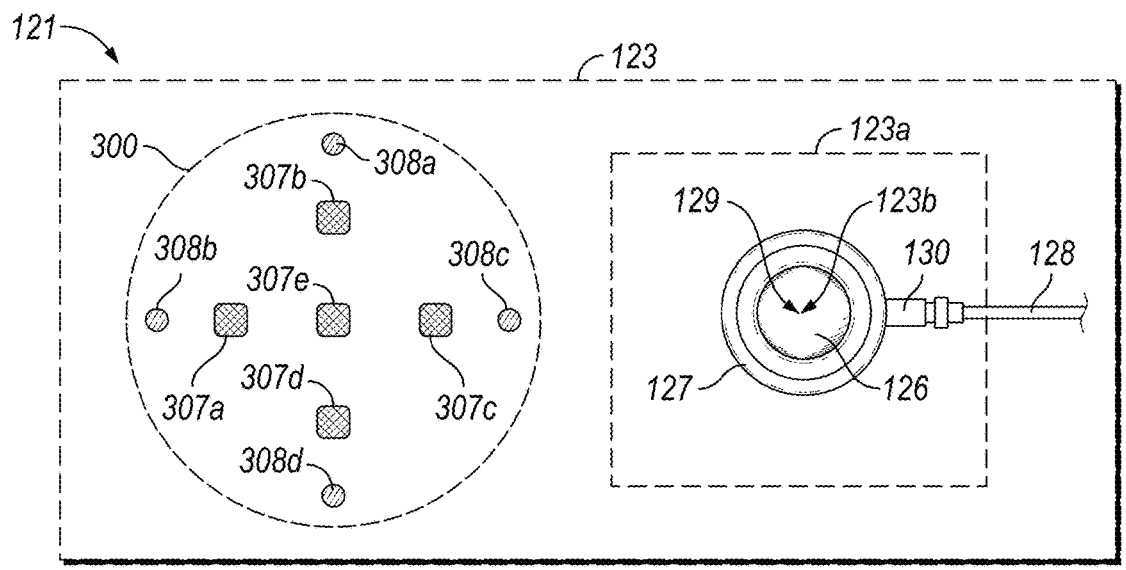
FIGS. 3B, 3C, and 3D are top view cutaway illustrations of a top view of a first, second, and third state, respectively, in a method according to an example embodiment to locate an implanted port using the locating assembly of FIG. 3A.

Referring to FIGS. 3A and 3B, initially, outer housing 310 may be positioned in an initial (e.g., first) position 320 far from a port 130 with pierceable septum 126, oriented so a port location sensor array 307 is against or near a patient's skin 123. Skin sensor 305, skin sensor array 308 data provided to the controller may optionally confirm that the port location sensor 304, port location sensor array 307, locator assembly 300, or outer housing 310 are properly situated (e.g., oriented) against or near a patient's skin 123. Data from port location sensors 307*a*, 307*b*, 307*c*, 307*d* and center sensor 307*e* may all be consistent with being in proximity to skin 123, and not to elastomeric port septum 126 or the port housing 127. Controller 301 may thus infer the locator assembly is neither near nor over the port 130. Controller 301 may also set one or more feedback states corresponding to "locating assembly far from port" or "needle not ready for insertion," and may optionally communicate feedback associated using one or more input/output devices 206.

Example Feedback State 2: Locating Assembly Approaching Port

In an example embodiment, the controller 301 and port location sensor array 307 may be configured to infer that the locator assembly 300 is in proximity to or approaching a port 130 implanted under the skin 123 but is not yet located directly over an elastomeric septum 126 of port 130.

Figure 3C:
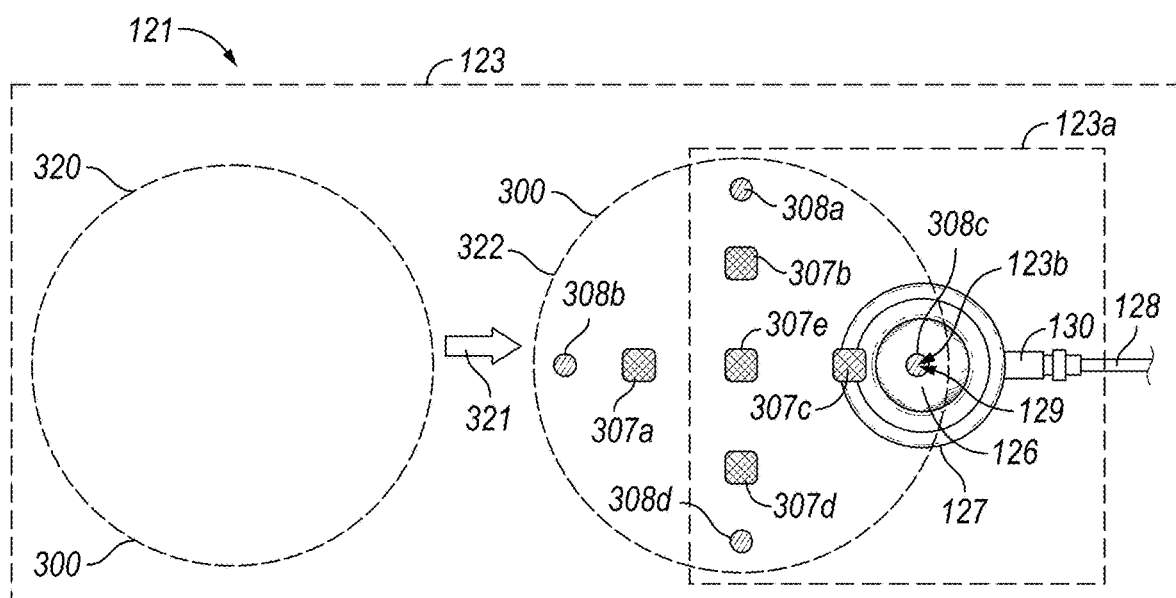

Referring to FIG. 3C, from the initial (e.g., first) position 320, port locating assembly 300 may be translated by a user 321 in a direction generally parallel to the skin 123 to a second position 322 closer to the implanted port 130 until one of the peripheral sensors 307*b* is situated over the implantable port housing 127. Skin sensor 305, skin sensor array 308 data provided to the controller may optionally confirm that the port sensor 304, port location sensor array 307, locator assembly 300, or outer housing 310 are properly situated (e.g., oriented) against or near a patient's skin 123.

Data from peripheral sensors 307*a*, 307*c*, 307*d* and center sensor 307*e* may all be consistent with being in proximity to skin 123, and not to the port housing 127 or elastomeric port septum 126. However, data from peripheral sensor 307*b* may be consistent with being situated over a metal or plastic port housing 127. Interpreting data collectively from sensors 307*a*, 307*b*, 307*c*, 307*d* and 307*e*, the controller 301 may thus infer that the edge of the locating assembly 300 is partially overlapping the port 130, that the center sensor 307*e* of the locating assembly is not over the elastomeric port septum 126, and that the port center 129 has not been located. Controller 301 may also set one or more feedback states corresponding to "locating assembly nearing port," or "needle not ready for insertion," and may optionally communicate feedback associated using one or more input/output devices 206.

Example Feedback State 3: Locating Assembly Over Port

In an example embodiment, the controller 301 and port location sensor array 307 may be configured to infer that the locator assembly is located directly over an elastomeric septum of the same port.

Figure 3D:
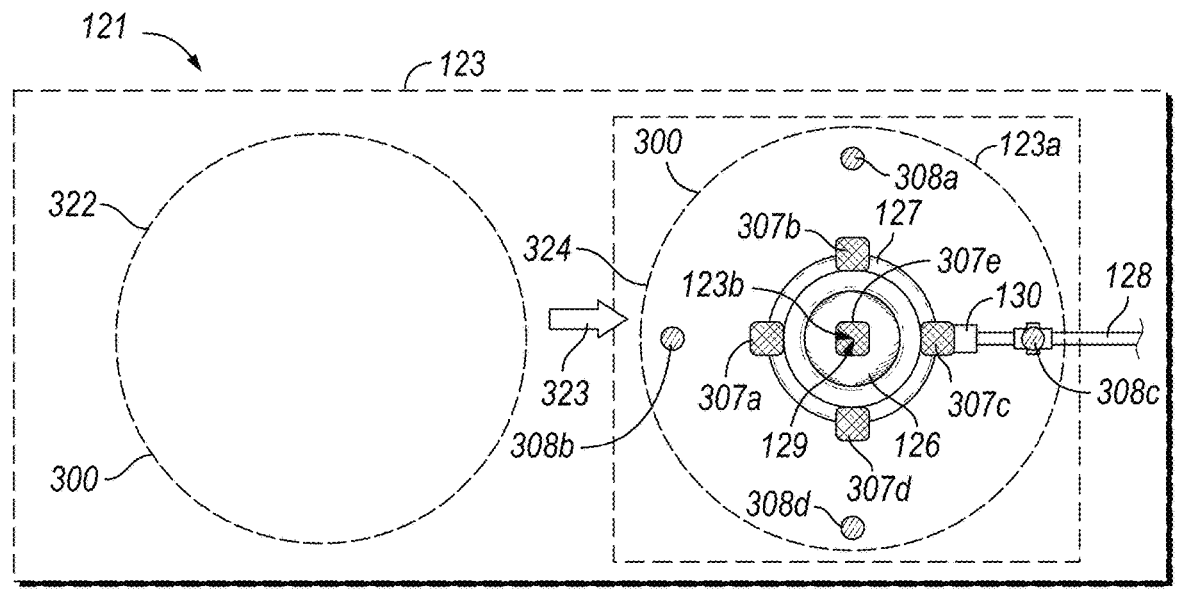

Referring to FIG. 3D, from the second position 320, port locating assembly 300 may be translated by a user 323 in a direction generally parallel to the skin 123 to a third position 324 still closer to the implanted port 130 and more specifically, directly over the implanted port 130. Sensor data from peripheral sensors 307*a*, 307*b*, 307*c*, 307*d* may all be substantially equal, consistent with the sensors being over (e.g., corresponding to) the port housing 127 (e.g., which surrounds the elastomeric port septum 126) rather than skin 123 or the port septum 126. Center sensor 307*e* data may be consistent with (e.g., correspond to) an elastomeric port septum 126. The controller 301 may interpret sensor data from 307*a*, 307*b*, 307*c*, 307*d* and 307*e* and infer that the edge of the needle assembly is directly over the port 130. The controller 301 may also set one or more feedback states corresponding to the inference made from sensors 307*a*, 307*b*, 307*c*, 307*d* and 307*e*. Controller 301 may also set one or more feedback states corresponding to "needle assembly over port," "needle ready for insertion," "skin ready for preparation," "site ready for injection," "injection device ready for attachment," or another suitable state, and may optionally communicate feedback associated using one or more input/output devices 206.

Although translation direction and/or speed are described for illustrative purposes, neither shall be construed as limiting the apparatus. Those skilled in the art will recognize based on the teachings herein that by the proper selection and configuration of sensors, controllers, software, and supporting circuitry will allow detection of many different states between those described here, and other states not described here. For example, controller 301 may sample the sensor arrays 307, 308 at an appropriately rapid rate to permit movement of the apparatus (e.g., translation over, or translation towards) relative to the skin 123 or implanted port 130 at a reasonably fast rate, or to accommodate slight variations in orientation of the surface of the outer housing 310 relative to the skin 123, such as non-parallel orientation. Alternatively, the apparatus may be provided with sensors and a controller configured to allow translational and/or rotational movement of the apparatus in any spatial direction relative to the port.

Detection of Inverted Port

In an example embodiment, controller 301 may be configured to detect, by way of one or more of port sensor array 307, or skin sensor array 308, an inverted access port 130.

As shown by example in FIG. 3E, an "inverted access port" may refer to an improper, undesirable orientation whereby access port 130, initially implanted beneath the skin 123 of a patient 121 with port septum 126 oriented outwardly towards the skin 123 and bottom port surface 130a oriented inwardly towards the interior body cavity and away from the skin 123 surface, is subsequently and undesirably reoriented to position port septum 126 improperly oriented inwards towards the body cavity and away from the skin surface, with the bottom port surface 130a of port 130 oriented outwardly towards the skin 123 surface. An inverted access port 130 precludes location, access, and delivery of one or more medications to a patient.

In an example embodiment, controller 301, port location sensor array 307, and skin sensor array 308 may be configured to infer that the locator assembly is located directly over an inverted access port. Referring to FIG. 3F, port locating assembly 300 is shown over an inverted access port housing 127. Sensor data from peripheral sensors 307a, 307b, 307c, 307d may all be substantially equal, consistent with the sensors being over the port housing 127 rather than skin 123 or the port septum 126. Such a condition may initially appear to controller 301 as the state corresponding to "needle assembly over port" as previously described with regard to FIG. 3D.

Figure 3E:
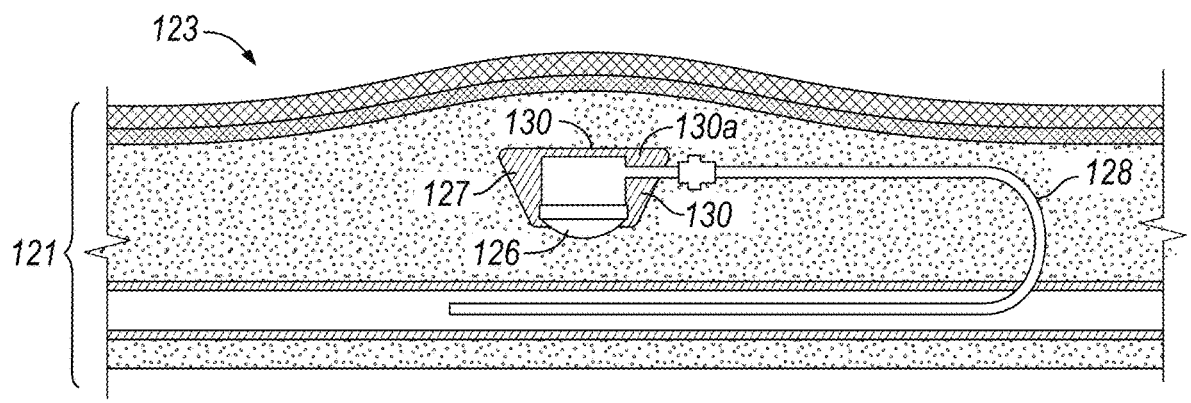
FIG. 3E shows a simplified partial cutaway front view diagram showing anatomic orientation of an inverted access port implanted underneath the skin of a patient.
Figure 3F:
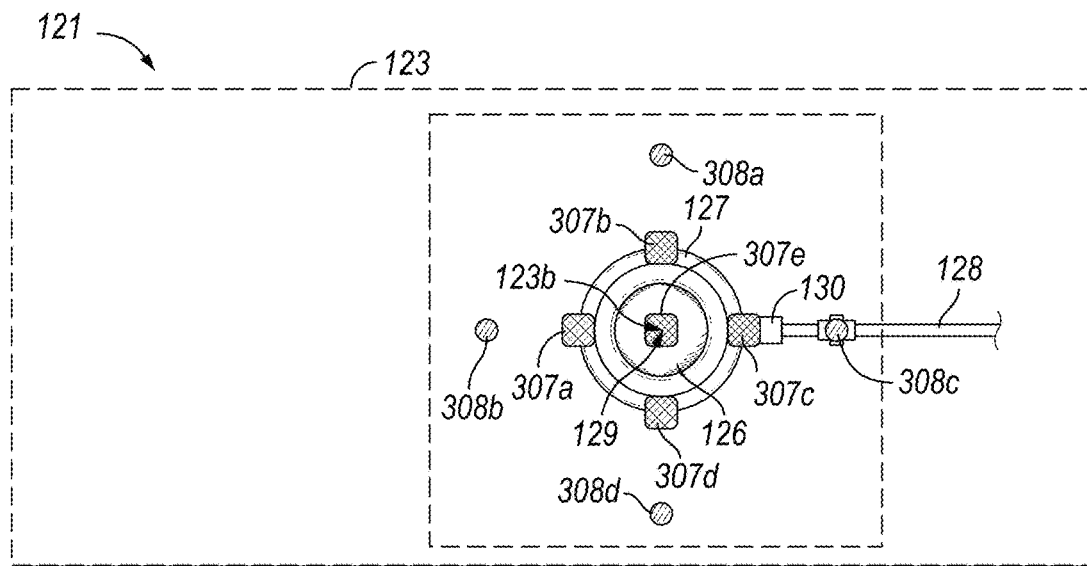
FIG. 3F shows top view cutaway illustration of a sensor configuration according to an example embodiment to detect an inverted, implanted port using the apparatus of FIG. 3A.

However, as center sensor 307e data may be consistent with being over the bottom port surface 130a, rather than skin 123 or the port septum 126 as expected, this may indicate that the port 130 is inverted, as shown in FIG. 3E. Thus, the controller may differentiate between an access port 130 that is correctly oriented (e.g., with port septum 126 oriented outwardly towards the skin 123) as described in FIG. 3D, and an inverted port.

Controller 301 may interpret sensor data from 307a, 307b, 307c, 307d and 307e and infer that port 130 is inverted. The controller may also set one or more feedback states corresponding to the inference made from sensors 307a, 307b, 307c, 307d and 307e. Controller 301 may also set one or more feedback states corresponding to "port inverted," "port unable to be used for medication administration," "port unsafe or unusable," or another suitable state, and may optionally communicate feedback associated using one or more input/output devices 206.

Example Method for Locating Access Port Implanted in a Living Body

Figure 10:
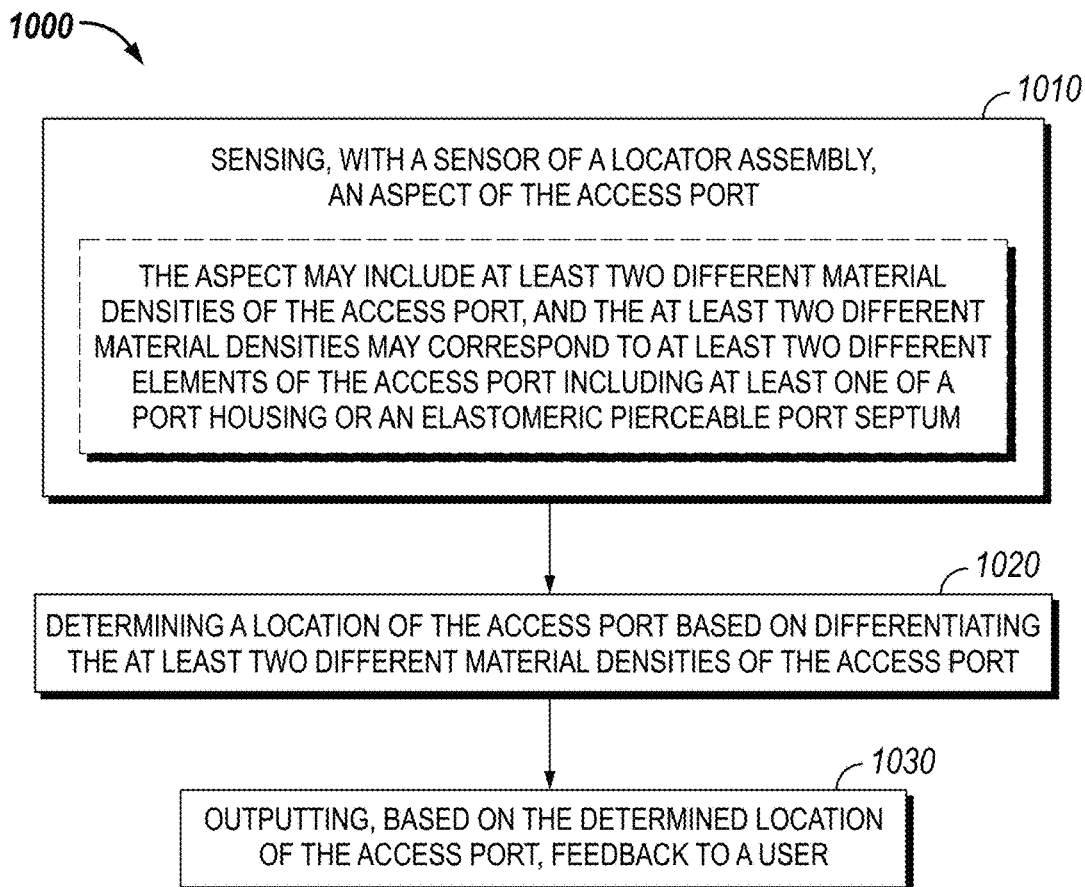
FIG. 10 illustrates a flowchart for an example method for locating an access port implanted in a living body according to an example embodiment.

With reference to FIG. 10, a method 1000 for locating an access port implanted in a living body according to an example embodiment may include sensing 1010, with a sensor of a locator assembly, an aspect of the access port. The aspect may include at least two different material densities of the access port, and the at least two different material densities may correspond to at least two different elements of the access port including at least one of a port housing or an elastomeric pierceable port septum. The method may further include determining 1020 a location of the access port based on differentiating the at least two different material densities of the access port, and outputting 1030, based on the determined location of the access port, feedback to a user.

In some embodiments, outputting the feedback to the user may include providing directional feedback to the user including both a direction of movement of the locator assembly to directly overlap with the access port and a relative proximity of the access port.

In some embodiments, the outputting the feedback to the user may include outputting the feedback to a remote device via a wireless interface.

In some embodiments, the feedback may be provided via the locator assembly, and the feedback may be at least one of tactile, visual, or audible.

Figure 11:
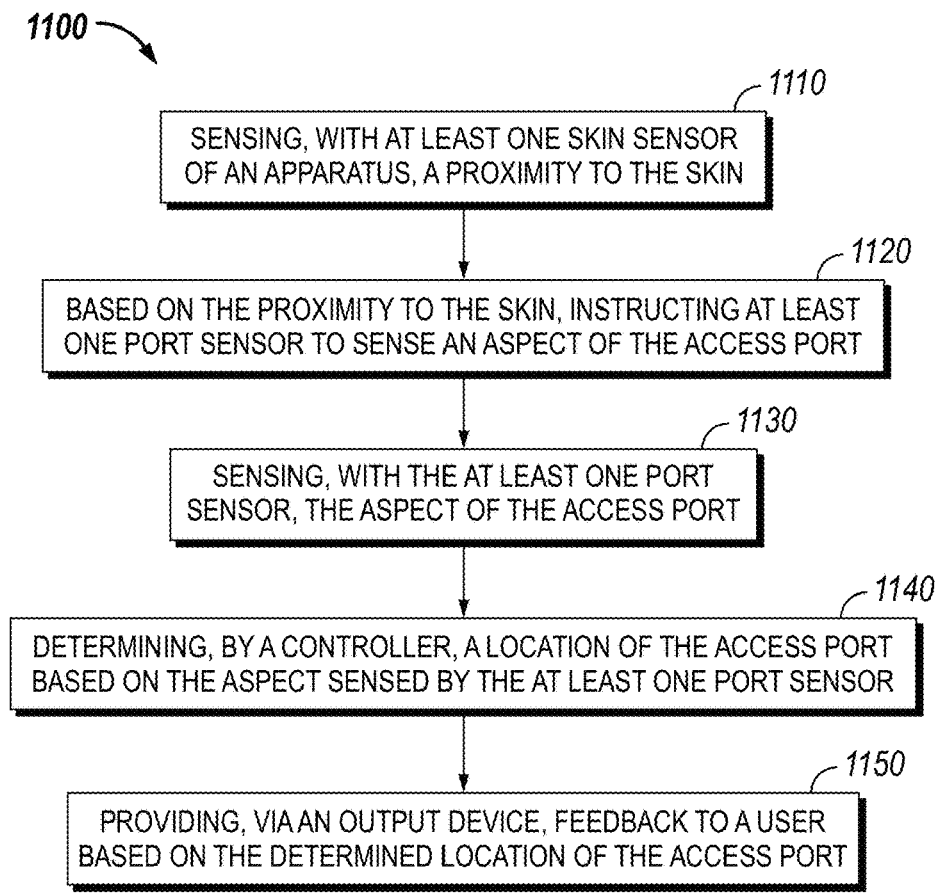
FIG. 11 illustrates a flowchart for an example method for using an access port implanted under the skin of a living body according to an example embodiment.

Example Method for Using an Access Port Implanted Under the Skin of a Living Body With reference to FIG. 11, a method 1100 for using an access port implanted under a skin of a living body may include sensing 1110, with at least one skin sensor of an apparatus, a proximity to the skin. Furthermore, the method may include, based on the proximity to the skin, instructing 1120 at least one port sensor to sense an aspect of the access port. Additionally, the method may include sensing 1130, with the at least one port sensor, the aspect of the access port. Also, the method may include determining 1140, by a controller, a location of the access port based on the aspect sensed by the at least one port sensor. And, the method may include providing 1150, via an output device, feedback to a user based on the determined location of the access port.

In some embodiments, the sensing the proximity to the skin may further include sensing the aspect at a first time interval when the at least one skin sensor indicates that the apparatus is beyond a predetermined threshold from the skin, and sensing the aspect at a second time interval when the at least one skin sensor indicates that the apparatus is at or within the predetermined threshold from the skin. The first time interval may be slower than the second time interval.

In some embodiments, the predetermined threshold from the skin may correspond to a height of the access port to account for a prominence of the access port underneath the skin.

In some embodiments, the first and second time intervals may correspond to sampling rates of the at least one port sensor, the first time interval may be at or below a frequency of 500 Hz, and the second time interval may be between a frequency of between 750 Hz and 1000 Hz, inclusive. In such an embodiment, the at least one port sensor may include a capacitive sensor and the first and second time intervals may be sampling rates for the capacitive sensor. In example embodiments where the at least one port sensor includes an ultrasonic sensor, the first and second time intervals for the ultrasonic sensor may be at lower frequencies, such as between 1-5 Hz and 5-50 Hz, respectively, or 1 Hz and 5-50 Hz, respectively, for example.

In some embodiments, the at least one skin sensor may include a pogo pin, and the method may further include controlling power to the pogo pin to sense a contact with the skin only when the proximity of the apparatus to the skin is within a predetermined threshold.

Example Embodiment: Standalone Locator

Outer Housing

Figures 1, 4A:
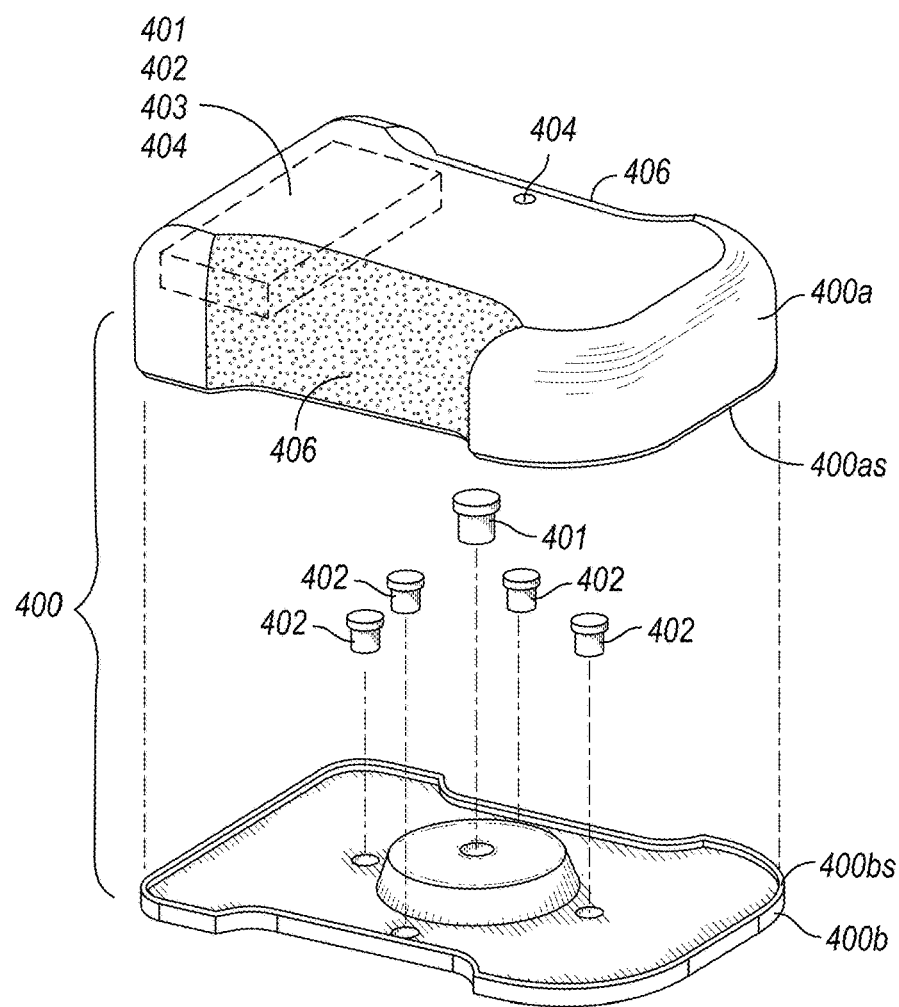
Figures 2, 4A:
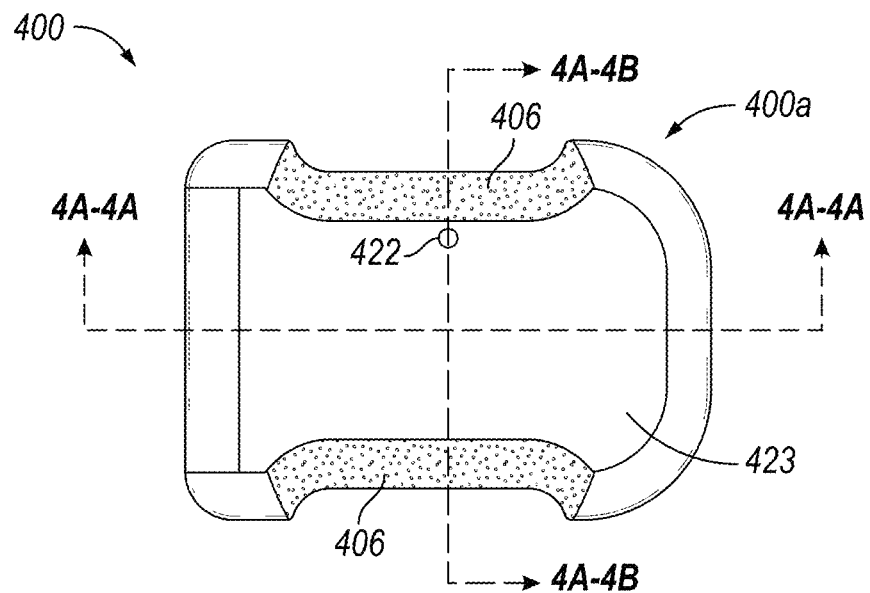
Figures 3, 4A:
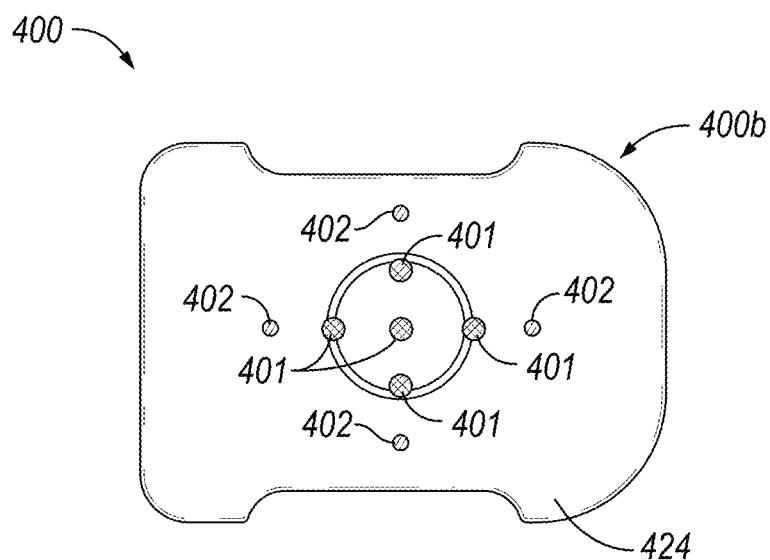
Figure 4A:
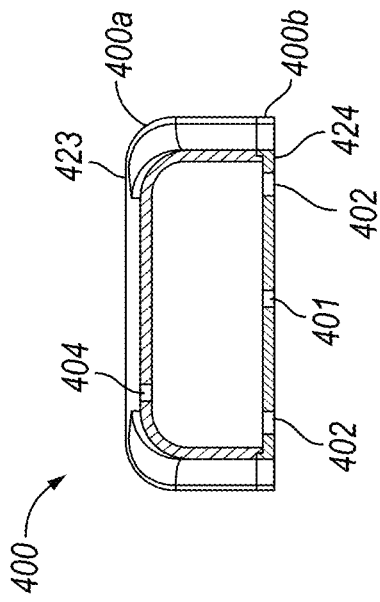
Figures 4A, 4B:
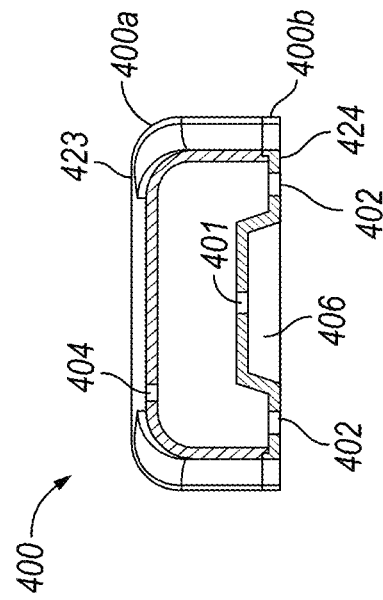

FIGS. 4A-1, 4A-2, and 4A-3 illustrate an exploded perspective, top, and bottom view, respectively, of a locating assembly in accordance with an example embodiment, FIGS. 4A-4A and 4A-4B illustrate cutaway views taken through lines 4A-4A and 4A-4B of FIG. 4A-2, showing cross sections of a locating assembly in accordance with an example embodiment, and FIGS. 4A-5A and 4A-5B illustrate cutaway views taken through lines 4A-4A and 4A-4B of FIG. 4A-2, showing cross sections of a locating assembly in accordance with an example embodiment. Referring to FIG. 4A-1, in an example embodiment, the locating assembly (e.g., 200 in FIG. 2, or 300 in FIG. 3A) comprising port sensors 401, skin sensors 402, controller 403, and input/output devices 404 may be provided in outer housing 400. In the example embodiment of FIG. 4A-1, outer housing 400 may take a contoured, substantially rectilinear shape. Outer housing 400 need not be rectilinear, but may take any suitable form, contour, size, or shape. Other alternative forms for the outer housing 400 may be based on the user population anticipated to use the apparatus; for example, an ovoid or handle-shaped outer housing may provide a balance of fine motor control needed to locate the port precisely (as shown in FIG. 4B-2), while taking into account user limitations, such as reduced vision or reduced dexterity, or other relevant factors that may affect patients with chronic diseases who may use the device.

Outer housing 400 may optionally be provided in one or more sections, which may be assembled during manufacture. For example, the outer housing 400 may be formed from an upper shell 400a and lower shell 400b; a portion of an outer shell may comprise a subassembly of one or more components of the apparatus described herein.

Snaps, tabs, detents, locking features, mechanical fasteners, ultrasonic welding, or heat staking may be used to assemble the outer housing sections (e.g., upper shell 400a and lower shell 400b) or outer housing subassemblies into a complete unit. Electrical components of the apparatus in the various sections or subassemblies may be connected through judicious use of spring loaded or "pogo pins," flexible interconnects, ribbon cables, cable harnesses, modular connectors, or other suitable electrical interconnects.

One or more of the portions of the outer housing 400, 400a, 400b may be injection molded and may be made from any rigid material such as nylon, acrylonitrile butadiene styrene, high density polyethylene, polypropylene, polystyrene, polycarbonate, and other rigid polymers or other materials having suitable rigidity. If injection molded, sections of outer housing 400, 400a, 400b may comprise portions of consistent and/or varying wall thicknesses. Some portions of the outer housing may be solid or may comprise a rigid outer shell and hollow interior. Some areas of the outer housing may be provided with thinner wall sections to allow proper visualization of visual indicators inside the outer housing from outside the housing by a user. The wall sections may also be selectively thinned to allow for audible feedback, such as from a speaker or piezoelectric driver, to be heard by a user. The wall sections may also be selectively thinned to allow proper operation of a sensor and may be selectively thickened to shield one or more sensors to prevent interference, spurious signals, or undesired operation. The wall sections may also be selectively thinned to allow for NFC pairing or inductive charging if such input/output devices are provided in the apparatus.

Sections of outer housing 400, 400a, 400b may be selectively thinned to allow one or more indicators provided by one or more input/output devices 404 inside the outer housing (e.g., visual or audible indicators) to be seen or heard by a user, or to allow for NFC pairing or inductive charging if such input/output devices are provided in the apparatus. Also, sections of outer housing 400, 400a, 400b may be selectively thinned to allow proper operation of a sensor and may alternatively be selectively thickened to shield one or more sensors to prevent interference, spurious signals, or undesired operation.

In some embodiments, outer housing 400, 400a, 400b may be provided with one or more shielding elements to allow proper operation of the sensors 401, 402 retained therein and avoid spurious or undesired operation. Outer housing 400, 400a, 400b may be configured to allow secondary assembly of shielding materials after manufacture of the outer housing or may be provided with shielding elements integral to the outer housing. Shielding materials for sensors 401, 402 may be also provided in the outer housing. For example, if the outer housing is molded from a polymer, one or more shielding materials may be incorporated into the polymer prior to molding; shielding may also be provided through secondary assembly or incorporation of one or more materials within the outer housing, inclusion of internal bosses, recesses, or thickened walls, by co-molding or over molding of one or more materials, or other appropriate methods. Any combination of shielding may be used, whether inside or outside outer housing 400, 400a, 400b, integral or separate from outer housing 400, 400a, 400b and one or more shielded components.

In certain use cases or environments, the outer housing 400, 400a, 400b and the openings and mating surfaces therein may contact fluids (e.g., water, saline, skin sterilant) that may cause damage to or undesired operation of the circuits, electronic components, or sensors within. In an example embodiment, outer housing 400, 400a, 400b, when assembled, may be sealed to substantially prevent fluidic ingress. In some embodiments, when assembled, outer housing 400 may be designed to prevent fluid ingress according to a specific standard (e.g., Ingress Protection Code of IEC 60529) and/or rating (e.g., IP54).

Areas that in some embodiments may be advantageously sealed include, for example, mating surfaces of outer housing sections (e.g., 400as, 400bs), protrusions for sensors, indicators, or one or more input/output devices. Sealing may comprise features within the outer housing or additional components, for example, gasketing, O-ring seals, co-molded sealing features in the outer housing, labyrinth seals, or other seals. Sealing may comprise features or components disposed inside outer housing 400, between portions of the outer housing 400, 400a, 400b, or on one or more exterior surfaces of the outer housing or portions of the outer housing, for example, where outer housing sections 400a, 400b connect.

Different sealing techniques may be used for different components of the apparatus, for example, the outer housing sections 400a, 400b or penetrations in a portion of outer housing 400 for sensors 401 and 402, or input/output devices 404, such as visible indicators. Sealing materials and methods may be selected to prevent intrusion of liquids, such as water, condensation, or may also be selected for compatibility with specific fluids the apparatus may encounter (e.g., chlorohexidine gluconate, chlorohexidine acetate, benzalkonium chloride, povidone-iodine, alcohol, or iodine). Sealing methods may be selected and designed based on the expected duration of use or frequency of exposure.

Such gasketing or sealing methods may also be omitted, and in some embodiments, one or more components of the apparatus (e.g., controller 403, sensors 401 and 402, printed circuit boards, circuits, or other electronic components) may be instead sealed against fluid intrusion by means of a conformal coating applied to one or more components of the apparatus prior to or during assembly into the apparatus. Conformal coatings may include, for example, epoxy, acrylic, polyurethane, silicone, or UV cured materials, combinations thereof, or other suitable materials and processes. Conformal coatings may be selectively applied to one or more components, and may be omitted from one or more components, such as optical input/output devices, connection points, flexible components, sensors, or other components that are incompatible with one or more coating materials, material characteristics, application, or curing processes. Conformal coatings may also be applied to one or more components of the apparatus to protect against unauthorized access to or tampering with electronic circuitry and components within the apparatus.

Referring to FIG. 4B-1, outer housing 400 may be handheld, allowing movement of the apparatus by a user 420 across a patient's skin 422 to locate an implanted port 421. In this configuration, a user 420 holding the outer housing 400 may generally orient user viewing surface 423 away from the skin 422 and skin contact surface 424 more proximately to a patient's skin 422 during use of the apparatus to locate an access port 421 implanted below the skin 422. In other words, when outer housing 400 is in use to locate an access port, user viewing surface 423 may be closest to the user holding the device, and skin contact surface 424 may be closest to the patient having the access port 421 being located. In a modification of the example shown in FIG. 4B-1, FIG. 4B-2 illustrates an example with outer housing 425, activation button 427 used to begin or end sensing of a port, input/output device 404 comprising one or more feedback indicators, and a clear viewing window 426, which may be included to aid in visualization of the skin 422, port 421, or lifted skin caused by a port prominence. The example embodiments illustrated in FIGS. 4B-1 and 4B-2 may not include a base plate as described further herein.

With reference to FIG. 4B-1, in some embodiments, a user 420 may translate or rotate outer housing 400 relative to the skin 422 during the process of locating an access port 421. Outer housing 400 may be grasped by a user 420 and conveniently moved closer to skin 422 (−Z direction) or further from the skin 422 (+Z direction). Such movement may be used to bring outer housing 400 into proximity of the skin and to begin to locate access port 421, optionally guided by skin proximity feedback provided by controller 403 and one or more input/output devices 404 as described herein. If outer housing 400 is in proximity to the skin, a user 420 may keep the outer housing 400 in a relatively constant relationship along the Z-axis and translate outer housing 400 along either or both of axis ±X or ±Y. Such translation may be used to locate the port 421 more precisely, optionally guided by directional or locational feedback provided by controller 403 and one or more input/output devices 404 as described herein. Controller 403 and sensors 401, 402 may be optionally configured to accommodate varying speeds of translation and rotation.

In an example embodiment, outer housing 400 may be moved in any combination of translation and rotation during use. While FIG. 4B-1 shows an example cartesian coordinate system by which the outer housing 400 may be translated or rotated relative to the skin 422 and access port 421, any axes may be used, and translation or rotation of outer housing 400 may take place in any direction, or in any combination of translation and rotation. For example, movement may also take place as a two- or three-dimensional vector combination of directions along any or all of the X, Y, and Z axes. Movement may also take place by way of rotation X*, Y*, Z* about the X, Y, and Z axes, also in one or more directions simultaneously, and also in conjunction with translation, if desired.

In an example embodiment, outer housing 400 may be provided with one or more relief features 406 to allow outer housing 400 to be more easily manipulated or to encourage a user 420 of the apparatus to grip outer housing 400 in a specific orientation during use. For example, relief features 406 may encourage or enable a user to grasp outer housing 400 between two fingers 420a, 420b in a pinch grip and thus orient or manipulate the apparatus to locate an access port 421 below the skin 422 as described herein.

Relief features 406 may include texturing, color, and may be of the same material, or a different material than outer housing 400. For example, if outer housing 400 is molded in a generally white (or light) color, relief features 406 may be molded in a contrasting color or texture, as by co-molding, over-molding, or use of in-mold decorations. Relief features 406 may also be provided with elements to improve grip, such as partially over-molding these features with a thermoplastic elastomer or texturing. The contour of relief features 406 may also be designed to encourage a specific grip, as by making an example grip more comfortable than a second alternative grip; alternatively, the contour may be shaped to suggest a proper grip, as by providing recesses for one or more fingers.

User Viewing Surface

Referring to FIG. 4C-1A, 4C-1B, 4C-2A, 4C-2B, 4C-2C, 4C-3A, and 4C-3B, in some embodiments, feedback indicators provided in a locating assembly outer housing 400 as an input/output device 404 may be visibly disposed on user viewing surface 423 to communicate information to a user 420 during one or more steps of access port 421 location using the apparatus. In some embodiments, feedback may correspond to a location substantially over (e.g., centered over) port 421.

In some embodiments, input/output devices 404 comprising feedback indicators may provide information to a user 420, corresponding to either or both of the relative location or proximity of the apparatus to an implanted port 421, or a proposed movement by the user to situate the apparatus in closer proximity to an implanted port 421. In some embodiments, information corresponding to relative location, relative proximity, or proposed direction of movement may be generated by controller 403 in response to data from sensors 401, 402.

Various example descriptions of feedback will now be provided; however, it should be understood that these examples are illustrative and embodiments are not limited thereto.

Figures 4, 4A, 5, 5A:
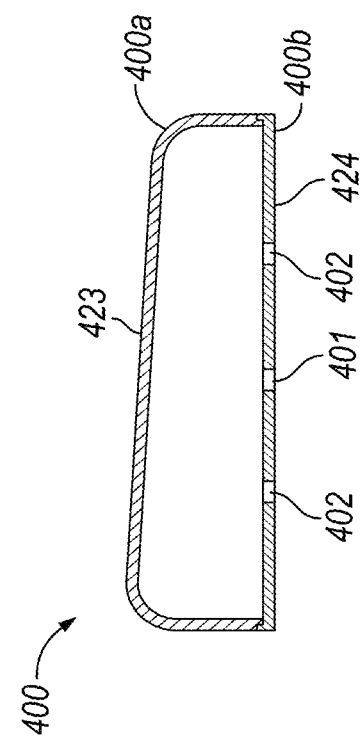
Figures 4, 4A, 5, 5B:
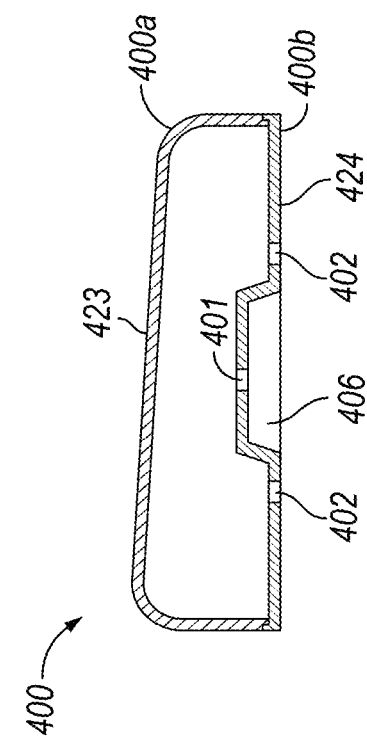
Figures 1, 4B:
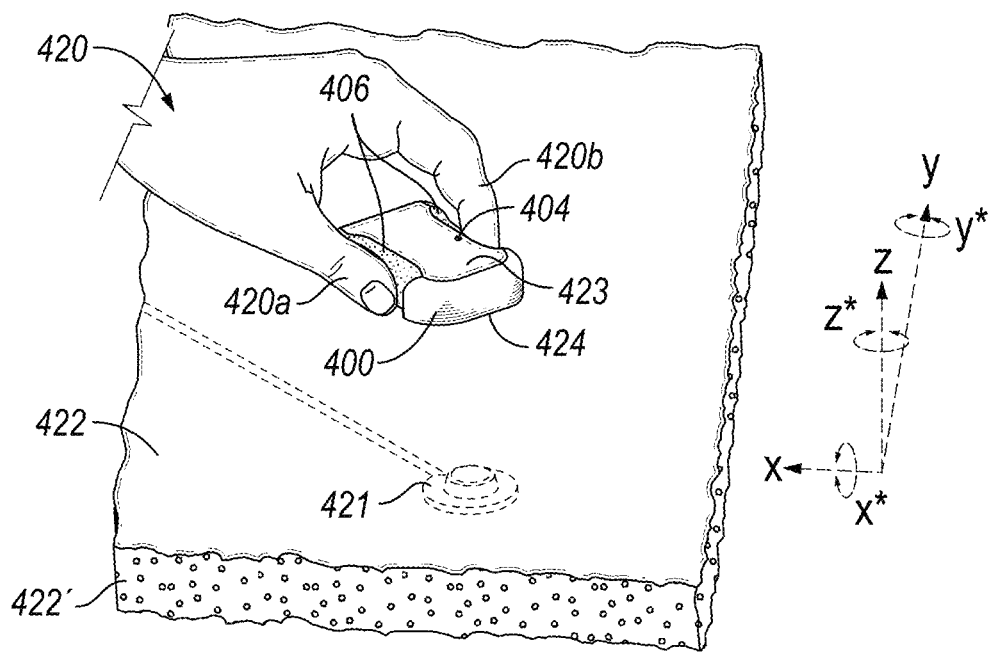
Figures 2, 4B:
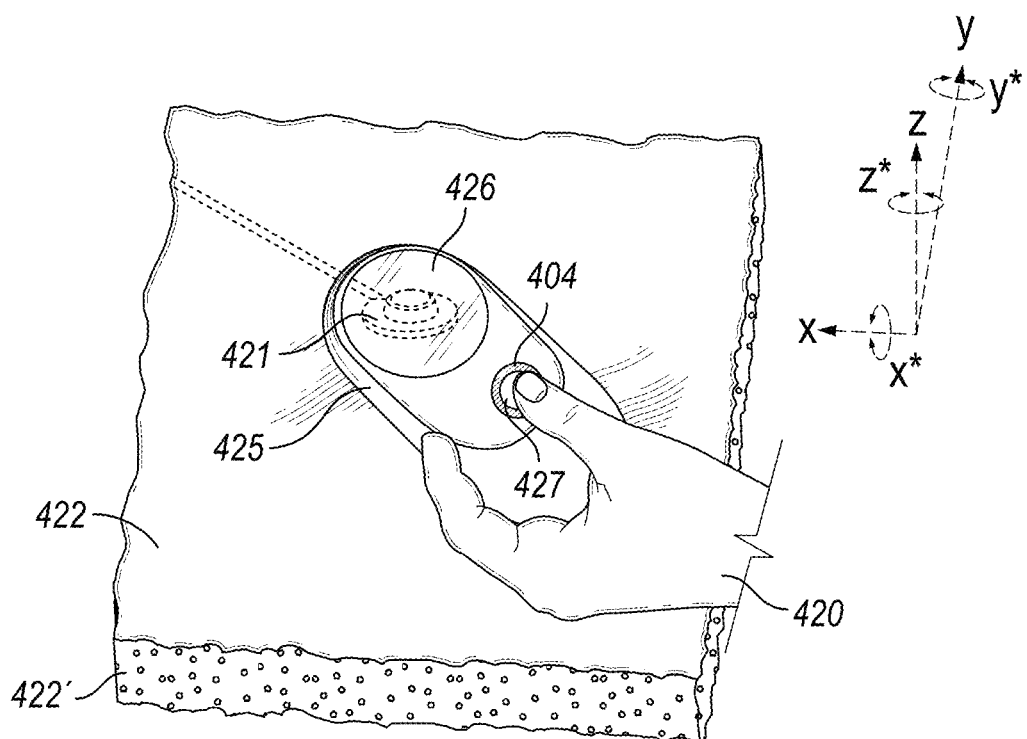
Figures 1A, 4C:
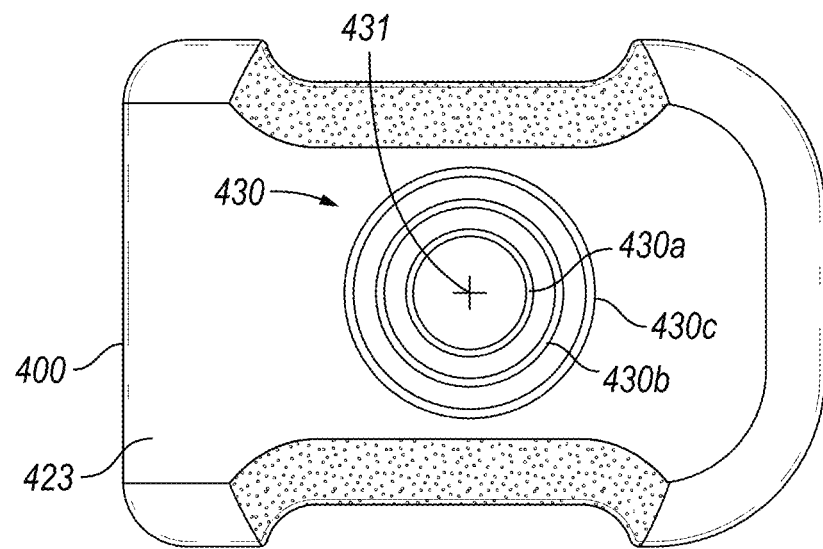
Figures 1B, 4C:
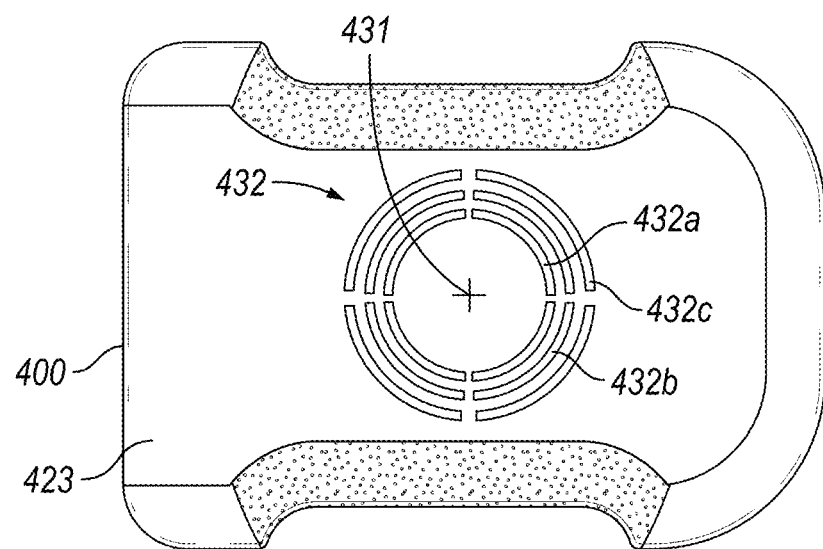

Referring to FIGS. 4C-1A and 4C-1B, in some embodiments, the visual feedback indicator disposed on the user viewing surface 423 may comprise a substantially circular or annular lighted indicator 430, 432 and center point 431 generally coinciding with either or both of a pierceable port septum or needle insertion site of access port 130. The annular lighted indicator may be positioned or sized to approximate the size and shape of an aspect of the access port, such as the port housing, improving intuitiveness to a user of the apparatus.

Annular lighted indicator 430, 432 may also comprise multiple concentric light rings (e.g., 430a/430b/430c, or 432a/432b/432c) extending radially from center point 431, for example, with successively larger outer and/or inner diameters and a desired spacing in between each annular ring. Annular lighted indicator 432 may be divided into one or more segments at regular angular intervals, for example, annular rings 432*a*, 432*b*, and 432*c*. While lighted indicator 432 is illustrated with four segments at 90-degree intervals, two or eight intervals or any other angular subdivision may be used.

In some embodiments, lighted indicator 430, 432 may comprise one or more multi-segment indicators, each segment (e.g., 430*a*, 430*b*, or 430*c*) being illuminated individually, in combination, or sequentially, and optionally animated in an extending or contracting radius from center point 431 to indicate the relative motion required in a specific direction. One or more aspects of a multi-segment indicator may be animated or flashed more or less rapidly or in different patterns or sequences, for example, to communicate relative distance or proximity to an access port.

Figures 2A, 4C:
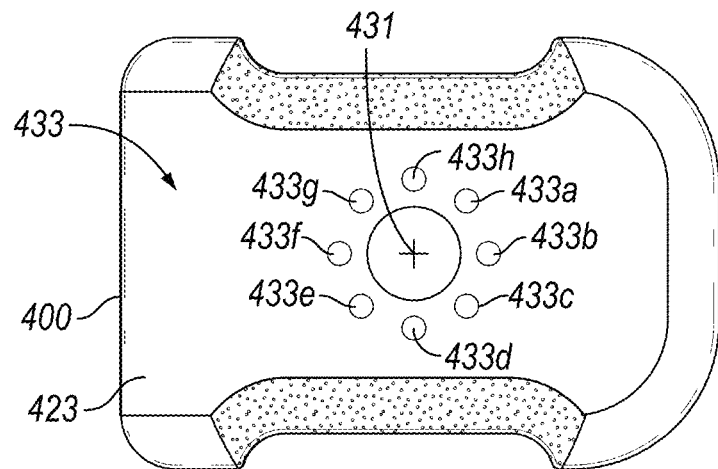
Figures 2B, 4C:
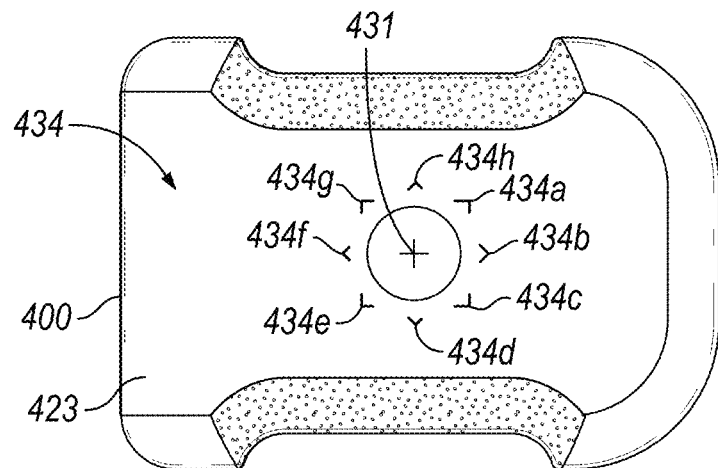
Figures 2C, 4C:
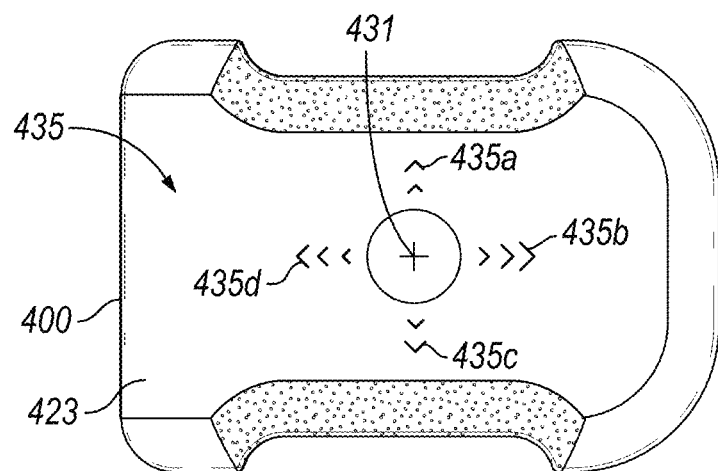
Figures 3A, 4C:
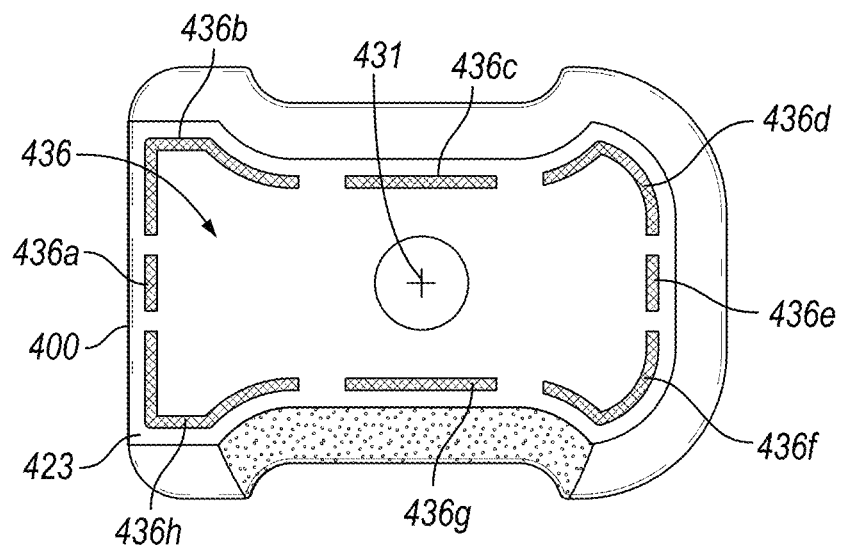
Figures 3B, 4C:
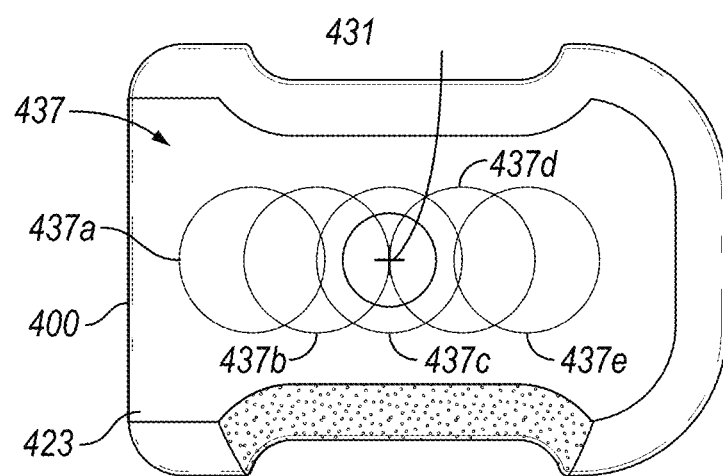

Referring to FIGS. 4C-2A to 4C-2C, in some embodiments, the visual feedback indicator 433, 434, 435 disposed on the user viewing surface 423 may comprise one or more lighted indicators radially disposed on the user viewing surface at regular angular intervals around a center point 431 generally coinciding with either or both of a pierceable port septum or needle insertion site of access port 130, as with directions on a compass. While visual feedback indicator 433 is illustrated with eight segments 433*a*-433*h* at 45-degree intervals, two or four intervals or any other angular subdivision may be possible. The radial distance of lighted indicators 433, 434, 435 from center point 431 may be equal or unequal, and may be determined based on the size and shape of outer housing 400 and user viewing surface 423.

Visual feedback indicators may also be provided in other geometries suggestive of a direction of movement, such as arrows of indicators 434, 435. Either multiple arrows 434*a*-434*h* may be arrayed at regular angular intervals as described previously, or multiple arrows may be combined into a single directional display 435*a*, 435*b*, 435*c*, 435*d*. A portion of the directional display (e.g., one or more arrows of display 435*a*) may be selectively illuminated, providing the capability to animate directional feedback to a user of the device. As an alternative to specifically-shaped lighted indicators 434, 435, it may be preferable to situate a LED or other illuminator below user viewing surface 423, then mask the LED by a label or in-mold decoration applied to the user viewing surface 423 during manufacture.

Referring to FIGS. 4C-3A and 4C-3B, in some embodiments, visual feedback indicator 433 may comprise one or more lighted indicators disposed on the user viewing surface 423 and taking a contour suggestive of the outer periphery of outer housing 400. While the visual indicator 433 is shown divided into eight segments, any number of segments may be used. In some embodiments, a portion of visual indicator 433 may be illuminated selectively (e.g., 436*d* singly, or 436*d*, 436*e*, and 436*f* in combination) corresponding to a recommended direction of movement to locate a port.

In some embodiments, visual feedback indicator 437 may comprise one or more overlapping lighted indicators disposed on the user viewing surface 423 and taking a contour suggestive the shape of a port housing 127 or a port septum 126. While the visual indicator 437 is shown with five illuminated indicators 437*a*-437*e*, any number of segments may be used. In some embodiments, a portion of visual indicator 437 may be illuminated selectively (e.g., 437*a* singly, or 437*d* and 437*e* in combination) corresponding to a recommended direction of movement to locate a port 130. Indicators may be animated (e.g., by repeatedly illuminating 437*d* and 437*e* successively) corresponding to a recommended direction of movement to locate a port housing 127 or port septum 126.

Feedback indicators 430, 432, 433, 434, 435, 436, and 437 may be visibly disposed on portions of user viewing surface 423 using any combination of methods, including having one or more indicators protrude through the surface of outer housing 400 or disposing them in a thinned cross section (e.g., 400 or 400*a*) acting as a diffuser. Alternatively, feedback indicators 430, 432, 433, 434, 435, 436*a-h*, and 437 may be disposed below user viewing surface 423 as previously described and selectively revealed through masking disposed on user viewing surface 423, as through pad printing, screen-printing, over labeling, use of in-mold decorations, or any other suitable technique. Additionally, although not illustrated in FIGS. 4C-1A to 4C-3B, instructional indicia may be provided on the user viewing surface 423 to aid interpretation of visual feedback, such as directions, text, arrows, dots, or other markings, also by pad printing, screen-printing, over labeling, use of in-mold decorations, or any other suitable technique.

Skin Contact Surface

Figures 1, 4D:
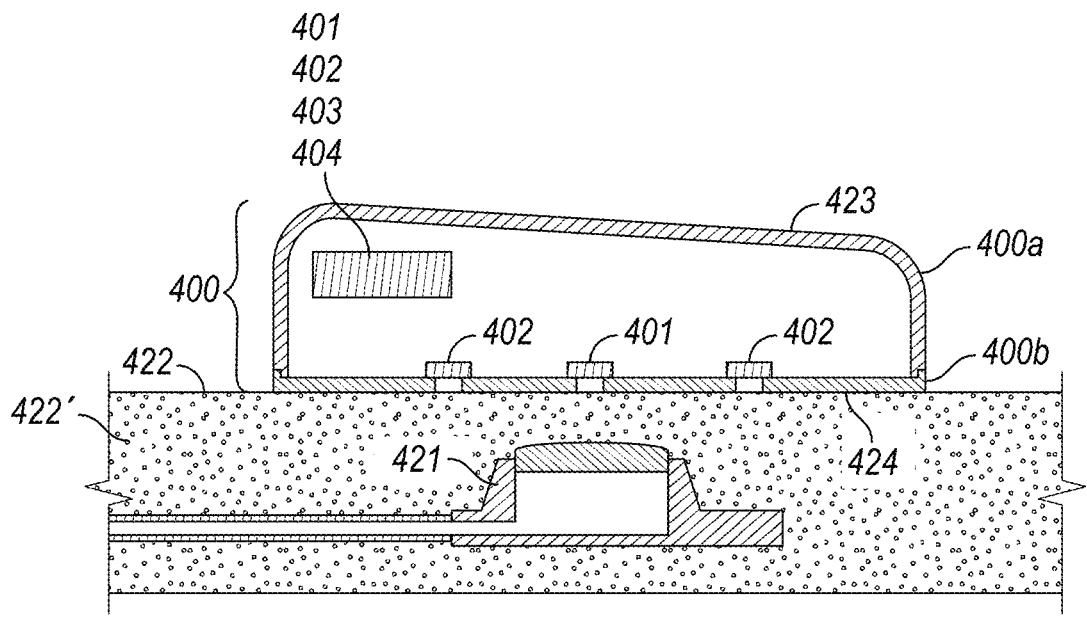
Figures 2, 4D:
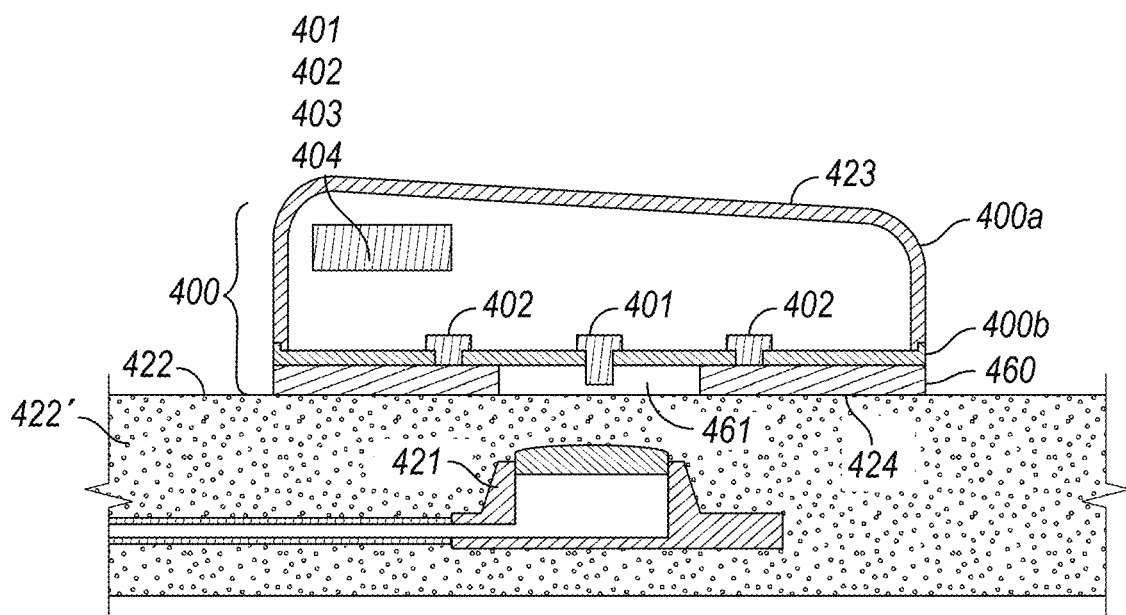
Figures 1, 4E:
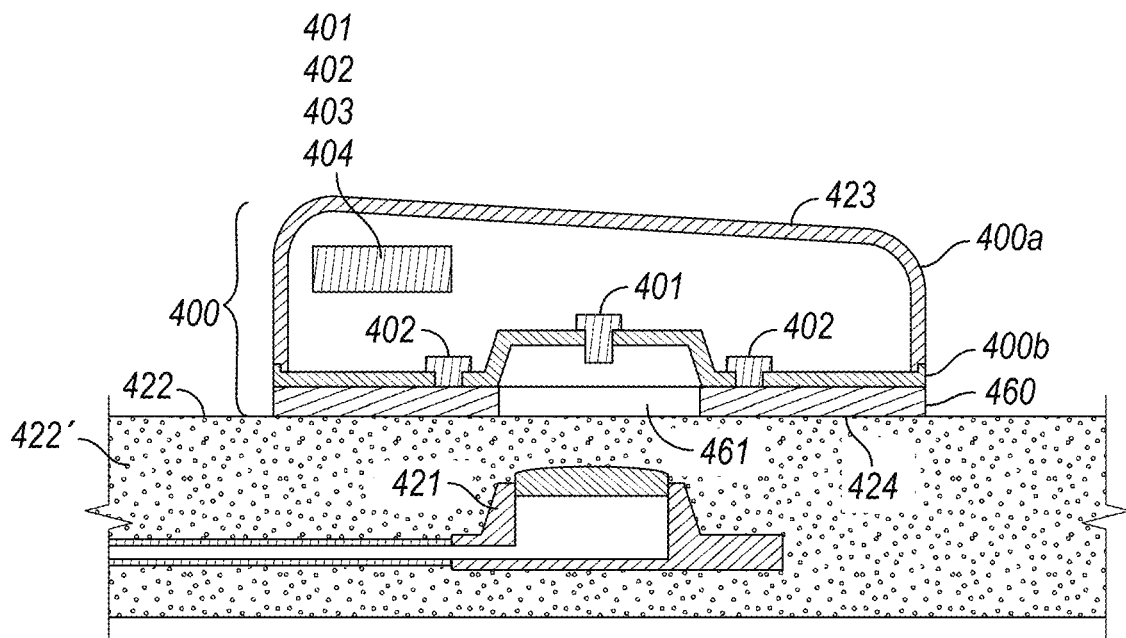
Figures 2, 4E:
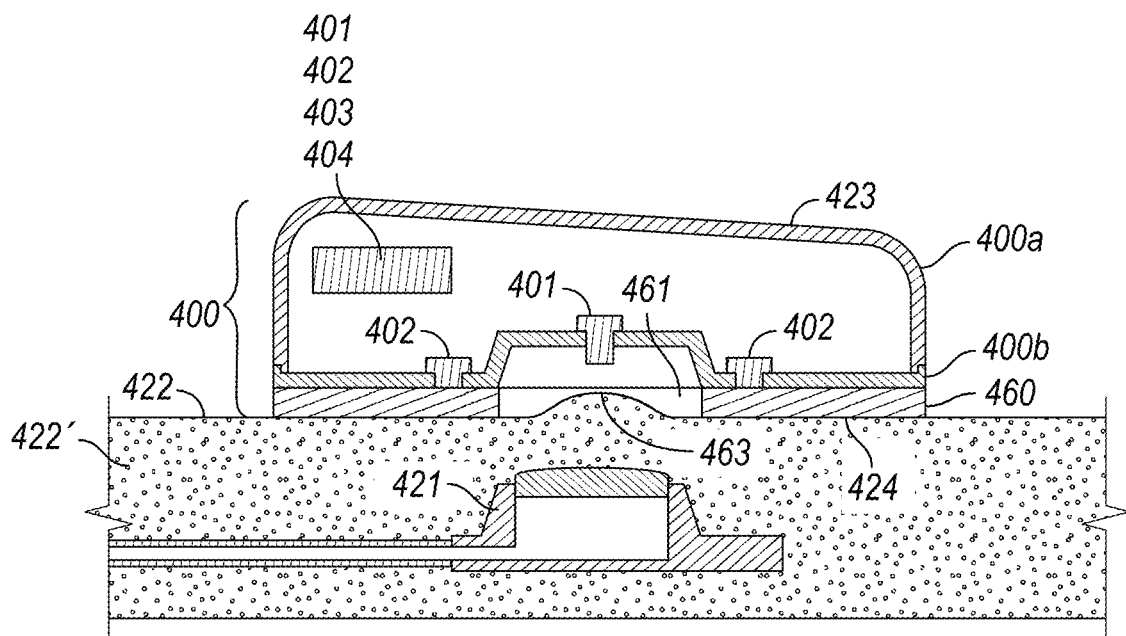

FIGS. 4E-1 and 4E-2 illustrate a sectional view of an outer housing 400 and skin 422 taken through line E-E as seen in the perspective view of FIG. 4A-2, according to an example embodiment. For illustrative purposes, outer housing 400 is shown generally above the skin 422 surface in proximity to access port 421, with the skin 422 interposed between outer housing 400 and port 421.

Skin contact surface 424 of outer housing 400 may be most proximate to the skin 422 in the orientation shown in FIGS. 4D-1 and 4D-2, corresponding to a step of locating an implanted access port using the apparatus. In an example embodiment, skin contact surface 424 may have port sensors 401 and optional skin sensors 402, all disposed to allow detection of one or more aspects of an access port 421 and/or skin 422. Sensors 401, 402 may be provided either individually or in port sensor arrays and the sensors and skin sensors may be positioned to avoid interference, as described previously. One or more of sensors 401, 402 may also be positioned elsewhere (e.g., aside from, protruding from, or separate from the outer housing 400) or may be positioned on other parts of the apparatus described herein, such as an adhesive element or mating ring (as described further below).

With reference to FIG. 4E-1, access port 421 may be under skin 422 in a substantially flat (e.g., parallel) manner. In other words, the skin in proximity to the implanted port may remain relatively parallel to the skin contacting surface 424 of outer housing 400. However, embodiments are not limited thereto. As illustrated in FIG. 4E-2, an access port 421, when implanted in a patient, may lift layers of skin 422 or soft tissues 422' underneath, creating a prominence 463 that disturbs the normally flat skin 422 surface and may interfere with location of port 421 by the apparatus or adherence of the apparatus or other components to the skin. Prominence 463 may be especially common in older patients or those with advanced disease, who may suffer from reduced skin elasticity (turgor), reduced subcutaneous fat (lipodystrophy), or reduced muscle tone (sarcopenia).

Thus, in some embodiments, skin contact surface 424 of outer housing 400 may also be provided with either or both of a port relief 461 or a flexible material layer 460 to accommodate a skin prominence 463 created by an implanted access port 421, thus allowing outer housing 400 and particularly skin contact surface 424 to be disposed in a substantially flat manner against the skin 422 surrounding the access port 421.

In some embodiments, port relief 461 may be concentric or substantially concentric with either or both of the port housing or the port septum. In this manner, positioning of port relief 461 may allow skin prominence 463 to protrude upwardly from skin contact surface 424 into port relief 461 within outer housing 400. This may advantageously preserve the skin contact surface 424 and skin 422 in a substantially flat (e.g., parallel) manner. Furthermore, this may advantageously provide a degree of protection against movement of the port housing relative to the outer housing 400, as skin prominence 463 is lightly constrained within port relief 461.

In some embodiments, port relief 461 may have a three-dimensional shape corresponding to one or more aspects of the implanted port, substantially corresponding also to the shape of the skin 422 and/or soft tissue 422' surrounding prominence 463. As configured in either of the embodiments described above, port relief 461 may allow prominence 463 to rise into a specific portion of the outer housing 400, thus allowing skin contact surface 424 to lie flat against the skin 422 surrounding prominence 463. Port relief 461 may be shaped as a hollow or depression with conical sides, a hemisphere, or other shapes, such as any three-dimensional shape.

In some embodiments, flexible material layer 460 may be provided on one or more portions of skin contact surface 424, for example, by over-molding a soft, compliant material, such as thermoplastic elastomer or thermoplastic polyurethane, or by applying or otherwise disposing an additional soft, compliant gel or foam material. Additionally, in some embodiments, one or more materials comprising the flexible material layer 460 may be disposed on a portion of interior surface of port relief 461.

The shape of port relief 461, and the thickness and contour of flexible material layer 460 may be selected according to shapes of access ports with which the apparatus will be used and the patient characteristics regarding skin 422 and soft tissues that determine the degree of prominence 463 to be accommodated.

Site Preparation & Sterilization

Figure 4F:
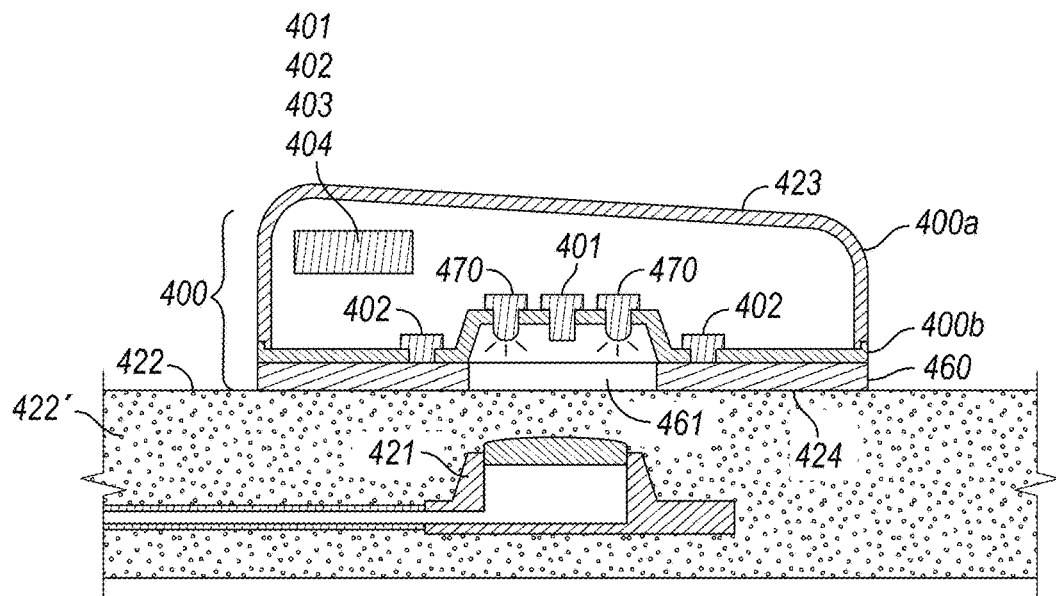

Once access port 421 is located, outer housing 400 may be disposed on the skin 422 over port 421. In some embodiments, port relief 461 or skin contacting surface 424 may be configured to prepare the skin 422 once an access port has been located but before the outer housing 400 is removed from the skin 422. As shown in FIG. 4F, in some embodiments, skin contact surface 424 may be configured with an input/output device 404 comprising one or more ultraviolet (UV) radiation sources 470 described previously, configured to irradiate and thus sterilize the skin 422 over a located port 421. In some embodiments, port relief 461 may be configured with a reflective material to maximize the radiative energy to which the skin 422 is exposed, thus maximizing the sterilant effect or reducing the time required for UV exposure. In some embodiments, an input/output device 404 may include an indicator corresponding to one or more states of skin sterilization, for example, sterilization ready, sterilization underway, or sterilization complete.

Example Embodiment: Locator Apparatus with Adhesive+Collar

FIG. 5A shows an example embodiment of a locator apparatus configured to locate an implanted access port as previously described with respect to example embodiments, to then prepare the skin over a located implanted port before port access takes place, and to allow subsequent patient access with a needle or a drug delivery apparatus. In an example embodiment, a locating apparatus 500 may comprise a locating assembly 502 and device side coupler 504 both disposed in outer housing 503, and a selectively detachable base plate 501 with adhesive flange 506. In some embodiments, locating assembly 502 and base plate 501 may be removably connected by cooperating device side coupler 504 and a base side coupler 505. In some embodiments, adhesive flange 506 may comprise one or more of a device side layer 507, a buffer layer 508, and a skin side layer 509. Adhesive flange 506 may optionally be provided with an oversized supportive scrim or border 535 for attachment to the base side coupler 505 by gluing, welding, crimping, co-molding, over-molding, insert molding, or other suitable permanent attachment.

Base Plate

Referring to FIG. 5B, in an example embodiment, the base plate 501 may comprise an adhesive flange 506 permanently attached to a base side coupler 505. Also in an example embodiment, adhesive flange 506 may comprise a skin side layer 509 with skin side surface 512 carrying an adhesive for attachment of the base plate 501 to a patient's skin 510 (e.g., the skin of a living body), a device side layer 507 with device side surface 511, and one or more buffer layers 508 interposed between the skin layer 509 and the device layer 507, wherein the layers 507, 508, 509 may be sealed together. In some embodiments, port relief 516 may optionally be provided in base side coupler 505 (e.g., by providing contoured section of opening 515), allowing a skin prominence (e.g., 463) to be accommodated as described previously.

One or more of the portions of the base plate 501 or base side coupler 505 may be injection molded and may be made from any rigid material such as nylon, acrylonitrile butadiene styrene, high density polyethylene, polypropylene, polystyrene, polycarbonate, and other rigid polymers or other materials having suitable rigidity. However, embodiments are not limited thereto, and in some embodiments, one or more portions of the base plate 501 or base side coupler 505 may be formed using, e.g., die cutting. All of or portions of the base plate 501 or base side coupler 505 may be fashioned from different polymers, either by molding separate components that are subsequently assembled, or by co-molding. If injection molded, sections of base plate 501 may comprise portions of consistent and/or varying wall thicknesses.

In some embodiments as described herein, the base plate 501 may be substantially rigid. However, embodiments are not limited thereto. For example, some embodiments may include a more flexible base plate 501, which may be provided to improve conformity to irregular or varying skin contours, to improve adhesive contact (e.g., conformance) to the skin, and/or to prevent inadvertent removal of the device (e.g., as may occur from snagging an edge of a more rigid base plate). Like as described for a more rigid base plate 501 according to example embodiments herein, a more flexible base plate 501 (which may simply be referred to herein as a "flexible base plate 501") may be provided with an adhesive flange 506 (optionally comprising one or more of a skin side layer 509, buffer layer 508, and device side layer 507) and base coupler 505 with optional port relief 461, as may be described herein. The flexible base plate 501 may also be provided with optional features, such as text or graphic indicia (e.g., 531*g*, 531*t*, 530*o*), or supporting features (e.g., 530), also as described herein.

In some embodiments, base side coupler 505 may be integrally molded into base plate 501 (which may, for example, be a rigid or a flexible base plate as described herein, and may include device side layer 507) or otherwise molded into adhesive flange 506. This may avoid the need for joining operations (e.g., base side coupler 505 to adhesive flange 506 as separate components joined during manufacturing, such as by using glue), additional features (e.g., scrim 535) or multiple components (e.g., base side coupler 505 to adhesive flange 506). In some embodiments, portions of adhesive flange 506 and/or flexible base plate 501 may be co-molded in a first comparatively more flexible material, while base coupler 505 may be co-molded in a second comparatively more rigid material, yielding a unitary component and thus simplifying manufacturing and improving the integrity of the connection of base side coupler 505 to adhesive flange 506.

In some embodiments, as discussed herein, one or more portions of adhesive flange 506 and/or flexible base plate 501 (e.g., including device side layer 507) may comprise a comparatively more flexible material, such as those described herein, while base coupler 505 may be fashioned from a comparatively more rigid material. In example embodiments, comparatively more rigid materials may include, for example, at least one of nylon, acrylonitrile butadiene styrene, high density polyethylene, polypropylene, polystyrene, polycarbonate, other rigid polymer(s), or combinations thereof. Comparatively less rigid materials may include, for example, silicone rubber, thermoplastic elastomer (TPE), or blends of silicone or TPE and other polymer material(s), or combinations thereof, such as for the desired balance of rigidity and flexibility (e.g., elastic modulus). Both the comparatively more rigid materials and less rigid materials described herein may also be selected based on skin compatibility and hypoallergenicity.

In some embodiments, locating assembly 502 may be removably pre-attached via device side coupler 504 and base side coupler 505 to flexible base plate 501 during manufacturing. For instance, locating assembly 502 may be removably threaded onto (e.g., in threaded cooperation with) base side coupler 505 to flexible base plate 501. Such an apparatus may be used as described herein to locate a port and adhere a base plate. The threaded connection may surround an opening 515 of the base plate including the base coupler.

As some flexible materials also exhibit generally higher torsional and sliding friction (e.g., silicone), in some embodiments, materials comprising the device side coupler 504 and base side coupler 505 may include a friction-reducing material, such as liquid or dry lubricant (e.g., a silicone such as Dow 360 silicone or other silicone commonly used in medical applications), including on the threaded connection, or incorporation of slip additive into the feedstock during molding of either component. Such a construction may be configured for easier removal of locating assembly 502 from flexible base plate 501 after use, or for easier attachment of subsequent devices to flexible base plate 501 after location of the port and attachment of the base plate to the skin.

In some embodiments, a controller 201 may determine, based on a sensed aspect of the access port, that the apparatus (such as the base plate 501) has an incompatibility with the access port. Indeed, in some embodiments, the base plate 501 may be configured to cooperate with access ports only of a certain predetermined manufacturer. In some embodiments, the locator assembly may provide feedback to the user indicating the incompatibility. In an example, the determination may be made based on determining a manufacturer of the access port using the sensed aspect. In some embodiments, the locating assembly may include a locking mechanism (e.g., mechanical in nature) that, upon the controller 201 determining the incompatibility, may be instructed by the controller 201 to lock couplers 504, 505 together to prevent detachment of the locating assembly 502 from the base plate 501.

Adhesive

In an example embodiment, skin side surface 512 may carry one or more adhesives suitable for skin, configured to secure the base plate 501 temporarily to the skin 510 of a patient. The adhesive (which may also be referred to herein as an adhesive layer) may comprise a viscoelastic material that displays tackiness and adheres well to a wide variety of substrates (e.g., the skin) after applying only light pressure (e.g., finger pressure), such as a pressure sensitive adhesive. While the adhesive may be transparent, the color of the adhesive may be varied if, for example, it is advantageous to do so, as for intuitive application or easy visualization by a user of the apparatus. While an adhesive may be applied to a major portion of skin side surface 512, it may be selectively included or excluded from one or more portions of skin side surface 512, for example, to aid in removal when no longer needed.

The adhesive may also be covered by a release liner, which may be a non-stick material or film, optionally siliconized to further enhance non-stick properties. In some embodiments, the release liner may first be removed for the user to adhere adhesive flange 506 to the skin and may be cut, slit, perforated, or provided in one or more selectively removable segments to allow progressive exposure of the skin adhesive during application by a user. In some embodiments, one or more portions of the release liner are removed prior to locating the port and before adhering base plate 501 to the skin 422. In some embodiments, one or more portions of the release liner are removed after locating the port and before adhering base plate 501 to the skin 422. In some embodiments, the release liner may be spiral cut such that it can be unwound and removed from the adhesive without applying (or by applying a small degree of) downward force, such that the base plate 501 may remain relatively flush with the skin as the release liner is removed for adherence. In some embodiments, the outermost portions of base plate 501 may be bendable and include the adhesive with release liner applied thereto. In such embodiments, the release liner may be removed from the bendable portions after locating the port, and the bendable portions may be thereafter bent downward to be flush and pressed against the skin, thereby adhering the base plate 501 to the skin 422. In some embodiments, the adhesive may be water-activated and the release liner may not be included. In such embodiments, upon locating the port, the adhesive may be activated with water to adhere to the skin 422. However, embodiments are not limited thereto, and in other embodiments, the adhesive may be activated through other manners, such as any fluid, light, vibration, etc.

The example adhesive flange 506 formed by layers 507, 508, 509 in a direction parallel to axis Y-Y may be generally a flat low profile with substantially uniform thickness. However, the thickness of adhesive flange 506 may be varied widely, depending on the configuration of the apparatus, the characteristics of devices to be subsequently attached to the coupling (e.g., their weight), patient characteristics, anticipated relative movement of the different components attached to the apparatus, degree of skin and/or patient movement during use, ease of attachment and removal from the skin, skin characteristics of a specific user population for the apparatus, or other relevant factors.

In some embodiments, multiple materials may be joined together to comprise adhesive flange 506 including one or more of the skin side surface 512, device side surface 511, device layer 507, buffer layer 508, and skin layer 509. In some embodiments, one or more of the skin side surface 512, device side surface 511, device layer 507, buffer layer 508, and skin layer 509 may comprise a conformable polymeric layer, such as a foam or foam composite.

Materials comprising adhesive flange 506 may be selected based on biocompatibility, hypo allergenicity, high skin adhesion, ease of removal from the skin, resistance to sterilization, antimicrobial properties, antifungal properties, antiviral properties, or other relevant factors. One or more materials may also be permeable or impermeable to liquids and/or air, or a combination thereof. One or more portions of adhesive flange 506 may be transparent, semi-transparent, colored, or tinted; optionally, color or tinting of one or more materials may indicates the presence of, or type of, an antimicrobial, antifungal, or antiviral agent (e.g., povidone iodine, iodine, chlorhexidine gluconate, or polyhexamethylene biguanide) in adhesive flange 506 to a user of the apparatus.

As described earlier, port access may be a sterile procedure, and proper skin preparation may be important in some embodiments. In an example embodiment, a material on skin side surface 512 may comprise an adhesive disposed on a film with one or more of persistently antimicrobial, antifungal, or antiviral properties. Also in an example embodiment, skin side surface 512 may be provided with an adhesive composite comprising a pressure-sensitive adhesive and one or more of a persistently antimicrobial, antifungal, or antiviral agent. An "antimicrobial" may comprise one or more of an antimicrobial, antifungal, or antiviral agent, each with either transient or persistent effect. In some embodiments, such an antimicrobial may be provided as a controlled release formulation.

In some embodiments, a persistently antimicrobial film provided on skin side surface 512 may be disposed in direct contact with the skin 510 over an implanted port 513 by the apparatus. By way of example, an antimicrobial film may comprise an iodine-containing film or a chlorhexidine gluconate containing film, both of which are incorporated herein by reference. Alternatively, skin side surface 512 may be provided with an adhesive be co-formulated with a persistently antimicrobial material in place of a separate antimicrobial film layer on skin side surface 512 or may be provided as a foam co-formulated with (or coated with) with an antimicrobial agent.

Figure 5A:
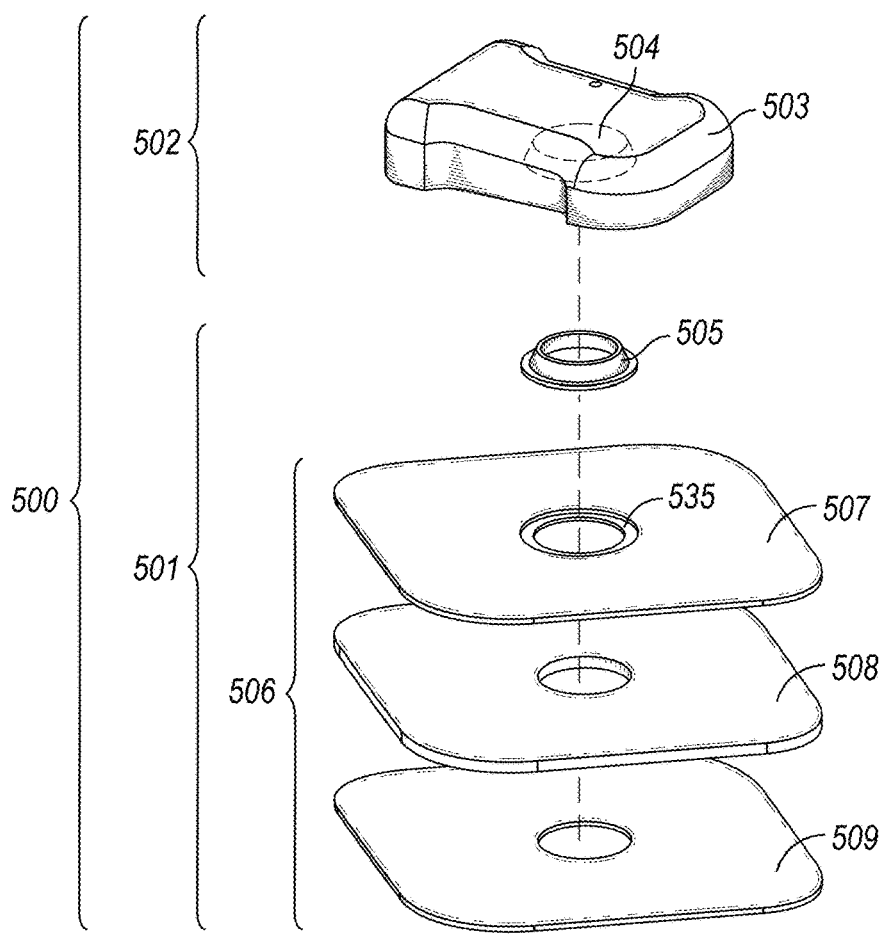
Figure 5B:
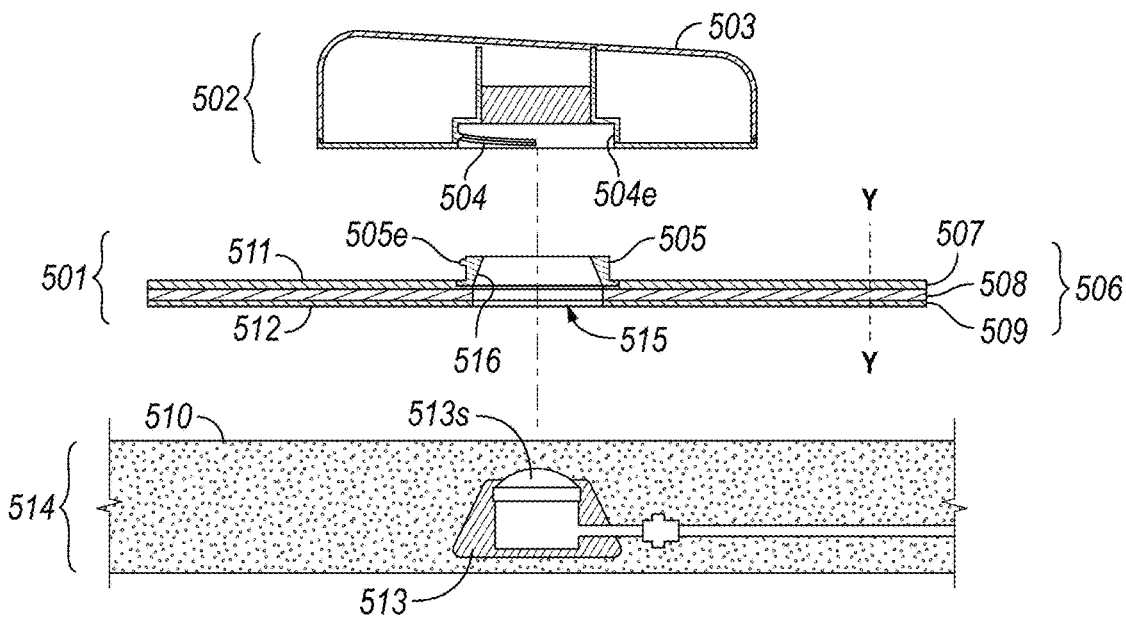
Figures 1, 5C:
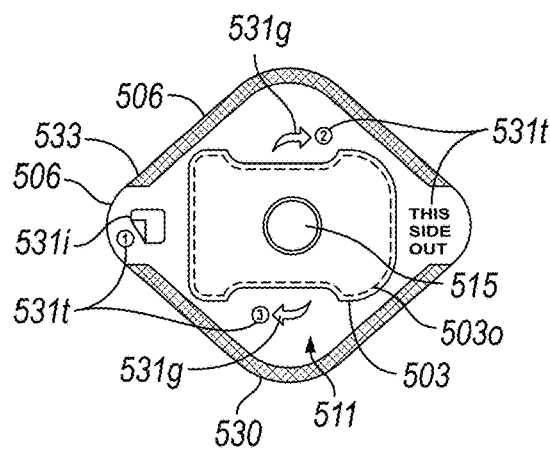
Figures 2, 5C:
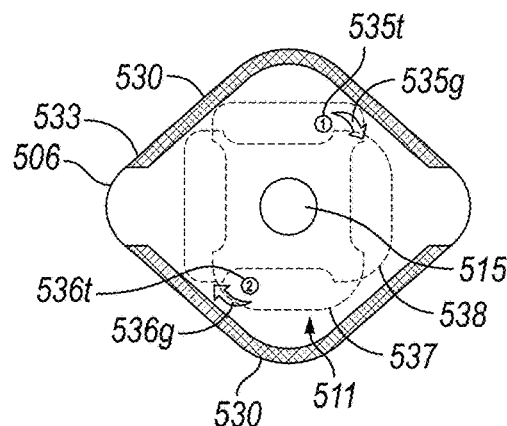
Figures 3, 5C:
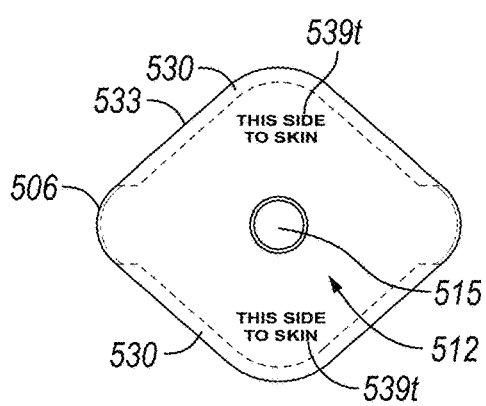
Figures 4, 5C:
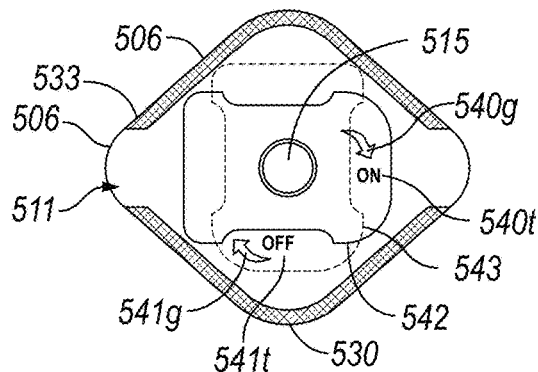
Figures 3, 5D:
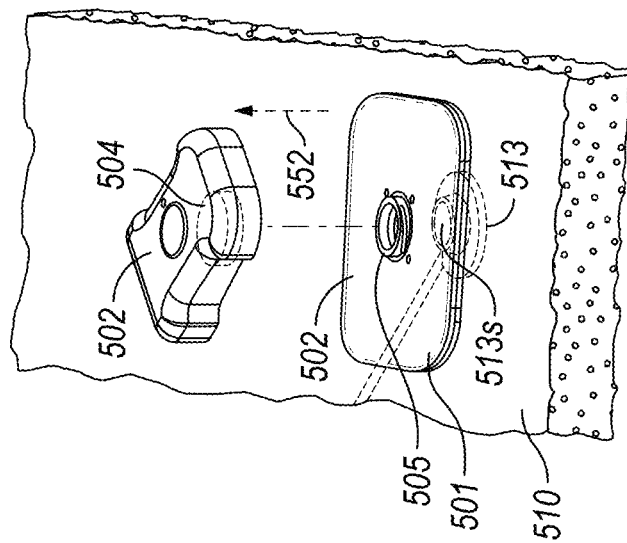
Figures 2, 5D:
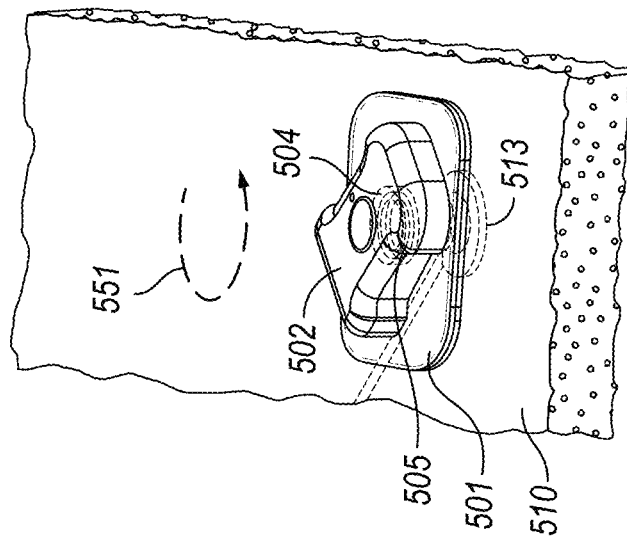
Figures 1, 5D:
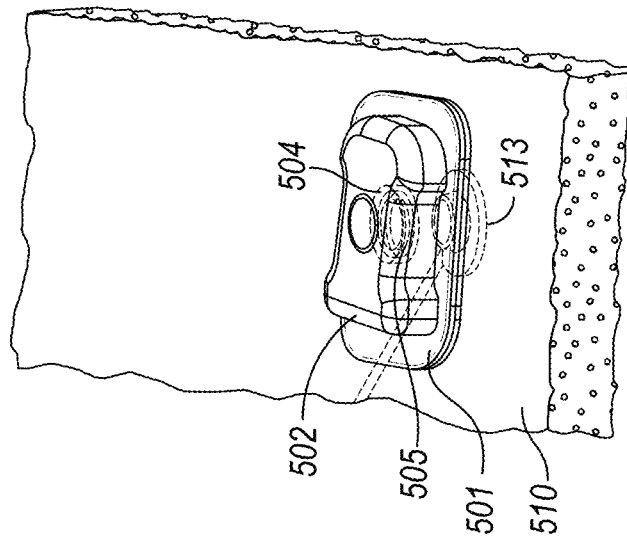
Figure 5E:
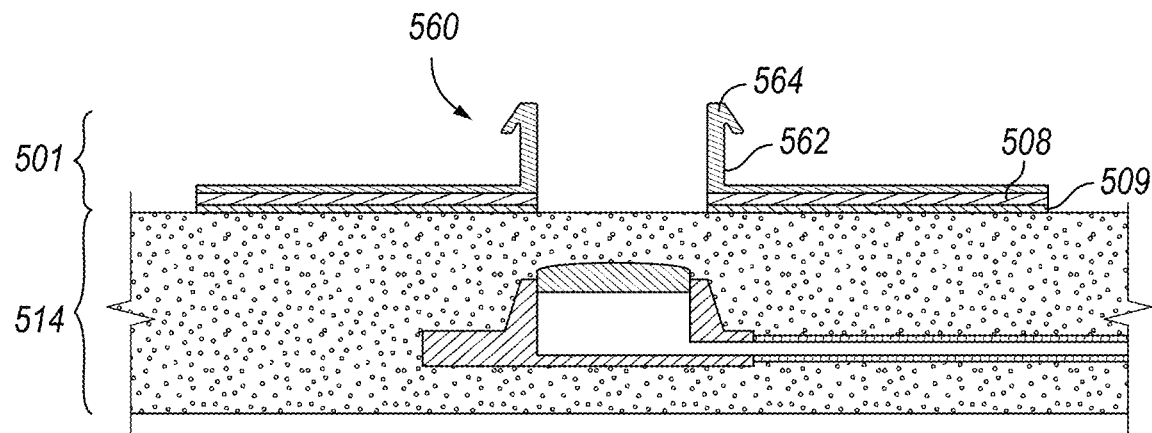
FIG. 5E illustrates a cutaway view of a base plate in relationship to the skin and implanted access port in accordance with example embodiments.
Figure 5F:
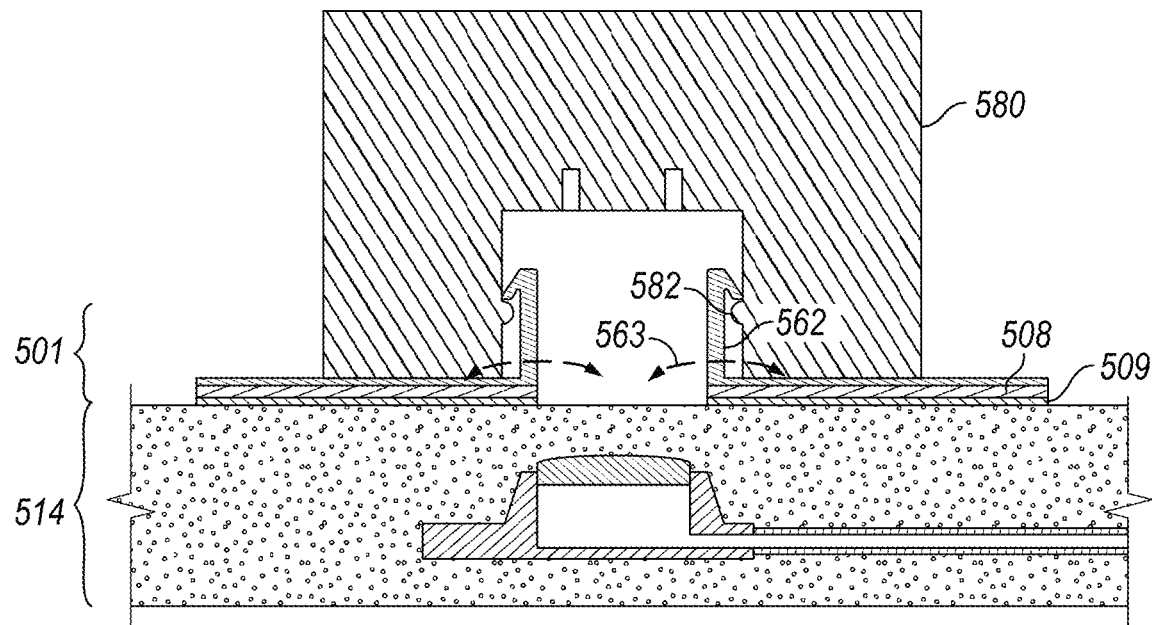
FIG. 5F illustrates a cutaway view of a base plate and medication administration device in relationship to the skin and implanted access port in accordance with example embodiments.
Figure 5G:
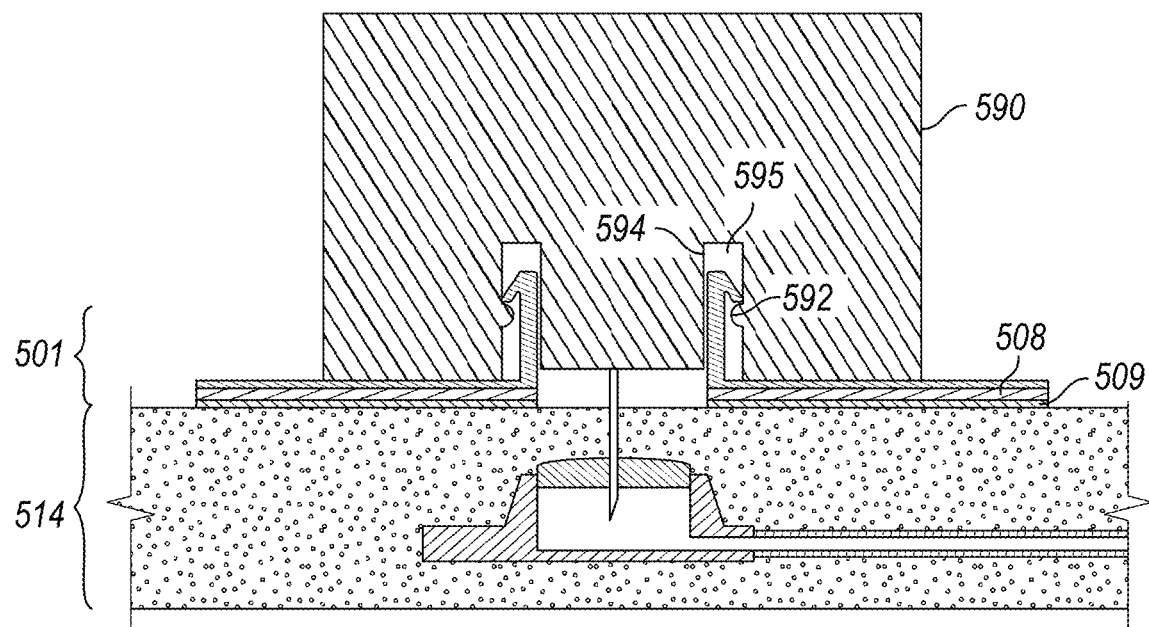
FIG. 5G illustrates a cutaway view of a base plate and medication administration device in relationship to the skin and implanted access port in accordance with example embodiments.
Figures 1, 5H:
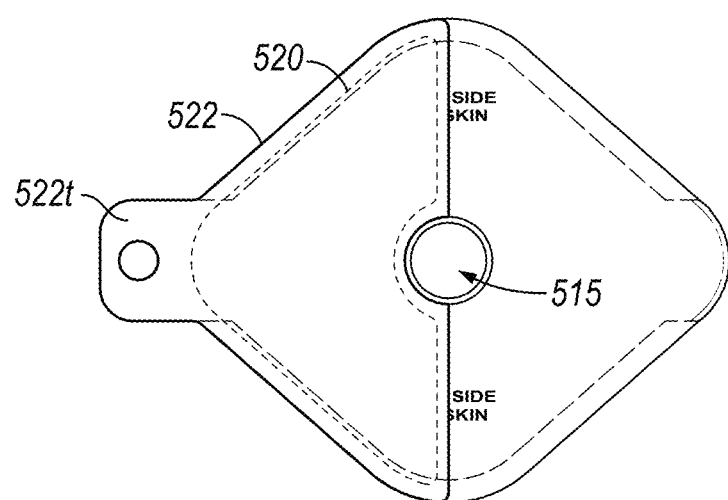
Figures 2, 5H:
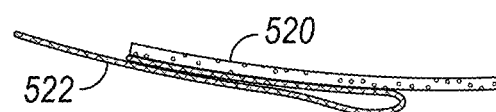

With reference to FIGS. 5H-1 and 5H-2, in some example embodiments, such as but not limited to those with a flexible base plate 501, the flexible base plate 501 may be configured to prevent skin adhesive layer 520 provided on skin side surface 512 from inadvertently sticking to itself and not the skin during removal of the backing paper. With reference to FIG. 5H-1, in an example, an adhesive backing 522 may initially be folded over at or near a centerline (e.g., vertical in FIG. 5H-1) of the skin side surface 512. A pull tab 522t may be provided on the bottom half of the adhesive backing 522 (e.g., that closest to the skin), and configured to urge upward deflection of a portion of flexible base plate 501 away from the skin, allowing progressive exposure of the adhesive layer 520 to the skin while protecting the portion of adhesive layer 520 not yet exposed to the skin. While pulling on the pull tab 522t, a user may apply downward (e.g., Z-axis) pressure to help adhere the exposed portion of adhesive layer 520 to the skin. Thus, the adhesive layer 520 may be applied outwards from a center (e.g., opening 515) towards a periphery/outer contour of the flange and adhere the flange to the skin.

In some embodiments, there may be a symmetrical adhesive layers 520 with adhesive backing 522 on the other side (e.g., in FIG. 5H-1, the right side) of the skin surface 512 to be adhered to the skin through the same or similar manner as that described for the adhesive layer 520 and adhesive backing 522 illustrated in FIGS. 5H-1 and 5H-2.

In some embodiments, the adhesive flange including the adhesive layer 520 and the adhesive backing 522 may include at least one through-hole for a pogo pin to extend therethrough and sense contact with a skin of the living body.

In some embodiments, an adhesive backing with a spiral cut may be provided on adhesive layer 520 and include a "rip-line" connected to a center of the adhesive backing (e.g., nearest the opening). The rip-line may include a pull tab at a periphery of the adhesive backing to be accessible to tugging by a user. As the rip-line is tugged, the spiral cut adhesive backing is tugged from the center, being unwound from inside out to expose the adhesive layer 520 to the skin and adhere thereto, particularly upon pushing in the z-direction by the user. Thus, such removal may be completed circumferentially around opening 515, allowing the base plate 501 to rise up from the skin and then, as the circumference is traversed, allowing the previously exposed portion of adhesive to contact the skin while the next portion is raised from the skin. Thus, the adhesive may be applied outwards from a center (e.g., opening 515) towards a periphery/outer contour of the flange.

Example Method of Accessing an Access Port Implanted in a Living Body

Figure 12:
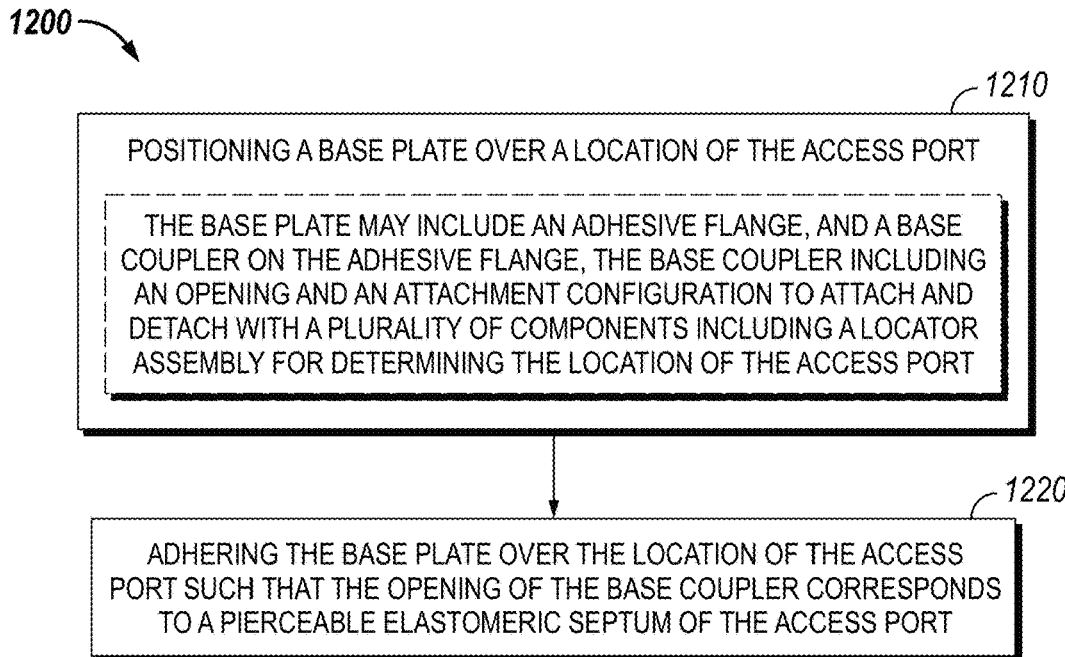
FIG. 12 illustrates a flowchart for an example method of accessing an access port implanted in a living body according to an example embodiment.

With reference to FIG. 12, a method 1200 of accessing an access port implanted in a living body may include positioning 1210 a base plate over a location of the access port. The base plate may include an adhesive flange, and a base coupler on the adhesive flange, the base coupler including an opening and an attachment configuration to attach and detach with a plurality of components including a locator assembly for determining the location of the access port. The method may further include adhering 1220 the base plate over the location of the access port such that the opening of the base coupler corresponds to a pierceable elastomeric septum of the access port.

In some embodiments, the adhering the base plate may further include removing an adhesive backing from an adhesive layer of the base plate. The adhesive backing may be folded over to form a top half in contact with the adhesive layer and a bottom half including a pull tab for removing the adhesive backing from the adhesive layer.

In some embodiments, the method may further include determining, using the locator assembly, the location of the access port.

In some embodiments, the method may further include, after adhering the base plate, detaching the base plate from the locator assembly.

In some embodiments, at least one of the plurality of components may be a medication administration device, and the method further may further include attaching the medication administration device to the base coupler of the base plate.

Base & Device Side Coupler

In some embodiments, device coupler 504 and base coupler 505 may cooperate to removably connect one or more components provided with device coupler 504 to base coupler 505 on base plate 501. Base coupler 505 and device coupler 504 may each comprise some or all parts which cooperate to provide retention, attachment, or detachment of a component attached as described herein; they may also each comprise separate parts of a mating fitting. In some embodiments, cooperation between device coupler 504 and base coupler 505 may be used to removably connect one or more components provided with device coupler 504 to base plate 501.

While base plate 501 is shown in FIG. 5B with a single coupler, one or more base side couplers 505 (e.g., one or a plurality) may be provided if desired. In some embodiments, base plate 501 may be provided with one or more base couplers 505 (e.g., one or a plurality), each corresponding to one or more components (e.g., one or a plurality) that may be attached to, detached from, or retained by the base plate 501. In some embodiments, base plate 501 is provided with one or more base couplers 505, wherein each of the couplers 505 may correspond to a pierceable elastomeric portion of access port 513. In some embodiments, one or more components to be attached to the base plate 501 may be provided with a device coupler 504 corresponding to the base coupler 505 used to attach the component to base plate 501. The plurality of connectors may be provided on the exterior or internal surfaces of base plate 501, or any combination thereto.

Different connectors may be selected or in any combination or order to effectuate the methods described herein. For example, a first base coupler 505 may be configured with an external thread, while a second base coupler may comprise an internal thread, or vice versa. Base coupler 505 may be fitted with an external feature (e.g., threaded coupler as shown in FIG. 5B), or an internal feature (not shown in FIG. 5B). Similarly, device side coupler 504 may be fitted with an internal feature (e.g., threaded coupler as shown in FIG. 5B), or an external feature (not shown in FIG. 5B).

In some embodiments, by way of example, the base coupler may comprise an external thread situated on the external surface of base coupler 505, while a second base coupler may comprise an internal thread situated on the internal surface of device side coupler 504. In an example embodiment, couplers 504, 505 may take complementary cylindrical forms allowing the exterior surface of one to be placed over and flush against the interior surface of the other. For example, as illustrated in FIG. 5B, internal surface 504e of device side coupler 504 may be placed over and flush against the exterior surface 505e of base side coupler 505. The examples of base side coupler 505 and device side coupler 504 depicted herein (and for example in FIG. 5B) are meant to be illustrative, and embodiments are not limited thereto. For example, while the base side coupler 505 is shown having an external thread and the device side coupler 504 is shown as having a corresponding internal thread, embodiments are not limited thereto and the external/internal nature of such threads may be reversed.

Similarly, while a threaded quarter turn lock is shown in the example embodiment of FIGS. 5C-1 to 5C-4, the couplers 504, 505 are not limited to a threaded connection. For example, couplers 504, 505 may comprise any suitable removable connector, the connector being selected for secure connection and protection against inadvertent, undesired, or premature disconnection. A connection may comprise, for example, an internal or external thread (or portion of a thread), a press or interference fit, a taper, a bayonet fitting, a pin and detent, a spring-loaded connection, a locking collar, a snap-fit connection, a hasp, a hook, a barbed fitting, magnetic connection, or other appropriate connection.

Attachment of Components to Base Plate

In some embodiments, one or more components in the locating apparatus may be provided with one or more device couplers 504 for attachment, detachment, or retention on base plate 501 with base coupler 505. In some embodiments, one or more components aside from the apparatus herein may be provided with device coupler 504 for attachment, detachment, or retention on base plate 501 with base coupler 505. In addition to locating assembly 502, components provided with device coupler 504 may include, for example, medication administration sets or drug delivery devices.

In an example embodiment, an adhesive flange 506 with base side coupler 505 may be configured to removably connect one or more components (such as a plurality of components including medication delivery devices and a locating assembly 502) featuring device side coupler 504 to base plate 501. In an example embodiment, the removable connection may comprise one or more of attachment, detachment, or retention of a component featuring device side coupler 504 to a base plate 501 adhered to the skin 510 of a patient 514.

Components provided with the device coupler 504 may be connected to base plate 501 using the base coupler 505 during manufacture (e.g., by preassembly or pre-connection), may be connected by a user of the apparatus (e.g., during one or more use steps with the apparatus or components thereto), or combinations thereof.

In an example embodiment, outer housing 503 containing the locator assembly 502 may be provided with a device coupler 504 and may be removably pre-attached to base plate 501 by way of base coupler 505. In this configuration, locating assembly 502 may be used to locate the port and then adhesively deposit a base plate 501 temporarily onto the skin 510 of a patient over an implanted port 513, whereupon locating assembly 502 is then removed from the base plate 501.

In some embodiments, a medication delivery device, such as a needle assembly, autoinjector, wearable injector, or other drug delivery device may be attached to the base plate 501 via couplers 504, 505 gaining straightforward and accurate access to the located port 513 and particularly the pierceable elastomeric septum 513s. Such an example embodiment may be advantageous when the duration of medication delivery is comparatively long (e.g., minutes to hours), and both location of the port and retention of the drug delivery device are required.

In some embodiments, a medication delivery device, such as a needle assembly, autoinjector, wearable injector, or other drug delivery device may be directly inserted through opening 515 in base plate 501 without use of couplers 504, 505 gaining straightforward and accurate access to the located port 513 and particularly the pierceable elastomeric septum 513s. This example embodiment may be advantageous when the duration of medication delivery may be comparatively short (e.g., seconds to minutes), location of the port is required, and retention of the device is not required.

In some embodiments, couplers 504, 505 may be selected, configured, or designed taking into account the forces and torques applied during use of the apparatus and the components attached thereto, including the sequence of attachment and detachment, the size, weight, or structure of the device to be attached to base plate 501, the duration of retention on the base plate 501 (e.g., duration of medication delivery to port 513), movement or operation of a device attached to base plate 501, the degree of anticipated patient movement with base plate 501 on the skin 510, or other relevant factors. Multiple couplers may be selected if desired, and each coupler 504, 505 may be independently selected if desired. For example, a comparatively less robust coupler may be used to removably connect a lightweight locating assembly 502 retained briefly while a port is located, while a comparatively more robust coupler may be selected to attach a heavier device retained for several hours, such as a drug delivery device.

Materials may be selected for couplers 504, 505 based on the nature of the connection. In some examples, such as a threaded or bayonet fitting, a more rigid material may be selected; in the case of a press fit, interference fit, snap fit, or snap over connection, a material with balanced plastic and elastic properties may be selected. A threaded connection may optionally be fitted with one or more buttresses or stops to prevent over-rotation during attachment or detachment, thereby reducing torques or forces upon base plate 501 or adhesive flange 506. Similarly, detents may be provided on either or both of couplers 504, 505 to provide tactile feedback to a user of the apparatus during attachment or detachment of a device to base plate 501, or to prevent inadvertent detachment of a device from base plate 501. Moreover, the interface between couplers 504, 505 may be selected to prevent inadvertent detachment of components attached to base plate 501 and base plate coupler 505 with a device side coupler 504, as by vibration, movement, or other factors.

In some embodiments, while base side coupler 505 on a flexible base plate 501 may be a threaded or other connection, as described herein, embodiments are not limited thereto. Indeed, couplers (e.g., device couplers 504 and/or base coupler 505) may be designed to take advantage of the underlying flexible material characteristics of the base coupler 505.

For example, with reference to FIG. 5E, in place of a threaded connection, base coupler 505 may be provided with a slotted, barbed configuration 560 including a plurality of flexible fingers 562 that serve as a flexural connection that is "easy on, easy off" when, for example, a locating assembly 502 or other device is attached/detached. In some embodiments, the slotted, barbed configuration may include the plurality of fingers 562 in a circular configuration and equally spaced in a circumferential direction around opening 515 with a plurality of slots therebetween. In some embodiments, the fingers 562 may be made of an elastic material and may flex in opposite radial directions as shown by arrows 563 (see FIG. 5F). The flexibility of the plurality of fingers 562 may be based on an elastic modulus of the elastic material. Each of the fingers 562 may include, on a distal end, a barb 564. In some examples, the barb 564 may include a hook shape for interacting with a protruding groove 582 discussed with reference to FIGS. 5F-5G. In some embodiments, this configuration 560 may take the place of the threaded coupling of the couplers 504, 504, as described herein.

With reference to FIG. 5F, a first device 580, such as a port locating assembly 502 or other component, may be provided with a cooperating device side coupler feature (e.g., a circumferential protruding groove 582 protruding from a sidewall of the first device 580) that may be pushed onto the barbed fitting provided by the barbs 564 of the plurality of fingers 562, thereby retaining the first device 580 in place with the base plate 501. In an example configuration, the flexure is a "snap over" but is only retained by friction and the groove. Such a configuration with the port locating assembly 502 attached may allow location of an access port and attachment of the base plate 501 to the skin as described herein.

In example embodiments, without an inner "buttress" provided by the first device 580 interior to the fingers 562, the fingers may freely flex inward such that a user may easily remove the first device 580 from the base plate 501 (e.g., once the base plate 501 is adhered to the skin). For example, for easy removal, a port locating assembly 502 as the first device 580 may not include such a buttress so that it may be easily detached from the base plate 501 once the base plate 501 is located and adhered over an access port. Likewise, the first device 580 may also be easily attached to the base plate 501 as needed. The ease of removal and attachment of the first device 580 from/to the base coupler 505 of the base plate 501 may be tuned by the size and contour of the barbs, the size and contour of the protruding groove 582, a spacing between the fingers 562 and the device side coupler feature, including the sidewall and protruding groove 582, and/or an elastic modulus of the fingers.

With reference to FIG. 5G, a second device 590, which may be a medication delivery device such as an on-body injector (OBI) (e.g., a wearable injector) or needle assembly (e.g., a needle assembly 700 as described herein) may be attached to the barbed configuration 560 of the base coupler 505, for example by pushing it on and having the fingers 562 be retained by the groove. For example, the second device 590 may be attached once the access port has been located by a first device 580 and first device 580 is detached. In some embodiments, the second device 590 may include a central stabilizing structure (e.g., a tapered buttress 594) that prevents substantial inward flexing of the fingers 562, and thus a higher degree of retention of the second device 590 to base plate 501 once connected. For example, the buttress 594 may constrain movement of the fingers 562 as compared to an unbuttressed configuration.

The degree of retention may be calibrated to either prevent (e.g. restrict) or resist removal. For example, the taper of the buttress 594, the elastic modulus of the fingers 562, the clearance between the fingers 562 in an annular opening 595 of the second device 590 provided between the buttress 594 and a sidewall including the protruding groove 592, and/or the size and contour of the barbs 564 may impact the degree of retention to either prevent or resist removal of the second device 590 from the base plate 501.

In an example embodiment where the degree of retention is calibrated to prevent removal, this may enable a used apparatus (e.g., a second device 590 including an OBI or needle assembly) to be removed along with the base plate 501 at the conclusion of medication delivery as a single unit. In an example embodiment where the degree of retention is calibrated to resist removal, this may provide improved protection against inadvertent disconnection of a second device 590 attached to the base coupler while still preserving the ability to remove the used second device 590 from base plate 501 and attach another device (e.g., a second needle, or OBI device equipped with a device side coupler, for subsequent administration of the same and/or a different medication) then or at a later time.

Buffer Layer

In some embodiments, one or more buffer layers 508 may be permanently interposed between skin side surface 512 and device facing surface 511. Buffer layer 508 may be included to provide desirable properties based on the conditions of use and may be comprised of any number of materials suitably attached to each other. In some embodiments, buffer layer 508 may also comprise device side layer 507 if, for example, one is not provided in an embodiment of the apparatus. Any materials in buffer layer 508 may vary in thickness, orientation, color, shape, barrier properties, antimicrobial properties, absorbent or repellent properties, or other characteristics. For example, with an adhesive flange provided to a patient receiving hazardous medications (e.g., antineoplastics, teratogens), buffer layer 508 may include a barrier material to hazardous drugs, such as nitrile or natural rubber latex, or a barrier designed to prevent aerosolization of medication administered through access port 513. In another example, buffer layer 508 may include a soft, compliant foam (e.g., polyurethane or hydrogel foam) to cushion the skin when one or more devices is attached to the base plate 501, such as a rigid infusion needle assembly that may cause skin irritation or pain to a patient.

Base plate 501 and particularly adhesive flange 506 may be subjected to various dynamic stresses and strains, particularly as the skin 510 of a patient wearing base plate 501 moves, or devices (e.g., locator assembly, needle assembly, or drug delivery device) are attached or detached to base plate 501 via device side coupler 504 and base side coupler 505. Buffer layer 508 may act as a strain relief between a component attached with a device side coupler 504 to the base plate 501 with base coupler 505, reducing the risk of accidentally dislodging the component by distributing any load, forces, or stresses evenly to adhesive flange 506. Strain relief provided by buffer layer 508 may advantageously prevent patient discomfort when a device with a needle is attached to base plate 501 and the needle is inserted into port 513 for delivery of a medication.

For example, buffer layer 508 may be configured to allow comparatively more axial or torsional flexibility in a first direction or dimension, and comparatively less axial or torsional flexibility in a second direction or dimension, as with a material of sufficient thickness and balanced flexibility, extensibility, or rigidity. One or more materials comprising buffer layer 508 may be selected for porosity, viscosity, density, stiffness, flexibility, cushioning, or other relevant factors, and may include, for example, open or closed cell foams or hydrogels. Different materials comprising buffer layer 508 may also be used in different orientations, thicknesses, contours, or geometries in one or more portions of the buffer layer, and may need not comprise a full layer of a single material.

In other words, buffer layer 508 may be configured to selectively resist or permit forces or torques in one or more directions. In some embodiments, adhesive flange 506, once attached to the skin 510, may be configured to permit relative motion or flexure in one or more directions between adhesive flange 506 and a component attached thereto by couplers 504, 505. In some embodiments, adhesive flange 506, once attached to the skin 510, may be configured to restrict or resist relative motion or flexure in one or more directions between adhesive flange 506 and a component attached thereto by couplers 504, 505.

For example, a wearable injector with device side coupler 504 may be rotated in a clockwise manner for attachment to base side coupler 505 and rotated in an anti-clockwise manner, detaching it from base side coupler 505. It may be desirable to permit clockwise torques, but provide comparatively higher resistance to anti-clockwise torques that could cause inadvertent removal of the device from base plate 501. In some embodiments, adhesive flange 506, once attached to the skin 510, may be configured to restrict or resist relative motion or flexure between adhesive flange 506 and a component attached thereto by couplers 504, 505 in a first direction, and permit relative motion or flexure between adhesive flange 506 and a component attached thereto by couplers 504, 505 in a second direction.

Adhesive Flange Support

Referring to FIGS. 5C-1 to 5C-4, in an example embodiment, adhesive flange 506 may project in an outwardly facing contour from the base side coupler 505 in one or more directions and/or dimensions, also being configured to attach base side coupler 505 to the skin 510 in proximity to an access port 513 implanted in patient 514. The outwardly facing contour, and particularly the radially outward contour of adhesive flange 506 may take any outer shape, for instance, circular, elliptical, square, rectangular, diamond shape (e.g., outer contour 533, star-shaped, other shapes, or combinations thereof. The outward projection may alternatively, for example, suggest the shape of a component later attached to the base plate 501 such as the outer contour of the locating assembly 502, needle assembly, or a drug delivery device, or another shape. Adhesive flange 506 may also be contoured to ensure appropriate skin attachment despite unevenness resulting from a raised skin prominence caused by an implanted port underneath. In some embodiments, adhesive flange 506 may have a curved shape so that only the center portion may be in contact with the skin, while the outer edges are higher. In some embodiments, sections of outer contour 533 may comprise portions of consistent and/or varying wall thicknesses (e.g., if injection molded). For instance, the portion of outer contour 533 may have comparatively thinner sections far from opening 515, and comparatively thicker sections closer to opening 515 (i.e., tapering from thinner to thicker towards port opening 515). Such features may improve resistance to inadvertent removal of adhesive flange 506.

Adhesive flange 506 or a portion thereof may also be provided one or more openings 515 situated on the interior of the flange surface or one of its components. In some embodiments, an opening 515 in adhesive flange 506 may be provided to visualize an implanted port site, to visualize the skin over an implanted port, or to accommodate a medication delivery device (which may also be referred to herein as a medication administration device). In an example, the opening 515 may comprise a circular profile, with a center point and desired diameter. For example, opening 515 may be a relatively large diameter, allowing for unobstructed access to the skin over the center of an implanted port. In another example, opening 515 may be a relatively small diameter, allowing for unhampered insertion of an injection needle through the flange. In some embodiments, the opening 515 of adhesive flange 506 may align with an opening of the base coupler 505. In some embodiments including one or more port sensors 204, the one or more port sensors 204 may sense an aspect of the access port through the openings of the adhesive flange 506 and the base coupler 505. In some embodiments including one or more skin sensors 205, the one or more skin sensors 205 may sense a proximity and/or contact with skin through the openings of the adhesive flange 506 and the base coupler 505. In an example, at least one of the one or more skin sensors 205 may include a pogo pin. However, embodiments are not limited thereto, and additionally and/or alternatively, in some embodiments, one or more skin sensors 205 (which may include a pogo pin) may extend through and/or sense through a respective one or more additional through-holes (e.g., openings) in the base plate 501 to sense contact or proximity to the skin. In some embodiments, the base plate 501 including the adhesive flange 506 may include a plurality of openings respectively corresponding to a plurality of skin sensors 205 for the skin sensors 205 to sense the skin therethrough.

In some embodiments, one or more openings 515 may be provided to permit proper operation of one or more sensors that would otherwise be obstructed by one or more aspects of the adhesive flange 506 or components therein. Openings to permit proper sensor operation could, for example, comprise a selective removal, contour, shaping, thinning, stamping, compression, or other forming, shaping, or removal processes of one or more materials in the adhesive flange 506.

Openings may be provided during manufacture of the adhesive flange, during operation of the apparatus or other components, or combinations thereto. During manufacturing, openings may be created by die cutting, punching, perforation, laser cutting, water jet cutting, molding, or other suitable processes. In some embodiments, opening 515 may be formed when a drug delivery device coupled to base plate 501 advances a needle through adhesive flange 506 from device side surface 511 to skin side surface 512, puncturing flange 506 and subsequently the skin 510 and/or port 513.

In some embodiments, adhesive flange 506 may be provided with supporting features 530 on either or both of the skin side surface 512 and the device side surface 511. Supporting features may be included to prevent inadvertent or undesired adherence of skin side surface 512 to a patient's skin or to another portion of the adhesive on skin side surface 512 when an adhesive is exposed (e.g., when the release liner is removed). Supporting features 530 may also be used to stiffen adhesive flange 506 and improve the ability of a user to attach the adhesive to the skin 510.

Like the adhesive flange, supporting features 530 may be low-profile planar elements, for example, paper, polymer, or metal elements, or combinations thereof. In some embodiments, supporting features 530 may be contoured away from the generally planar surface of an adhesive flange 506, situated or applied to bend the adhesive flange upwards at the periphery (e.g., outward edges of flange 506 relative to opening 515) and away from skin side surface 512 and the skin 510 prior to application or ease removal of the liner. For example, the polymer or metal supporting features 530 may be molded or shaped with a contour, or the paper elements may be applied to the surface with adhesive flange deformed upwards from the skin side surface 512 at the time of manufacture, thus temporarily deforming the periphery of adhesive flange 506 away from skin side surface 512.

Supporting features may be removably attached to the skin side surface 512 or device surface 511. Supporting features 530 may prevent wrinkling of the adhesive flange 506 that may compromise the sterile barrier between the patient's skin and the external environment (e.g., air, touch contamination) or may be configured to allow a user to progressively apply adhesive on flange 506 to the skin. For example, adhesive flange 506 may be adhered to skin 510 first nearest opening 515, and then outwardly towards the periphery of adhesive flange 506.

Device Side Surface & Indicia

In some embodiments, device side surface 511 of base plate 501 may be provided with markings or indicia to give users instructions regarding proper use of aspects of or components of the apparatus, one or more use steps for the apparatus, or information regarding the apparatus or its component(s).

In some embodiments, indicia may comprise an outline of a locating assembly 502 or the outer housing 503 thereof to correctly orient the apparatus during attachment or detachment of a device using couplers 504, 505. Indicia may also comprise one or more of icons, graphics, text, use step numbers, lot code information, expiration data information, medication information, instructional text, warnings, cautions, information regarding compatible and/or incompatible products with the apparatus, or other relevant information to a user of the apparatus.

Referring to FIG. 5C-1, the device side surface 511 may be provided with one or more of graphic indicia 531g, text indicia 531t, icon indicia 531i, or outline 503o. Graphic indicia 531g may indicate a motion, such as rotation, required to properly use the apparatus. Text indicia 531t may indicate numeric order of use steps, an instructional text to a use of the apparatus, or other textual information (e.g., a part number, lot number, or expiration date). Icon indicia 531i may be presented to indicate manipulation of the apparatus, as in the example icon shown to remove the adhesive liner on skin side surface 512. Other icons, graphics, text elements, or outlines may be presented based on the situation in which the apparatus is used.

In some embodiments, indicia, such as outline 503o, may be visually suggestive of (e.g., taking the shape of; slightly smaller or larger than) the outline of outer housing 503, and indicate a correct (or incorrect) orientation of the outer housing relative to the adhesive flange 506 or base plate 501, enabling a user to correctly orient the components of the apparatus during attachment or detachment of a device using couplers 504, 505.

Referring to FIG. 5C-2, the device side surface 511 may be provided with one or more of graphic indicia 535g, first outline 537, and second outline 538. Graphic indicia 535g, 536g may indicate a motion, such as rotation, required to properly use the apparatus. First and second outlines 537, 538 may be visually suggestive of (e.g., taking the shape of; slightly smaller or larger than) the outline of outer housing (e.g., 503), and indicate one or more orientations of the outer housing in various steps of connection to the adhesive flange 506 or base plate 501 enabling a user to correctly orient the components of the apparatus during attachment or detachment of a device using couplers 504, 505.

By way of example, first outline 537 may correspond to the position of the outer housing when advanced onto base plate 501 in a direction towards the skin. The outer housing may be then rotated clockwise, as indicated by graphic indicia 535g, 536g and text indicia 535t, 536t. Continuing the example, the second outline 538 may corresponds to the position once the outer housing is attached to base plate 501 enabling a user to correctly orient the components of the apparatus during attachment or detachment of a device using couplers 504, 505.

Referring to FIG. 5C-3, the skin side surface 512 may be provided with one or more indicia, as described previously with respect to the device side surface 511. Although text indicia 539t indicating proper orientation of adhesive flange 506 relative to the skin is provided by way of example, any or all of graphic, iconic, or textual indicia may be provided on either skin side surface 512 or device side surface 511.

Referring to FIG. 5C-4, in some embodiments, the device side surface 511 may be provided with one or more indicia arranged to be selectively concealed or revealed to a user of the apparatus based on one or more components attached to the base plate 501. Selective concealment or revealment may have an advantage of communicating information to a user of the apparatus as described previously while avoiding the opportunity for the user to be confused by multiple sets of information visible simultaneously. For the purposes of illustration, graphic indicia 540g and 541g and text indicia 540t and 541t along with a first outline 542 and second outline 543 are provided.

First outline 542 may correspond to the position of the outer housing when advanced onto base plate 501 in a direction towards the skin. Graphic indicia 540g and text indicia 540t may be visible, indicating the correct direction of assembly onto base plate 501. However, placement of the outer housing over outline 542 may conceal graphic indicia 541g and text indicia 541t, which indicate the removal steps. The outer housing may then be rotated clockwise, as indicated by graphic indicia 540g and text indicia 540t. Continuing the example, the second outline 543 may correspond to the position once the outer housing is attached to base plate 501, enabling a user to correctly orient the components of the apparatus during attachment or detachment of a device using couplers 504, 505. Rotation of the outer housing clockwise thus may conceal graphic indicia 540g and text indicia 540t, and expose graphic indicia 541g and text indicia 541t, which indicate the removal steps.

Other variations may be possible. In some embodiments, indicia may be arranged on device side surface 511 to be visible to a user of the apparatus when a first component is attached to base plate 501, and then hidden when a second component is later attached to base plate 501, both by way of couplers 504, 505. The inverse is also possible. Indicia may be arranged on device side surface 511 to be hidden from a user of the apparatus when a first component is attached to base plate 501, and then revealed when a second component is later attached to base plate 501, both by way of couplers 504, 505.

Selectively concealed indicia may be particularly advantageous when a component is pre-assembled to a base plate as described herein. In some embodiments, indicia (e.g., 531g,i,t, 540g, 540t, 541g, 541t) provided on the device side surface 511 may be initially revealed by a first component pre-attached to base plate 501, and subsequently revealed to a user of the apparatus when the first component is removed from the base plate 501 and base side coupler 505.

In some embodiments, one or more indicia (e.g., 531g,i,t, 540g, 540t, 541g, 541t) provided on the device side surface 511 may be initially concealed by a locating assembly 502 pre-attached to base plate 501, and subsequently revealed to a user of the apparatus when the locating assembly 502 is removed from the base plate 501 and base side coupler 505. By way of example, the first component may be locating assembly 502 pre-attached to base plate 501 by way of couplers 504, 505, the second component may be a drug delivery apparatus, and one or more concealed indicia (e.g., 531g,i,t, 540g, 540t, 541g, 541t) may comprise attachment instructions for the drug delivery apparatus.

Removal of Port Locator Assembly & Port Access Via Retained Base Plate & Coupling(s)

FIG. 5D-1 shows locating assembly 502 removably connected to base plate 501, both adhesively and temporarily deposited onto the skin 510 of a patient over an implanted port 513 with opening 515 positioned over a pierceable portion of elastomeric septum 513s, all as previously described.

Now referring to FIG. 5D-2, locating assembly 502 is then removed from the retained base plate 501 by disconnecting device side coupler 504 from base side coupler 505. In the illustrative example of FIG. 5D-1 to 5D-3, couplers 504 and 505 may form a threaded connection, and disconnection may take place by turning locating assembly 502 in a counter-clockwise direction 551, so as to unthread locating assembly 502 from base plate 501.

In some embodiments, opening 515 in base plate 501 may remain positioned over a pierceable portion of elastomeric septum 513s after removal of locating assembly 502. Referring to FIG. 5D-3, unlocked locating assembly 502 may be removed (for example, after the disconnecting described by example with reference to FIG. 5D-2) by grasping in the hand and pulling in a direction 552 away from retained base plate 501. In some embodiments, base plate 501, being retained on the skin 510, may substantially resist torques (e.g., 551) or forces (e.g., 552) caused by removal of locating assembly 502, maintaining opening 515 to be substantially positioned over a pierceable portion of elastomeric septum 513s.

Removal of locating assembly 502 may expose the interior of base coupler 505 and opening 515, which may be configured to subsequently allow access to an aspect of an implanted port 513 (e.g., a pierceable portion of elastomeric septum 513s) located in accordance with the apparatus and methods described by example herein.

Such a configuration may allow visibility of skin 510 over the port 513 (e.g., as for skin preparation or site marking) for insertion of a needle of a medication delivery device into a portion of a pierceable elastomeric septum 513s of an implanted access port 513. A medication delivery device may, by way of example, be any device with an injection needle, such as a hollow-bore percutaneous needle with a bent cannula and deflected, sharpened end (e.g., a Huber needle), or a needle assembly, autoinjector, wearable injector, all as described herein. Additionally, medication delivery devices other than those described herein may be used, and other procedures (e.g., site marking, site sterilization, blood draws, blood donations, blood transfusions, hemodynamic monitoring, contrast administration for imaging studies, dialysis) may be performed through opening 515 on an aspect of an implanted port 513 or a pierceable portion of elastomeric septum 513s.

In some embodiments, access to the port 513 or pierceable port septum 513s may take place via opening 515 with connection to base coupler 505. In some embodiments, access to the port 513 or pierceable port septum 513s may take place via opening 515 without connection to base coupler 505.

In the example embodiment of FIGS. 5D-1 to 5D-3, base coupler 505 is shown taking an annular shape disposed substantially around or on top of an implanted port 513 and particularly a pierceable portion of an elastomeric septum 513s, located in accordance with embodiments described herein. In some embodiments, the opening 515 may comprise an interior annular center disposed over a portion of a pierceable elastomeric septum of an implanted port. For example, the inner diameter of the annulus may be approximately the same diameter as a pierceable elastomeric port septum. However, the shape of opening 515 may not need to be annular or circular; for example, it may be square, rectangular, elliptical, or other geometry, such as the geometry taken by the outer housing of the port or by a pierceable elastomeric port septum of the port. Further, there may be multiple openings, each with different shapes and configurations. Further, each of a cooperating base coupler 505 a device coupler 504 may not need to have the same opening shape; different openings may be used for each.

Skin Preparation

In some embodiments, the interior opening of a base plate disposed on the skin as described herein may be configured to allow insertion of a component provided with a shape cooperating with the interior opening shape to prepare the skin, sterilize the skin, or mark the skin.

Figures 1, 6A:
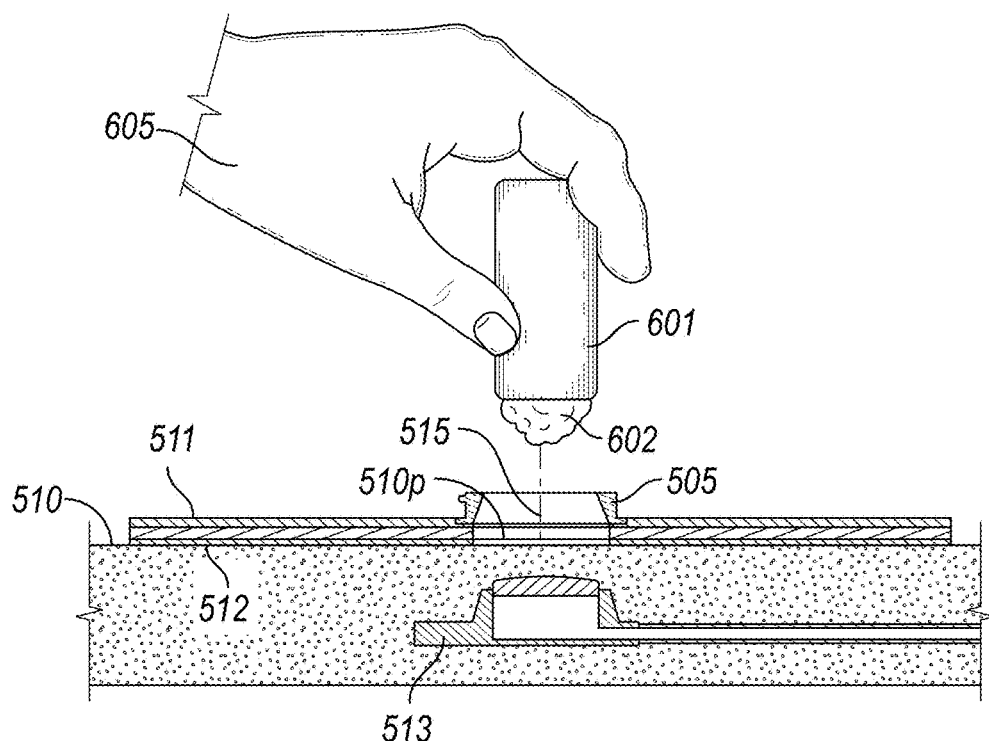
Figures 2, 6A:
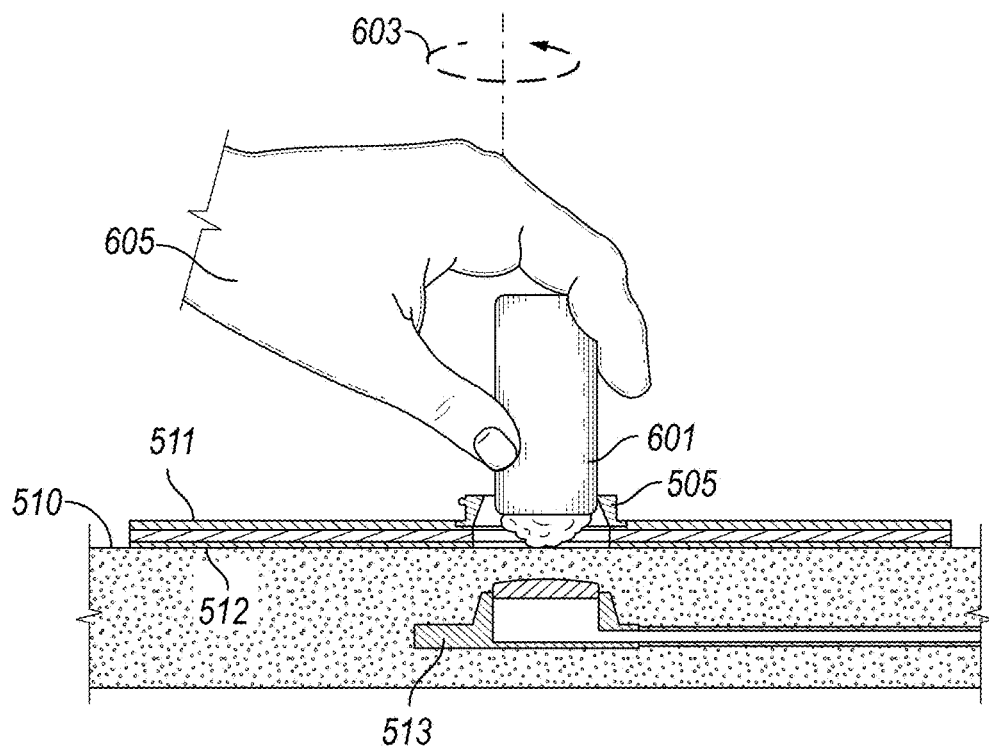

As shown in FIGS. 6A-1 and 6A-2, in some embodiments, a sterilizing swab 601 may be configured to be placed through the opening 515 of base plate 501 disposed on skin 510 for the purpose of preparing (e.g., sterilizing) skin in proximity to an implanted port 510p. Swab 601 may be rigid to be more easily handheld by a user 605 such as a healthcare provider or patient, and may have a compliant end 602, for example, out of a foam material, that is compressible when rotated 603 relative to or pressed against the skin. A sterilant may be disposed on swab end 603 including, for example, alcohol, iodine, povidone-iodine, octenidine dihydrochloride, chlorhexidine gluconate, or other appropriate sterilant. In some embodiments, the sterilant on swab 601 may have persistent antimicrobial activity.

Figures 1, 6B:
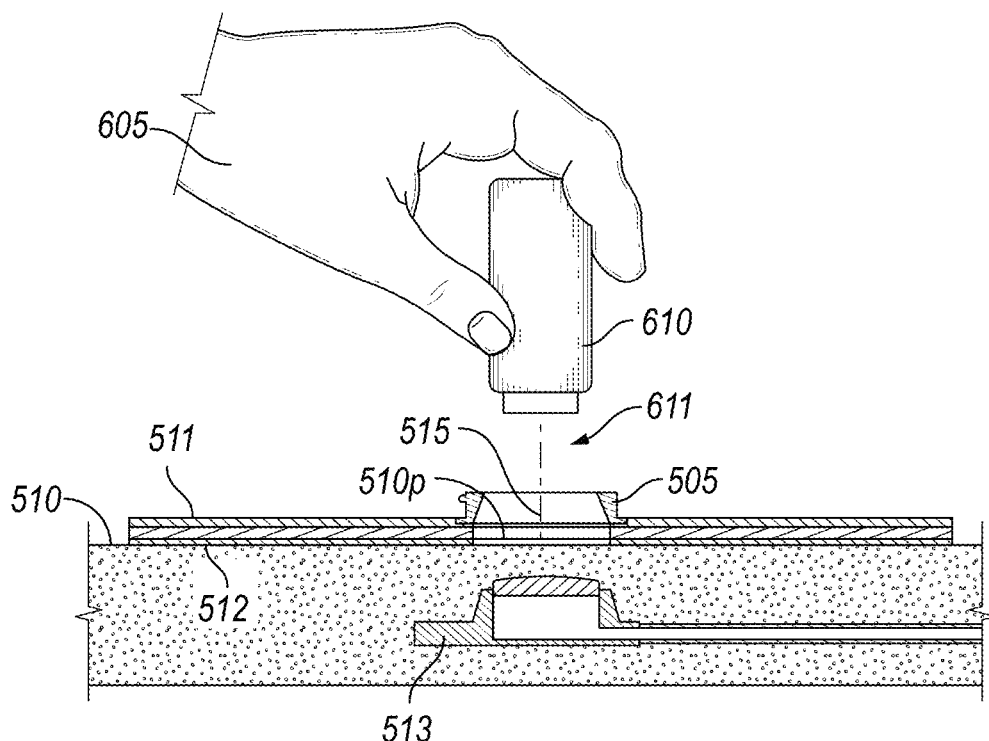
Figures 2, 6B:
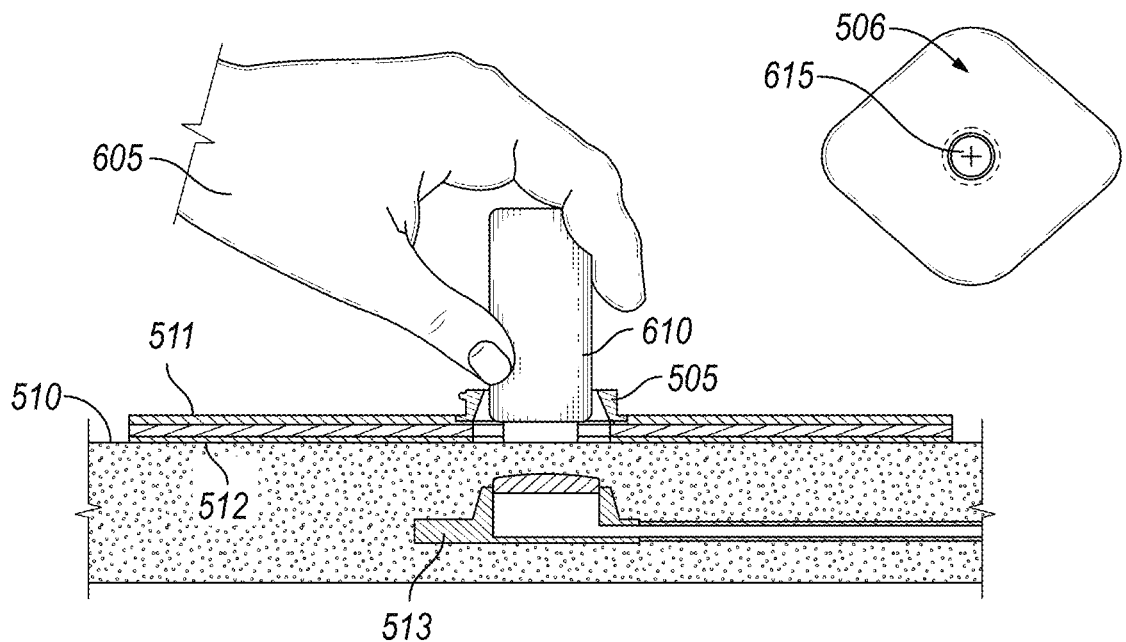
Figure 6C:
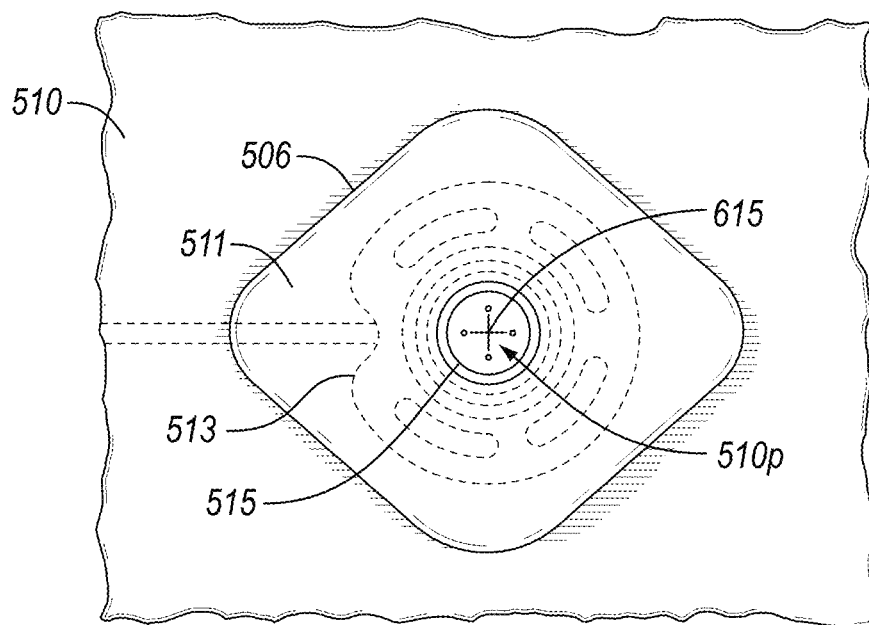
FIG. 6C is a top view of marked skin indicating the location of an implanted port in conjunction with a base plate, all in accordance with example embodiments.

As shown in FIGS. 6B-1 and 6B-2, in some embodiments, a marking device 610 may be configured to be placed through the opening 515 of base plate 501 disposed on skin 510 for the purpose of marking the skin in proximity to an implanted port 510p or a portion of a pierceable elastomeric septum. Marking device 610 may also have an end 611 with an ink or dye, such as gentian violet, methylene blue, or other skin-compatible marking substances. As seen in FIG. 6C, such a marking device, may make, for example, a dot, cross-hair, or circular mark 615 upon the skin 510. Marking device 610 may be optionally sterile to preserve the sterility of a prepared site (e.g., after using sterilizing swab 601).

In an example embodiment, the sterilizing swab 601 or marking device 610 may be unretained by the base coupler 505 and instead may be aligned by and guided into the interior opening 515 then axially advanced towards the skin 510, particularly the skin 510 in proximity to the port. However, in some embodiments, marking device 610 or sterilizing swab 601 may also be provided with a device coupler (not shown) if it may be required for removable connection to base plate 501.

Example Embodiment: Medication Administration with Retained Base Plate

With reference again to FIGS. 5D-1 to 5D-3, and for purposes of describing the following example embodiment, let it be assumed that an access port has been located as described previously, locating assembly 502 is removed from base plate 501, base plate 501 is situated with base coupler 505, and opening 515 is situated on the skin 510 over a pierceable portion of elastomeric septum 513s, all as previously described. Additionally, the skin 510 may have been marked and/or sterilized as described with reference to FIGS. 6B-1 and 6B-2. One or more medication delivery devices (which may be referred to herein as one or more components, the locator assembly 502 being another one of the components) provided with a device side coupler 504 may be subsequently attached to the retained base plate 501 and deliver medications to a patient through the skin 510 and septum 513s. For example, a user may subsequently attach one or more different devices with device side coupler 504 to the base plate coupler 505 and thus the base plate 501, thereby gaining access to the skin 510, access port 513, or port septum 513s, for example, with an injection needle.

In some embodiments, the device side coupler 504 provided in a medication delivery device may be configured to cooperate with the base side coupler 505 in the retained base plate 501 to removably attach the medication delivery device to the retained base plate 501 to deliver medications to a patient. In some embodiments, retained base plate 501 may position an attached medication delivery device over one or more of opening 515 or a pierceable portion of one or more elastomeric septa 513s contained in access port 513. In some embodiments, attaching a medication delivery device provided with a device side coupler 504 to the base side coupler 505 in a retained base plate 501 may allow one or more medications to be delivered through opening 515 through the skin 510, and into septum 513s of access port 513.

In some embodiments, a medication delivery device provided with a device side coupler 504 for cooperation with base side coupler 505 in a retained base plate 501 may comprise one or more medication delivery devices, such as a needle assembly, a wearable injector (or infuser), or an autoinjector, each as described for example embodiments below, and/or other devices provided with device side coupler 504 that will be apparent to those skilled in the art.

Example Embodiment: Medication Administration with Retained Base Plate and Needle Assembly With reference again to FIGS. 5D-1 to 5D-3, and for purposes of describing the following example embodiment, let it be assumed that an access port has been located as described previously, locating assembly 502 is removed from base plate 501, base plate 501 is situated with base coupler 505, and opening 515 is situated on the skin 510 over a pierceable portion of elastomeric septum 513s, all as previously described. Additionally, the skin 510 may have been marked and/or sterilized as described with reference to FIGS. 6B-1 and 6B-2. One or more medication delivery devices provided with a device side coupler 504 may be subsequently attached to the retained base plate 501 and deliver medications to a patient through the skin 510 and septum 513s. For example, a user may subsequently attach one or more different devices with device side coupler 504 to the base plate coupler 505 and thus the base plate 501, thereby gaining access to the skin 510, access port 513, or port septum 513s, for example, with an injection needle.

Needle Assembly

Figure 7A:
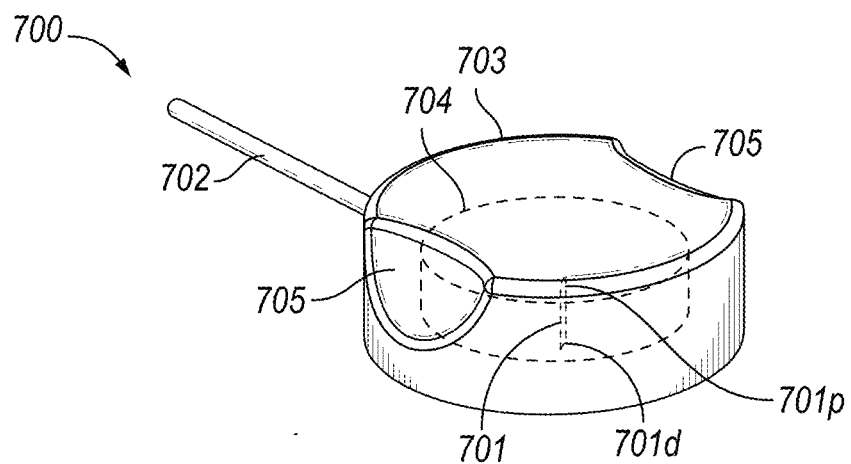
FIG. 7A illustrates a perspective view of a needle assembly for use with a base plate according to an example embodiment.

FIG. 7A illustrates an example embodiment of a medication delivery device comprising an injection needle assembly. In some embodiments, an injection needle assembly 700 may be provided with device side coupler 504 and may be removably attached to base side coupler 505 of base plate 501 retained on the skin 510 once outer housing 503, locator assembly 502, and device side coupler 504 are detached from base plate 501. For example, needle assembly 700 may be removably attached to base plate 501 after removal of outer housing 503 containing the locator assembly 502 from base plate 501 as described previously.

In some embodiments, attachment of needle assembly 700 to a base plate 501 may precede medication delivery to a patient via the access port 513. In some embodiments, attachment of needle assembly 700 to base plate 501 may position a needle 701 within the assembly to puncture the patient's skin 510 and elastomeric septum 513s, placing the needle assembly 700 and particularly tubing set 702 in fluidic communication with implanted access port 513.

Needle Assembly Housing+Materials

In some embodiments, a needle assembly 700 may comprise a needle 701, a tubing set 702, and device side coupler 704, all contained in housing 703. Device side coupler 704 may be in accordance with an example embodiment as previously described (for example, device side coupler 504); and any of the details related to the device side coupler herein may be applied to the example embodiments of needle assembly 700.

Needle 701 may be any suitable needle for piercing an elastomeric port septum used with the apparatus. Needle 701 may be a long, tubular cross-section with a proximal end 701p in fluidic communication with tubing set 702 and sharpened distal end 701d. Medication may be administered to a patient through tubing set 702 and needle passage from proximal end 701p to distal end 701d. When placed in an access port, fluid may be further communicated from the distal end 701d into the access port through the skin and then from the port septum through the port catheter to the patient.

The material of needle 701 may be siliconized rigid medical grade stainless steel, and the sharpened distal end 701d of needle 701 may optionally be a non-coring design, such as a hollow-bore percutaneous needle with a bent cannula and deflected, sharpened end (e.g., a Huber needle), or may have a conventional point with one or more bevels. A portion of needle 701 may be substantially straight or may be bent along the long axis of the needle to removably penetrate an implantable port. The needle and/or needle point may optionally be protected after use by a safety mechanism to protect a user of the needle assembly 700 against needlesticks and bloodborne pathogen exposure.

Tubing set 702 may be provided with a connection fitting such as a luer or Luer-Lok® connector, and may be fashioned from one or more of silicone, PVC, PVC without DEHP, EVA, HDPE, LDPE, TPU, PTFE, a cyclic olefin polymer or copolymer, a fluoropolymer, or other suitable flexible materials or combinations thereof. In an example embodiment, tubing sets may be extruded but may be formed by other means that provide sufficient dimensional and tolerance control on the inner medication lumens as described herein. In an example embodiment, the tubing material may be chosen to be a material selected for low leachable and extractable compounds that may contaminate a medication, and that exhibits high biocompatibility with biologic medications.

Housing 703 may be configured to allow easy assembly onto a base side coupler, as through grip features 705, which may allow simple grasping of the device by a user of the apparatus.

Method of Use

In some embodiments, a method for using the apparatus may comprise locating a port using outer housing 503 containing the locator assembly 502, depositing a base plate 501 adhesively and temporarily onto the skin 510 of a patient over an implanted port 513 with opening 515 positioned over a pierceable portion of port 513, disconnecting device side coupler 504 from base side coupler 505, removing outer housing 503 containing the locator assembly 502 from base plate 501, and subsequently attaching a needle assembly 700 provided with device side coupler 704 to the retained base plate 501 via base side coupler 505.

Figures 3, 7B:
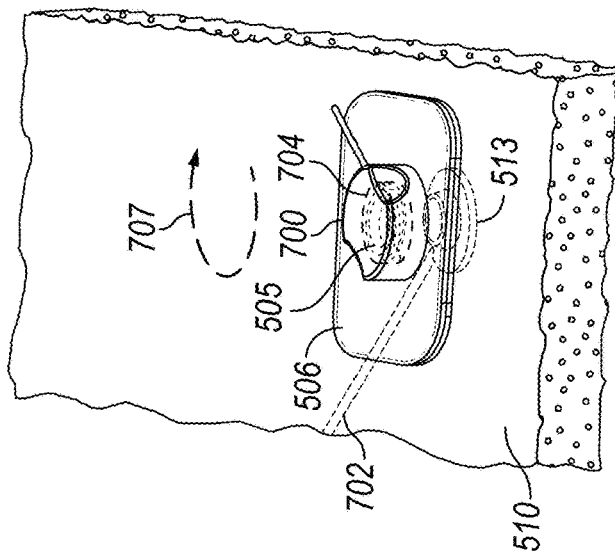
Figures 2, 7B:
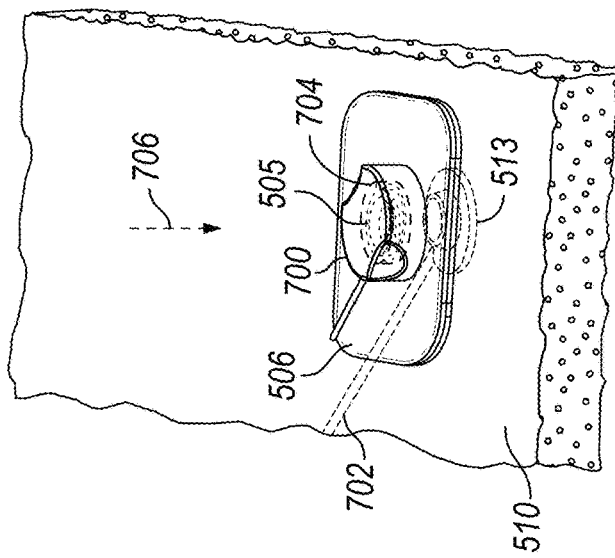
Figures 1, 7B:
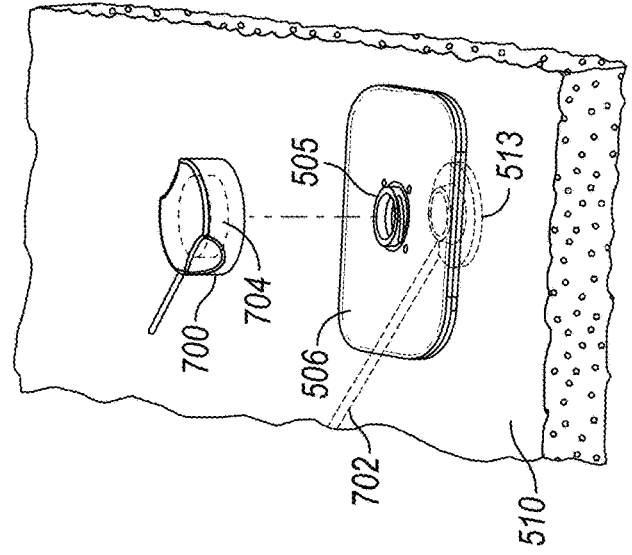

Referring to FIG. 7B-1, device side coupler 704 of needle assembly 700 may be oriented to the base coupler 505. Referring to FIG. 7B-2, needle assembly may be advanced 706 towards the base coupler 505, maintaining alignment with base side coupler 505 until device side coupler 704 engages with the base side coupler 505. As shown in FIG. 7B-3, needle assembly 700 may be then removably attached to base plate 501 by rotating 707 needle assembly 700 relative to fixed base plate 501. Base plate 501, being retained on the skin, may resist rotation caused by the needle assembly 700 during assembly as described. As base plate 501 is located over the implanted access port 513, needle 701, and particularly the point of distal end 701d, may be positioned for insertion into the located port 513 and particularly its pierceable elastomeric septum.

Figures 1, 7C:
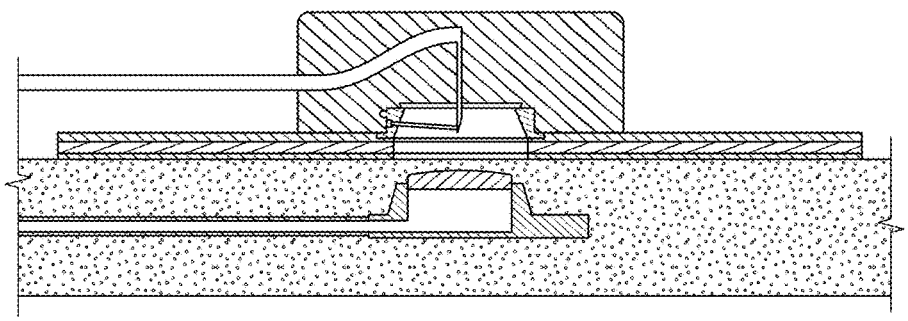
Figures 2, 7C:
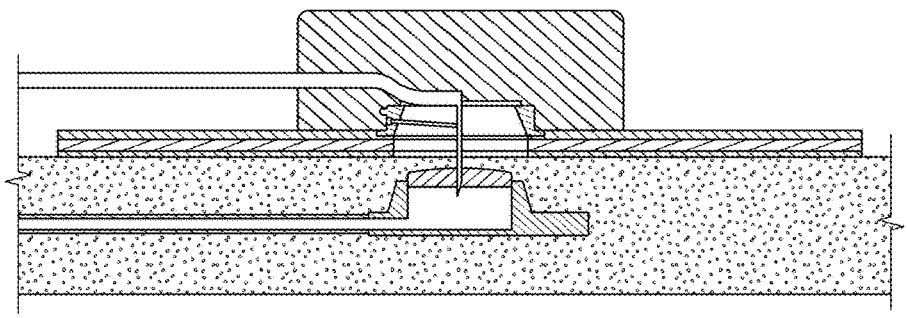

In some embodiments, attaching the housing onto the base plate may unlock the needle and allow it to be advanced into the port, as shown in the cross-section illustrated by FIG. 7C-1. In some embodiments, attaching the housing onto the base place engages the needle into the port automatically, as shown in the cross-section illustrated by FIG. 7C-2.

In some embodiments, a needle secured on the base plate 501 and advanced into the elastomeric septum of port 513 through skin 510 may be used to administer one or more medications to a patient. After administration, needle assembly 700 may be removed by rotating relative to base plate, or alternatively, the entire base plate with needle assembly 700 may be removed as a single unit.

Example Embodiment: Medication Administration with Retained Base Plate and Wearable Injector With reference again to FIGS. 5D-1 to 5D-3, and for purposes of describing the following example embodiment, let it be assumed that an access port has been located as described previously, locating assembly 502 is removed from base plate 501, base plate 501 is situated with base coupler 505, and opening 515 is situated on the skin 510 over a pierceable portion of elastomeric septum 513s, all as previously described. Additionally, the skin 510 may have been marked and/or sterilized as described with reference to FIGS. 6B-1 and 6B-2. One or more medication delivery devices provided with a device side coupler 504 may be subsequently attached to the retained base plate 501 and deliver medications to a patient through the skin 510 and septum 513s. For example, a user may subsequently attach one or more different devices with device side coupler 504 to the base plate coupler 505 and thus the base plate 501, thereby gaining access to the skin 510, access port 513, or port septum 513s, for example, with an injection needle.

Example embodiments of the present disclosure may be advantageously applied to many wearable drug delivery devices. Many drug delivery devices, such as wearable subcutaneous injection devices, use an adhesive element to secure the injector containing medication to a patient's skin. Wearable injectors, once secured to the skin, may advance a percutaneous pointed needle into the subcutaneous tissue and deliver one or more medications to a patient. A wearable injector may refer variously to body-worn drug delivery devices that generally deliver a fixed dose of medication in a specified nominal delivery time via injection or infusion, as by the subcutaneous route of administration. Wearable injectors may be known variously as "wearable" or "patch" devices, "large volume infusers (LVI), "bolus injectors," "bolus infusers," "on-body injectors," or "on-body infusers." Wearable injectors may feature larger volume drug reservoirs and powerful drive mechanisms to support larger volumes, or have longer administration times.

Many wearable injectors may be incorporated with example embodiments of the present disclosure, for example, by eliminating the adhesive element and instead providing a device coupler as described by example embodiments herein, and also by substituting a pointed percutaneous needle with a design suitable for an access port, such as a hollow-bore percutaneous needle with a bent cannula and deflected, sharpened end (e.g., a Huber needle) or other needle as described herein. So configured, a wide variety of wearable injectors provided with a device coupler may be attached to a base coupler, and thus the base plate may be retained on the skin of a patient over an implanted access port located with the apparatus described according to example embodiments herein.

Figure 8A:
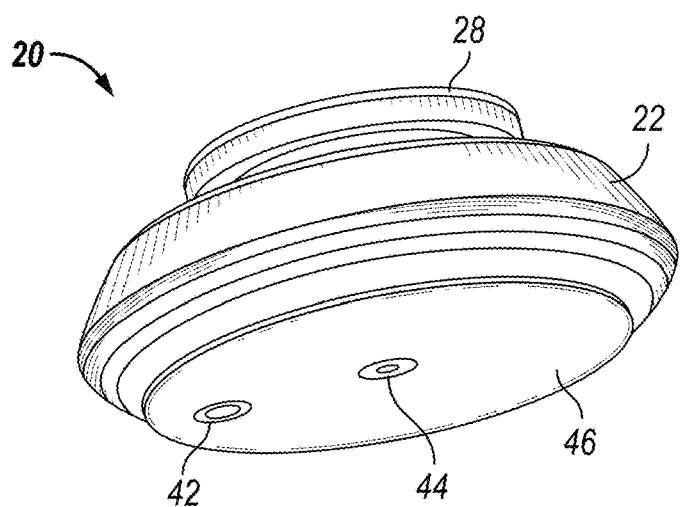
FIG. 8A is a perspective view of a wearable injector according to the related art.

For example, FIG. 8A illustrates a wearable injector according to the related art described in U.S. Patent Application Publication No. 2021/0338928A1 to Hooven, and more specifically, a bottom 46 of the device that may be provided with an adhesive that permits the device to be secured to the patient's skin. In an example, the bottom of the device 46 provided with an adhesive may be eliminated and instead a device coupler may be provided as described in accordance with example embodiments herein. The device illustrated in FIG. 8A is provided merely as an example of related art which may be incorporated with example embodiments described herein and embodiments are not limited thereto. Instead, it serves merely to illustrate how example embodiments of the present disclosure may be integrated into a wide variety of wearable devices. Some embodiments of the present disclosure may be readily applied to other wearable injectors that may be known in the art.

FIGS. 8B-1 to 8B-3 illustrate perspectives view of example embodiments of a medication delivery device configured to be used with example embodiments described herein. With reference to FIG. 8B-1, a wearable injector 800 may be provided with an integral device side coupler 801 configured to cooperate with a base plate as described previously.

As shown in FIG. 8B-2, the device side coupler 801 may be also provided separately to the wearable injector 800 and attached 806 during manufacturing, as by gluing, ultrasonic welding, snap-fit, or other appropriate methods. Alternatively, device side coupler 801 may be provided separately to the wearable injector 800 and attached 806 by a user of the device, such as a patient or healthcare provider, prior to use. In either example, device side coupler 801 and wearable injector 800, once attached, may form an integral unit. In either configuration, device side coupler 801 and wearable injector 800 may be provided with one or more locating features 802, 803 on the wearable device or device coupler, respectively, configured to orient the coupler opening 804 relative to needle opening 805 of wearable injector 800, allowing the needle to protrude through opening 805 when desired.

As seen in FIGS. 8B-1 and 8B-3, coupler opening 804 may be positioned relative to needle opening 805 of wearable injector 800 in a manner allowing the needle to protrude downward through opening 805 when desired, as by pushing the activation button 807. So configured, the needle of wearable injector 800 may be used to administer medication through a port using when desired. In some embodiments, coupler opening 804 may be provided as a substantially annular member or cavity, allowing for easier attachment of a wearable injector 800 to a base side coupler by a user of the apparatus.

Advantageously, this may allow a wearable injector (e.g., an on-body device or OBI), such as a subcutaneous injector, to inject medications intravenously to a port with negligible modification to an existing wearable injector design. This may be further assisted by substituting a skin-piercing needle for a non-coring design suitable for port access, such as a hollow-bore percutaneous needle with a bent cannula and deflected, sharpened end (e.g., a Huber needle) or other needle described herein. Moreover, some embodiments of the present disclosure may utilize existing features of devices, such as needlestick safety and needle insertion/retraction features, with negligible modification to the wearable injector design.

In some embodiments, a wearable injector provided with a device side coupler may be removably attached to a base plate retained on the skin by way of a base side coupler. FIGS. 8C-1 and 8C-2 illustrate a perspective view of how components of the apparatus may be oriented in such a process according to an example embodiment. As seen in FIG. 8C-1, base plate 820 may be attached to the skin 821 over an implanted port 822 with skin side coupler 824 oriented away from the skin, as described previously. Wearable injector 800 with device side coupler 801 and device side opening 804 may be positioned over skin side coupler 824 and advanced downwards 823. Needle 808 may remain in the retracted or "ready" position within wearable injector 800. Referring to FIG. 8C-2, skin side coupler 824 and device side coupler 801 may cooperate to engage wearable injector 800 on base plate 820 affixed to skin 821, in this example case by rotating 825 wearable injector 800 to engage the threaded connection.

Figures 2, 8D:
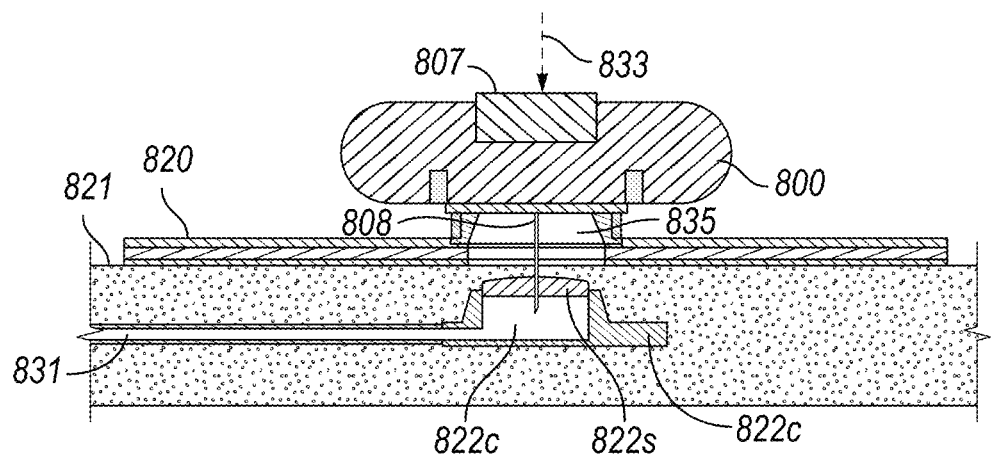

In some embodiments, activation of a wearable injector attached to a base plate may allow an injection needle to puncture the patient's skin and elastomeric septum of a port, placing medication contained within the wearable injector in fluidic communication with one or more of an implanted access port, port cavity, or catheter. As shown in FIGS. 8D-1A and 8D-1B, needle 808 of wearable injector 800 may be positioned over the septum 822s of port 822 but is not yet advanced through the skin 821, tissue 830, or port septum 822s. In other words, wearable injector 800 may be ready to deliver medication to the port 822 when desired by a user of the apparatus, for example, by pressing activation button 807.

In an example embodiment, either or both of skin side coupler 824 and device side coupler 801 may cooperate to situate either or both of the distal end 808d and/or needle 808 of wearable injector 800 at a desired (e.g., predetermined) distance 834 from the skin 821 of a patient prior to performing an injection. This arrangement may ensure needle 808 will penetrate the skin 821 and septum 822s and prevent migration or movement of wearable injector 800 and needle 808 during the injection, ensuring a full dose of medication is delivered to the patient. As shown in FIG. 8D-2, pressing the activation button 807 downwards 833 may urge the distal (e.g., pointed) end of needle 808 out of wearable injector 800 through opening 835 in base plate 820, through the skin 821 and tissue 830, into the port septum 822s, and into the port cavity 822c, allowing medication in wearable injector 800 to be administered to a patient via port catheter 831.

In some embodiments, the wearable injector 800 may be attached to base plate 820 after removal of an outer housing 503 containing the locator assembly 502 from base plate 501 (e.g., after the port is located and base plate 820 is situated on the skin 821 as described previously).

In some embodiments, location of the port may precede attachment of a wearable device to the base plate secured to the skin, as in the foregoing example. The wearable injector and locating assemblies may be separate. In use, the port may be located, the locating assembly removed (retaining the base plate on the skin), both as described previously, whereupon the wearable injector may be assembled onto the base plate after port location takes place.

However, embodiments are not limited thereto, and in some embodiments, the wearable injector may have one or more components of the port locating assembly (e.g., sensors, controller, etc.) incorporated directly into the injector, along with a base plate described previously. Such an embodiment may be used to first locate the implanted port by moving the assembly over the skin. Having located the port, the base plate may be secured over the port, thus positioning the wearable injector deliver medication to a patient through the port. Such embodiments may be particularly advantageous for electromechanical wearable injectors, which may be already provided with a power source, controller, or other features that may be supplemented with the features described herein, for example, port sensors, skin sensors, and controller to detect the port location. Such an arrangement may improve convenience, cost, and reduce complexity of a multi-step process described previously.

Example Embodiment: Medication Administration with Retained Base Plate and Autoinjector With reference again to FIGS. 5D-1 to 5D-3, and for purposes of describing the following example embodiment, let it be assumed that an access port has been located as described previously, locating assembly 502 is removed from base plate 501, base plate 501 is situated with base coupler 505, and opening 515 is situated on the skin 510 over a pierceable portion of elastomeric septum 513s, all as previously described. Additionally, the skin 510 may have been marked and/or sterilized as described with reference to FIGS. 6B-1 and 6B-2. One or more medication delivery devices provided with a device side coupler 504 may be subsequently attached to the retained base plate 501 and deliver medications to a patient through the skin 510 and septum 513s. For example, a user may subsequently attach one or more different devices with device side coupler 504 to the base plate coupler 505 and thus the base plate 501, thereby gaining access to the skin 510, access port 513, or port septum 513s, for example, with an injection needle.

Figure 9A:
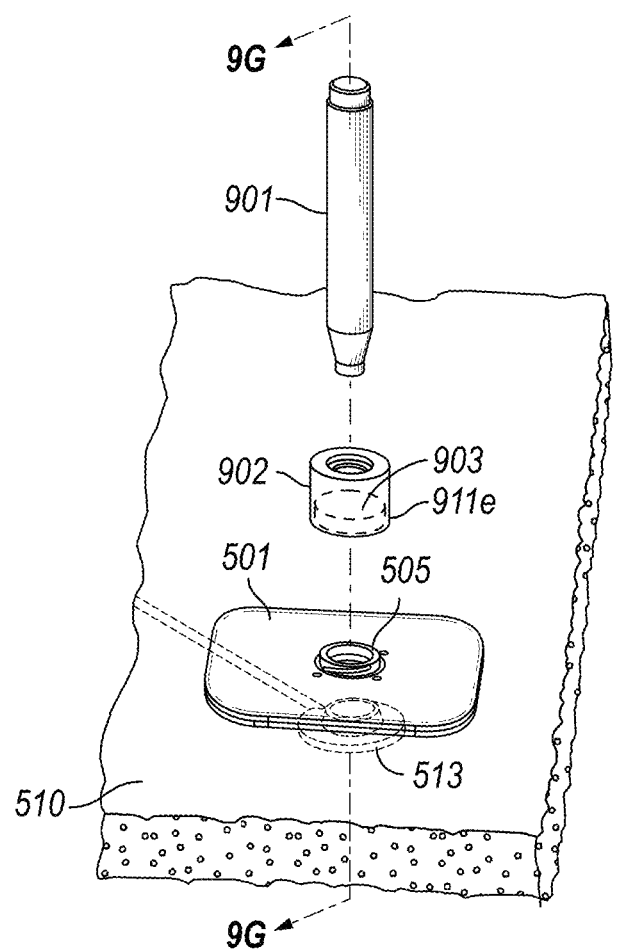
FIG. 9A is a perspective partial cutaway view showing the relationship of an autoinjector in relationship to a retained base plate over an implanted access port, all in accordance with an example embodiment.

FIG. 9A illustrates how an autoinjector guide 902 provided with device side coupler 903 may cooperate with base side coupler 505 to removably attach autoinjector guide 902 to a base plate 501 adhesively retained on the skin 510 over an access port 513 implanted under the skin according to an example embodiment. As illustrated in FIG. 9A, outer housing 503 containing the locator assembly 502 has been removed from base plate 501 as may have been described previously with reference to the example embodiments of FIGS. 6A-6C.

FIG. 9A further illustrates a perspective view of an example embodiment of a medication delivery device comprising a handheld autoinjector 901 configured to be used with the autoinjector guide 902 according to an example embodiment. The autoinjector may refer variously to handheld drug delivery devices that deliver a fixed dose of medication in a specified nominal delivery time. The fixed dose may be, for example 1-10 mL, with injection times of 10 seconds to 3-5 minutes, and multiple autoinjectors may used if desired for a single medication dosing event. Many autoinjectors may be used to deliver subcutaneous injections, as with biologic medications. Autoinjectors may be single-use, disposable devices, or may be provided as a system with one or more reusable components (e.g., a drive mechanism) and one or more single use components (e.g., a drug reservoir and needle, or drug cartridge). The example of FIG. 9A is provided for the sake of illustrating an example embodiment of the present disclosure and should not be construed as limiting use to a specific autoinjector design or injection parameters.

Figure 9D:
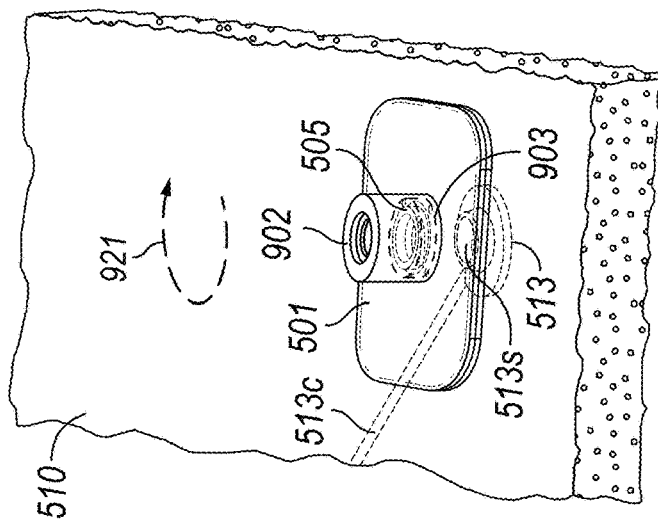
FIGS. 9C and 9D are perspective views showing assembly of an autoinjector adapter in relationship to a retained base plate over an implanted access port, all in accordance with an example embodiment.
Figure 9C:
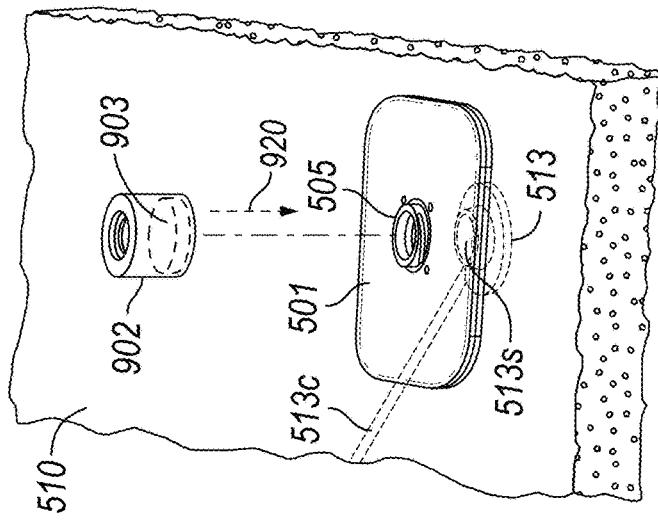
Figure 9B:
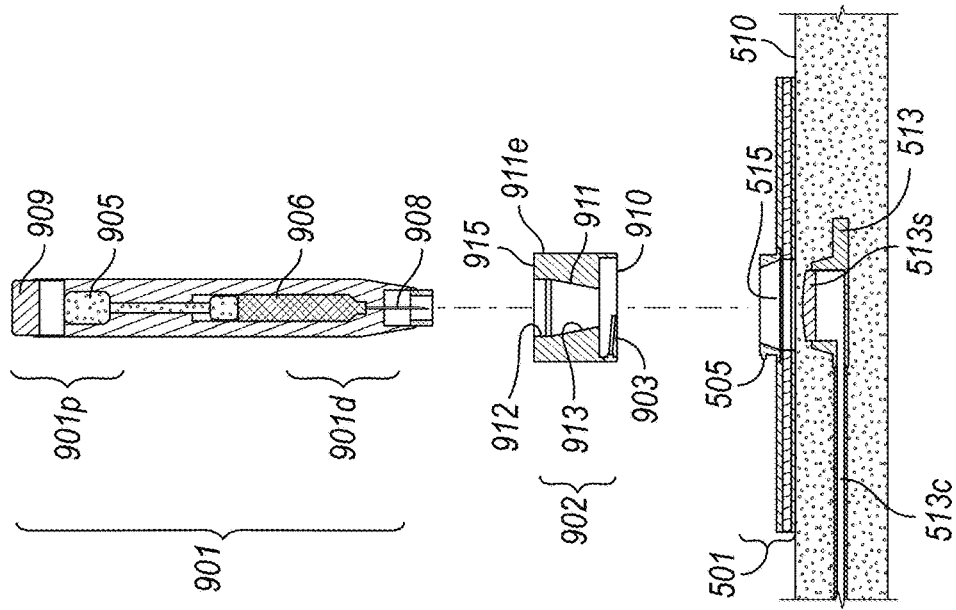
FIG. 9B is a cutaway side view showing the relationship of an autoinjector in relationship to a retained base plate over an implanted access port, all in accordance with an example embodiment.

FIG. 9B illustrates a cross-sectional view of the medication delivery device of FIG. 9A taken along line A-A. Such an autoinjector 901 may comprise a medication reservoir 906 (e.g., a prefilled syringe as shown, or a cartridge), drive mechanism 905, medication delivery needle 908, and optionally, an activation button 909. An autoinjector may take a long, thin form with proximal end 901p held in the hand and distal end 901d with needle 908 oriented towards the skin 510 during injection of a medication. Needle 908 may be a hypodermic needle taking a long, tubular cross section of siliconized rigid medical grade stainless steel. The length of needle 908 may be selected based on the anatomy of the expected injection, and in examples, may vary from 6-12.7 mm, although any needle length may be selected. The point of needle 908 may be selected to avoid damage to the port septum 513s as previously described, with a sharpened distal end or alternatively, with a bent and deflected non-coring needle point. In an example, the bent and deflected non-coring needle point may be a Huber needle point. The needle and/or needle point may optionally be protected after use by a safety mechanism to protect a user of autoinjector 901 against needlesticks and bloodborne pathogen exposure. Autoinjectors may include many and varying configurations and features beyond those described herein.

To perform an injection using autoinjector 901 (e.g., without the base plate 501 or other features described herein), as in a subcutaneous injection, a user may place distal end 901d against the skin 510 and activate autoinjector 901, as by pressing button 909 or, if button 909 is not provided, alternatively by grasping proximal end 901p in the hand and pressing distal end 901d against the skin 510. The autoinjector, upon activation, may advance needle 908 outward from distal end 901d a fixed distance into the skin 510. The distance needle 908 may be advanced may vary by autoinjector 901 design, needle 908 provided, pharmacokinetics of medication in reservoir 906, expected patient physiology, or other factors.

This approach may be adaptable to use with the present embodiments (e.g., the port locating apparatus 500) for other types of injections, allowing autoinjector 901 to deliver an injection through the skin 510 and into the septum 513s of access port 513. In some embodiments, attachment of autoinjector guide 902 to base plate 501 may position the distal end 901d of autoinjector 901 within opening 515 of base plate 501 to subsequently puncture the patient's skin 510 and septum 513s, placing the needle 908 in fluidic communication with septum 513s and catheter 513c of implanted access port 513 to deliver a medication to a patient.

This may advantageously allow the autoinjector, while handheld, to deliver an injection of medication into a patient through the access port properly and without discomfort or clinical training. The example embodiment may also allow autoinjectors that were previously confined to subcutaneous injections through the skin without an implanted port to perform other types of injections, such as those through an implanted port, if desired.

Autoinjector Guide Intro

With further reference to FIG. 9B, in some embodiments, an autoinjector guide 902 may be provided with a device side coupler 903 and may be configured to be removably attached to a base plate 501 retained on the skin 510 by way of base side coupler 505. Device side coupler 903 provided on autoinjector guide 902 may be generally as previously described (e.g., device side coupler 504 of locating assembly 502). In some embodiments, an autoinjector guide 902 may be provided as part of a kit of components also including a port locating assembly 502 and a base plate 501.

Autoinjector guide 902 may be provided as a substantially annular member with an exterior guide surface 911e and an interior guide surface 911 comprising autoinjector side surface 913 and optional lead 912. Such an annular design may be advantageously configured to allow for straightforward attachment of an autoinjector guide 902 to base side coupler 505 by a user of the retained base plate 501 and/or port locating assembly 200.

Exterior guide surface 911e may be cylindrical as shown or may take any other contour or profile. Interior guide surface 911 may be optionally provided with lead 912 directed from the autoinjector side surface 915 towards the base side surface 910 to locate autoinjector 901 within autoinjector guide 902 and smooth insertion into autoinjector guide 902. If provided, lead 912 may be conical as shown, or may take any other contour or profile, and may also comprise rounded or chamfered surfaces, particularly at the intersection of lead 912 and autoinjector side surface 915. The inclusion, omission, or contour of lead 912 may be determined based on the autoinjector 901 to be used with the apparatus.

Interior guide surface 911 may be cylindrical as shown or may take any other contour or profile or combinations thereof. For example, lead 912 and autoinjector contact surface 913 may form a combination of profiles cooperating with a distal profile of an autoinjector 901 used with the apparatus 500. Autoinjector side surface 913 may narrow from the autoinjector side surface 915 towards base side surface 910, as in the form of a narrowing cone, or may narrow and then flare towards the base side surface 910, creating an hourglass contour. Such an hourglass contour may be advantageous with certain autoinjector designs to prevent inadvertent activation. In some embodiments, either or both of lead 912 and autoinjector side surface 913 may take a substantially narrowing section from the autoinjector side surface 915 to the base side surface 910. In some embodiments, either or both of lead 912 and autoinjector side surface 913 may take a substantially narrowing section then widening section from the autoinjector side surface 915 to the base side surface 910. Lead 912 and autoinjector side surface 913 may also be joined with a smooth profile, as to guide autoinjector 901 smoothly during insertion from the autoinjector side surface 915 to base side surface 910.

Insertion of Autoinjector into Guide

In an example embodiment, distal end 901*d* of autoinjector 901, when inserted into autoinjector guide 902 attached to base plate 501, may position needle 908 of autoinjector 901 to perform an injection into septum 513*s* of access port 513 below the base plate 501 when desired by a user of the apparatus.

In an example embodiment, either or both of lead 912 and autoinjector side surface 913 may cooperate to situate either or both of the distal end 901*d* and/or needle 908 of autoinjector 901 within the area defined by opening 515 of base plate 501. For instance, either or both of lead 912 and autoinjector side surface 913 may cooperate to position distal end 901*d* towards a portion of opening 515 in base plate 501. A portion of opening 515 may comprise, for example, the center point of opening 515 or a pierceable portion of port septum 513*s* under opening 515.

In an example embodiment, either or both of lead 912 and autoinjector side surface 913 may cooperate to situate either or both of the distal end 901*d* and/or needle 908 of autoinjector 901 at a desired distance from the skin 510 of a patient prior to performing an injection with autoinjector 901. Lead 912 and autoinjector side surface 913 may take a substantially narrowing section from the autoinjector side surface 915 to the base side surface 910 of autoinjector guide 902. Such a narrowing profile may be shaped to cooperate with a distal profile, as by having a matching profile, to axially situate the distal end 901*d* and particularly needle 908 at a desired distance from one or more of the skin side surface 512 or the skin 510.

Such configurations may naturally urge the distal end 901*d* towards opening 515 as insertion of autoinjector 901 into guide 902 proceeds from autoinjector side surface 913 towards base side surface 910, ultimately disposing the needle 908 of autoinjector 901 over or on the skin 510 covering septum 513*s* and allowing subsequent injection into access port 513. This arrangement may ensure needle 908 will penetrate the skin 510 and septum 513*s* and prevent migration or movement of the autoinjector 901 and needle 908 during the injection, ensuring a full dose of medication is delivered to access port 513. Such positioning may take place before an injection is performed with autoinjector 901, but positioning may also take place during the injection process itself, depending on design of autoinjector 901.

Autoinjector guide 902 may also be configured to prevent the incorrect end of autoinjector 901 from being inserted, or only allowing the injection end (e.g., 901*d*) from being inserted into guide 902. In an example embodiment, either or both of lead 912 and autoinjector side surface 913 may be contoured and/or dimensioned to allow insertion of distal end 901*d* with one or more specific distal profiles of autoinjector 901. In some embodiments, either or both of lead 912 and autoinjector side surface 913 may be contoured and/or dimensioned to prevent insertion of proximal end 901*p* of autoinjector 901.

Autoinjector guide 902 may also be configured to restrict or permit specific autoinjectors from being used with the apparatus 500, regardless of their distal end 901*d* or autoinjector side surface 913. Such a configuration may be advantageous to prevent an incorrect or unanticipated medication from being administered through access port 513. In some embodiments, either or both of lead 912 and autoinjector side surface 913 are contoured to allow insertion of an autoinjector 901 provided with one or more specific distal profiles. In some embodiments, either or both of lead 912 and autoinjector side surface 913 may be contoured to prevent insertion of an autoinjector 901 provided with one or more specific distal profiles.

Method of Use

In an example embodiment, distal end 901*d*, when inserted into autoinjector guide 902 attached to base plate 501, may be positioned to allow the autoinjector 901, upon activation by a user, to advance needle 908 through the skin 510 and septum 513*s*, thereby placing reservoir 906 into fluidic communication with access port 513 and catheter 513*c*.

In an example embodiment, performing an injection with the apparatus 500 may comprise one or more of attaching an autoinjector guide 902 to base plate 501 retained on the skin 510 of a patient, aligning either or both of distal end 901*d* or distal profile with either or both of the lead 912 or autoinjector side surface 913, situating the distal end 901*d* of autoinjector 901 within autoinjector guide 902 in proximity to skin 510, advancing distal end 901*d* towards the skin 510, optionally activating autoinjector 901, advancing needle 908 through skin 510 and septum 513*s*, placing needle 908 in fluidic communication with access port 513, or delivering a medication from reservoir 906 through needle 908.

FIG. 9C shows the initial configuration of an example embodiment in anticipation of an autoinjector guide 902 being removably attached to base plate 501. Base plate 501 may be retained on the skin 510 of a patient, with opening 515 positioned over an implanted access port 513. An autoinjector guide 902 with device side coupler 903 may be positioned coaxially over the base side coupler 504 of base plate 501. Autoinjector guide 902 may be advanced towards base plate 501 in a direction 920, allowing device side coupler 903 to be connected to base side coupler 505.

In the illustrative example of FIGS. 9C to 9F-2, couplers 903 and 505 may form a threaded connection. As seen in FIG. 9D, connection may take place by rotating guide 902 in a clockwise direction 921, so as to thread device side coupler 903 onto base side coupler 505 of base plate 501. In some embodiments, base plate 501, being retained on the skin, may resist torsional forces caused by rotation of autoinjector guide 902 and device side coupler 903—for example, in the clockwise direction 921 or an opposite, counterclockwise direction.

Figures 2, 9E:
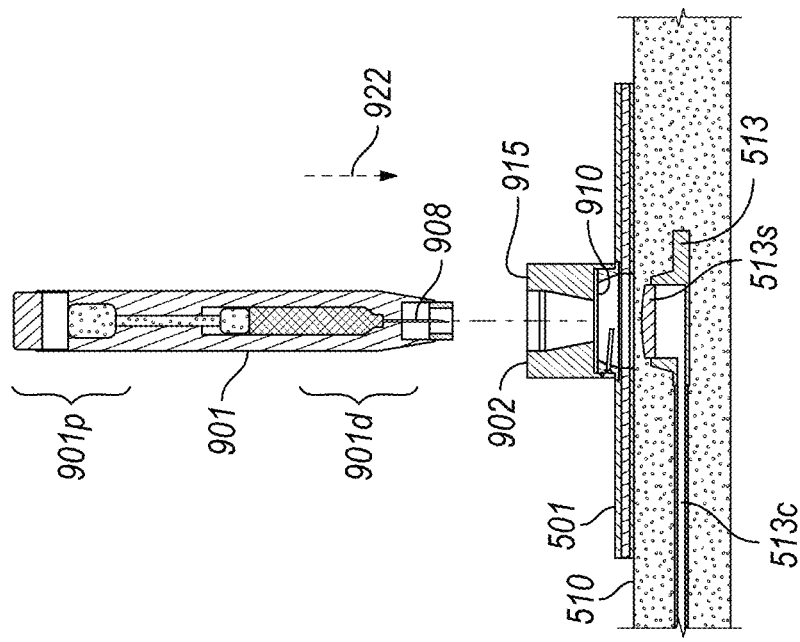
Figures 1, 9E:
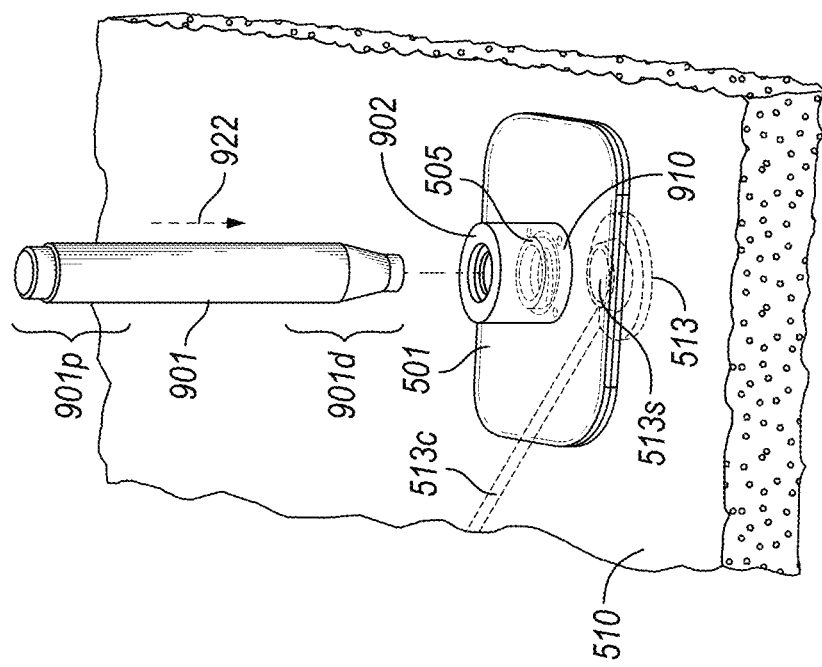

Referring to FIG. 9E-1, autoinjector 901 may be held in a user's hand and advanced 922 from autoinjector side surface 911 towards the base side surface 910 of autoinjector guide 902, positioning the distal end 901d of autoinjector 901 closer to the skin 510 within the autoinjector guide 902. As seen in FIG. 9E-2, during advancement 922, as distal end 901d approaches the lead 912 of guide 902, the needle 908 may be maintained in axial alignment (e.g., substantially positioned or centered over) with the septum 513s of access port 513.

Referring to FIGS. 9F-1 & 9F-2, the desired distance of distal end 901d from the skin 510 within the autoinjector guide 902 may be determined as previously described, for example, through the arrangement of one or more of the interior guide surface 911, lead 912, and contact surface 913 of autoinjector guide 902. After continued advancement 923, autoinjector 901 may remain handheld by the user, removably inserted into autoinjector guide 902, on or near the skin 510, and maintained in axial alignment with the septum 513s of access port 513.

Figure 9G:
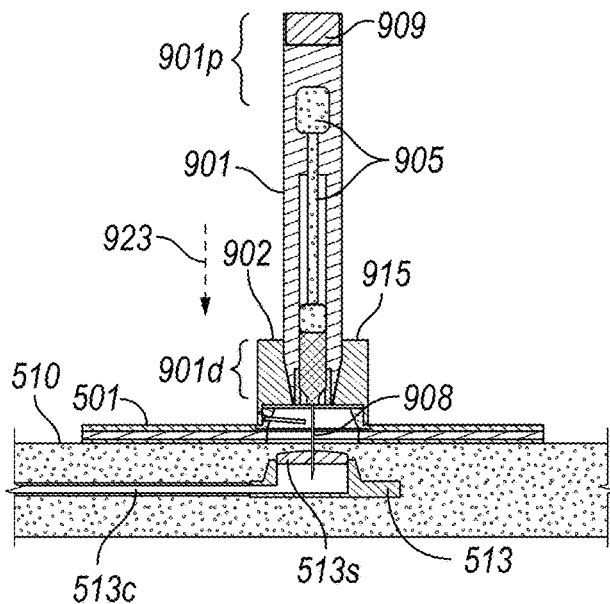
FIG. 9G is a cutaway side view of an autoinjector installed on a retained base plate during medication delivery to an implanted access port, all in accordance with an example embodiment.

Referring to FIG. 9G, autoinjector 901, now situated on or near the skin 510 covering septum 513s of access port 513, may continue to be held in the hand, and may be activated when desired by a user to perform an injection into access port 513. In some embodiments, a user activating autoinjector 901 may comprise holding the autoinjector 901 and depressing button 909 with the distal end 901d enclosed in autoinjector guide 902. In some embodiments, a user activating autoinjector 901 may comprise holding the autoinjector 901 and even advancing 923 the distal end 901d still further towards the skin 510 while enclosed in autoinjector guide 902.

As the autoinjector 901 is activated, needle 908 may advance towards the skin 510, sequentially puncturing the skin 510, subcutaneous tissue if present, and port septum 513s, thus being placed in fluidic communication with access port 513 and catheter 513c. Drive mechanism 905 then injects medication reservoir 906 through the needle and into port 513, which is ultimately delivered to the patient via catheter 513c. In some embodiments, performing an injection may comprise activating the autoinjector 901, allowing needle 908 to successively pierce the skin 510 and septum 513s, placing reservoir 906 in fluidic communication with access port 513, delivering medication to a patient by way of catheter 513c, and optionally removing the autoinjector 901 from the autoinjector guide 902 after medication delivery is completed.

Example embodiments herein may advantageously work with many different common autoinjectors that retract, shield, or otherwise cover the needle 908 after use. For instance, needle 908 may be retracted into or covered by autoinjector 901 at the completion of medication administration either prior to or upon removal of the autoinjector 901 from autoinjector guide 902. Such devices may be intended to reduce patient anxiety from a visible injection needle or to protect against accidental needlestick injuries.

Example Embodiment: Method for Administering at Least One Drug to a Patient

Figure 13:
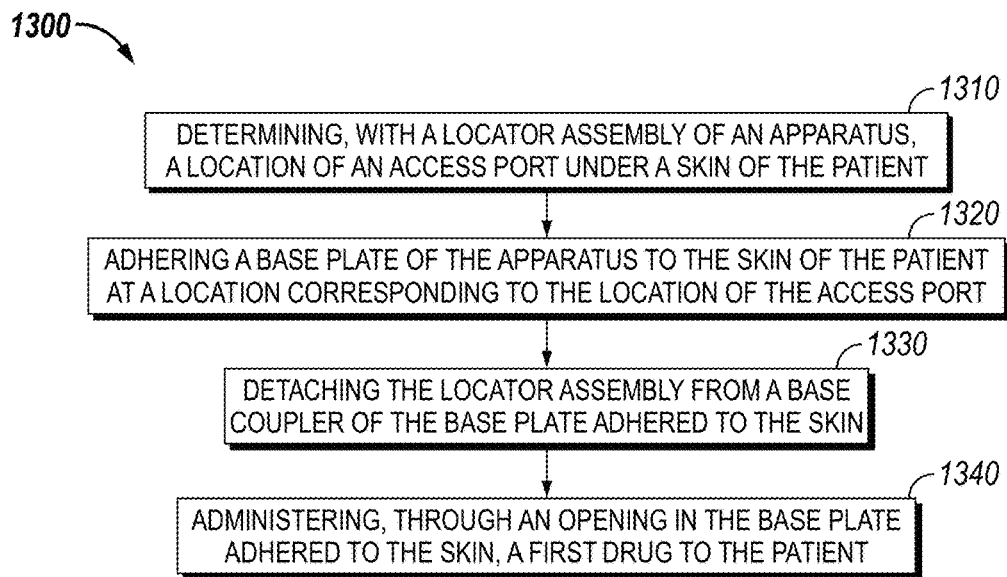
FIG. 13 illustrates a flowchart for an example method for administering at least one drug to a patient according to an example embodiment.

With reference to FIG. 13, a method 1300 for administering at least one drug to a patient according to an example embodiment may include determining 1310, with a locator assembly 502 of an apparatus, a location of an access port 513 under a skin of the patient. The method may further include adhering 1320 a base plate 501 of the apparatus to the skin of the patient at a location corresponding to the location of the access port 513, detaching 1330 the locator assembly 502 from a base coupler 505 of the base plate 501 adhered to the skin, and administering 1340, through an opening in the base plate 501 adhered to the skin, a first drug to the patient.

In some embodiments, the administering the first drug to the patient may further include attaching a medication administration device (also referred to herein as a medication delivery device) to the base coupler 505. The medication administration device may include a buttress structured to protrude within the opening in the base plate and restrict detachment of the medication administration device from the base coupler. The medication administration device may be as described herein—for example, an injection needle assembly 700, a wearable injector 800, or an autoinjector guide 902—although embodiments are not limited thereto.

Thus, in some embodiments, the administering the first drug to the patient may further include attaching an autoinjector guide 902 to the base coupler 505, and using an autoinjector 901 with the autoinjector guide 902 to administer the first drug to the patient through the opening in the base plate 501.

In some embodiments, the method may further include, prior to the using the autoinjector 901, replacing a needle of a syringe with an autoinjector needle to form the autoinjector 901.

In some embodiments, the administering the first drug to the patient may include attaching an injection needle assembly 700 to the base coupler 505, and using the injection needle assembly 700 to puncture, via the opening, the skin of the patient and pierce an elastomeric septum of the access port to thereby place the injection needle assembly 700 in fluidic coupling with the access port 513 and administer the first drug to the patient therethrough.

In some embodiments, the administering the first drug to the patient may further include attaching a wearable injector 800 to the base coupler 505, and causing protrusion of a needle of the wearable injector 800 to puncture, via the opening, the skin of the patient and pierce an elastomeric septum of the access port 513 to thereby place the wearable injector 800 in fluidic coupling with the access port 513 and administer the first drug to the patient therethrough.

In some embodiments, the first drug administered by a medication administration device as described herein may be part of a regimen of drugs to be used to treat a condition of the patient.

In some embodiments, the method may further include administering a second drug either via use of the base plate 501 or separate from the base plate 501. For example, the method may further include administering a second drug subcutaneously or intravenously at another location on the patient's skin.

In some embodiments, the method may further include adhering a second base plate to the skin of the patient at a location adjacent to the location of the first base plate 501, and administering, through an opening in the second base plate, a second drug to the patient.

In some embodiments, the method may further include, prior to administering the first drug to the patient, sterilizing the skin of the patient exposed by the opening of the base plate 501 with a sterilizing swab.

Example Embodiment: Method for Administering Drugs to a Patient

Figure 14:
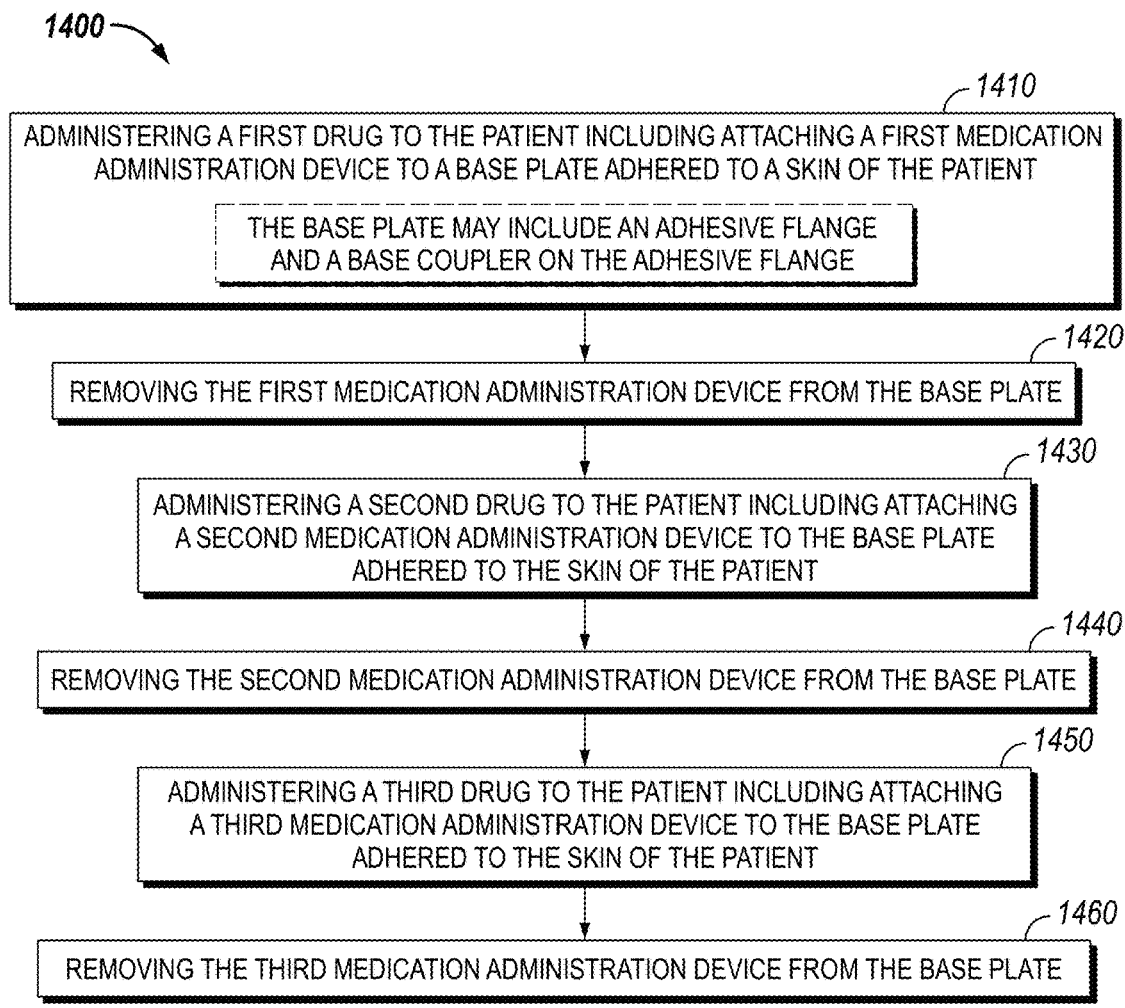
FIG. 14 illustrates a flowchart for an example method for administering drugs to a patient according to an example embodiment.

With reference to FIG. 14, a method 1400 for administering drugs (e.g., as a regimen) to a patient according to an example embodiment may include administering 1410 a first drug to the patient including attaching a first medication administration device to a base plate 501 adhered to a skin of the patient, removing 1420 the first medication administration device from the base plate, administering 1430 a second drug to the patient including attaching a second medication administration device to the base plate 501 adhered to the skin of the patient, removing 1440 the second medication administration device from the base plate 501, administering 1450 a third drug to the patient including attaching a third medication administration device to the base plate 501 adhered to the skin of the patient, and removing 1460 the third medication administration device from the base plate 501. As described by example herein, the base plate 501 may include an adhesive flange and a base coupler on the adhesive flange.

In some embodiments, the first, second, and third medication administration devices may be different types of medication administration devices, which may be as described herein. For example, the medication administration devices may be different ones of an autoinjector 901, an injection needle assembly 700, or a wearable injector 800, although embodiments are not limited thereto.

In some embodiments, at least one of the first, second, or third medication administration devices may be attached to the base coupler 505 of the base plate 501, and another at least one of the first, second, or third medication administration devices may be attached to a second base coupler of the base plate 501.

In some embodiments, the method may further include administering a fourth drug to the patient including attaching a fourth medication administration device to a second base plate adhered to the skin of the patient. The second base plate may be adjacent to the base plate 501 on the skin of the patient.

In some embodiments, each of the first, second, and third medication administration devices may be a same type of medication administration device. For example, in some embodiments, the same type of medication administration device may be at least one of an autoinjector 901, an injection needle assembly 700, or a wearable injector 800, although embodiments are not limited thereto.

In some embodiments, the first, second, and third drugs may include and/or be a part of a drug regimen for treating a condition of the patient, and the method may include administering further drugs to the patient. The first, second, and third drugs (and further drugs thereto) may be administered during a same treatment session, or over the course of days or weeks or months.

In some embodiments, the method may further include determining a location of an access port 513 under the skin of the patient, and adhering the base plate 501 to the skin of the patient at a location corresponding to the location of the access port 513.

In some embodiments, the base plate may include an opening extending through the adhesive flange and the base coupler 505, and at least one of the first, second, or third drugs may be administered to the patient via the opening.

In some embodiments, at least one of the first, second, or third drugs may be administered to the patient subcutaneously. In such an example, while the one of the first, second, or third drugs may be administered via the opening of the base plate 501, embodiments are not limited thereto, and in other examples, one or more the drugs may be administered via a second location on the patient's skin.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platform. A processor may be any kind of computational or processing device capable of executing program instructions, codes, binary instructions, and the like. The processor may be or may include a signal processor, digital processor, embedded processor, microprocessor, or any variant such as a co-processor (math co-processor, graphic co-processor, communication co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions, and the like described herein may be implemented in one or more thread. The thread may spawn other threads that may have assigned priorities associated with them; the processor may execute these threads based on priority or any other order based on instructions provided in the program code. The processor, or any machine utilizing one, may include non-transitory memory that stores methods, codes, instructions, and programs as described herein and elsewhere. The processor may access a non-transitory storage medium through an interface that may store methods, codes, and instructions as described herein and elsewhere. The storage medium associated with the processor for storing methods, programs, codes, program instructions, or other type of instructions capable of being executed by the computing or processing device may include but may not be limited to one or more of a CD-ROM, DVD, memory, hard disk, flash drive, RAM, ROM, cache, and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server, and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code, and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client, and other variants such as secondary client, host client, distributed client, and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of a program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code, and/or instructions. A central repository may provide program instructions to be executed on different devices. In this implementation, the remote repository may act as a storage medium for program code, instructions, and programs.

In embodiments, one or more of the controllers, circuits, systems, data collectors, storage systems, network elements, or the like as described throughout this disclosure may be embodied in or on an integrated circuit, such as an analog, digital, or mixed signal circuit, such as a microprocessor, a programmable logic controller, an application-specific integrated circuit, a field programmable gate array, or other circuit, such as embodied on one or more chips disposed on one or more circuit boards, such as to provide in hardware (with potentially accelerated speed, energy performance, input-output performance, or the like) one or more of the functions described herein. This may include setting up circuits with up to billions of logic gates, flip-flops, multiplexers, and other circuits in a small space, facilitating high speed processing, low power dissipation, and reduced manufacturing cost compared with board-level integration. In embodiments, a digital IC, typically a microprocessor, digital signal processor, microcontroller, or the like may use Boolean algebra to process digital signals to embody complex logic, such as involved in the circuits, controllers, and other systems described herein. In embodiments, a data collector, an expert system, a storage system, or the like may be embodied as a digital integrated circuit ("IC"), such as a logic IC, memory chip, interface IC (e.g., a level shifter, a serializer, a deserializer, and the like), a power management IC and/or a programmable device; an analog integrated circuit, such as a linear IC, RF IC, or the like, or a mixed signal IC, such as a data acquisition IC (including A/D converters, D/A converter, digital potentiometers) and/or a clock/timing IC.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM, and the like. The processes, methods, program codes, instructions described herein and elsewhere may be executed by one or more of the network infrastructural elements. The methods and systems described herein may be configured for use with any kind of private, community, or hybrid cloud computing network or cloud computing environment, including those which involve features of software as a service ("SaaS"), platform as a service ("PaaS"), and/or infrastructure as a service ("IaaS").

The methods, program codes, and instructions described herein and elsewhere may be implemented on a cellular network having multiple cells. The cellular network may either be frequency division multiple access ("FDMA") network or code division multiple access ("CDMA") network. The cellular network may include mobile devices, cell sites, base stations, repeaters, antennas, towers, and the like. The cell network may be a GSM, GPRS, 3G, EVDO, mesh, or other networks types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable transitory and/or non-transitory media that may include: computer components, devices, and recording media that retain digital data used for computing for some interval of time; semiconductor storage known as random access memory ("RAM"); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, stand-alone RAM disks, zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the Figures, imply logical boundaries between the elements. However, according to software or hardware engineering practices, the depicted elements and the functions thereof may be implemented on machines through computer executable transitory and/or non-transitory media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the example embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

While the present disclosure has been illustrated and described in detail in the drawings and foregoing description, the same is to be considered as illustrative and not restrictive in character, it being understood that only certain exemplary embodiments have been shown and described, and that all changes and modifications that come within the spirit of the present disclosure are desired to be protected. It should be understood that while the use of words such as "preferable," "preferably," "preferred" or "more preferred" utilized in the description above indicate that the feature so described may be more desirable, it nonetheless may not be necessary, and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. The term "of" may connote an association with, or a connection to, another item, as well as a belonging to, or a connection with, the other item as informed by the context in which it is used. The terms "coupled to," "coupled with" and the like include indirect connection and coupling, and further include but do not require a direct coupling or connection unless expressly indicated to the contrary. When the language "at least a portion" and/or "a portion" is used, the item can include a portion and/or the entire item unless specifically stated to the contrary.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure, and does not pose a limitation on the scope of the disclosure unless otherwise claimed. No language in the specification should be construed as indicating any non-claimed element as essential to the practice of the disclosure.

While the foregoing written description enables one skilled in the art to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

Any element in a claim that does not explicitly state "means for" performing a specified function, or "step for" performing a specified function, is not to be interpreted as a "means" or "step" clause as specified in 35 U.S.C. § 112(f). In particular, any use of "step of" in the claims is not intended to invoke the provision of 35 U.S.C. § 112(f).

Persons skilled in the art may appreciate that numerous design configurations may be possible to enjoy the functional benefits of the present disclosure. Thus, given the wide variety of configurations and arrangements of embodiments of the present disclosure, the scope of the disclosure is reflected by the breadth of the claims below rather than narrowed by the embodiments described above.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

What is claimed is:

1. A method for administering at least one drug to a patient, comprising:
    determining, with a locator assembly of an apparatus, a location of an access port under a skin of the patient;
    adhering a base plate of the apparatus to the skin of the patient at a location corresponding to the location of the access port;
    detaching the locator assembly from a base coupler of the base plate adhered to the skin; and
    administering, through an opening in the base plate adhered to the skin, a first drug to the patient.

2. The method of claim 1, wherein the administering the first drug to the patient further comprises:
    attaching a medication administration device to the base coupler,
    wherein the medication administration device includes a buttress structured to protrude within the opening in the base plate and restrict detachment of the medication administration device from the base coupler.

3. The method of claim 1, wherein the administering the first drug to the patient further comprises:
    attaching an autoinjector guide to the base coupler; and
    using an autoinjector with the autoinjector guide to administer the first drug to the patient through the opening in the base plate.

4. The method of claim 3, further comprising:
    prior to the using the autoinjector, replacing a needle of a syringe with an autoinjector needle to form the autoinjector.

5. The method of claim 1, wherein the administering the first drug to the patient further comprises:
    attaching an injection needle assembly to the base coupler; and
    using the injection needle assembly to puncture, via the opening, the skin of the patient and pierce an elastomeric septum of the access port to thereby place the injection needle assembly in fluidic coupling with the access port and administer the first drug to the patient therethrough.

6. The method of claim 1, wherein the administering the first drug to the patient further comprises:
    attaching a wearable injector to the base coupler; and
    causing protrusion of a needle of the wearable injector to puncture, via the opening, the skin of the patient and pierce an elastomeric septum of the access port to thereby place the wearable injector in fluidic coupling with the access port and administer the first drug to the patient therethrough.

7. The method of claim 1, further comprising:
    adhering a second base plate to the skin of the patient at a location adjacent to the location of the first base plate; and
    administering, through an opening in the second base plate, a second drug to the patient.

8. The method of claim 1, further comprising:
    prior to administering the first drug to the patient, sterilizing the skin of the patient exposed by the opening of the base plate with a sterilizing swab.

9. A method for administering drugs to a patient, comprising:
    determining a location of an access port under a skin of the patient;
    adhering a base plate to the skin of the patient at a location corresponding to the location of the access port;

administering a first drug to the patient including attaching a first medication administration device to the base plate adhered to the skin of the patient;

removing the first medication administration device from the base plate;

administering a second drug to the patient including attaching a second medication administration device to the base plate adhered to the skin of the patient;

removing the second medication administration device from the base plate;

administering a third drug to the patient including attaching a third medication administration device to the base plate adhered to the skin of the patient; and removing the third medication administration device from the base plate, wherein the base plate includes an adhesive flange and a base coupler on the adhesive flange.

10. The method of claim 9, wherein the first, second, and third medication administration devices are different types of medication administration devices.

11. The method of claim 9, wherein at least one of the first, second, or third medication administration devices is attached to the base coupler of the base plate, and another at least one of the first, second, or third medication administration devices is attached to a second base coupler of the base plate.

12. The method of claim 9, further comprising:

administering a fourth drug to the patient including attaching a fourth medication administration device to a second base plate adhered to the skin of the patient, wherein the second base plate is adjacent to the base plate on the skin of the patient.

13. The method of claim 9, wherein each of the first, second, and third medication administration devices is a same type of medication administration device.

14. The method of claim 13, wherein the same type of medication administration device is at least one of an autoinjector, an injection needle assembly, or a wearable injector.

15. The method of claim 9, wherein the first, second, and third drugs comprise a regimen for treating a condition of the patient.

16. The method of claim 9, wherein the base plate includes an opening extending through the adhesive flange and the base coupler, and at least one of the first, second, or third drugs is administered to the patient via the opening.

17. The method of claim 9, wherein at least one of the first, second, or third drugs is administered to the patient subcutaneously.

* * * * *